(12) United States Patent
Wang et al.

(10) Patent No.: US 7,279,460 B2
(45) Date of Patent: Oct. 9, 2007

(54) CHEMOKINE TECK POLYPEPTIDES

(75) Inventors: Wei Wang, Palo Alto, CA (US); Kurt C. Gish, Sunnyvale, CA (US); Thomas J. Schall, Menlo Park, CA (US); Alain Vicari, Mountain View, CA (US); Albert Zlotnik, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 493 days.

(21) Appl. No.: 10/754,071

(22) Filed: Jan. 7, 2004

(65) Prior Publication Data

US 2004/0137578 A1 Jul. 15, 2004

Related U.S. Application Data

(62) Division of application No. 10/039,659, filed on Jan. 3, 2002, now Pat. No. 6,723,520, which is a division of application No. 08/887,977, filed on Jul. 3, 1997, now abandoned.

(60) Provisional application No. 60/048,593, filed on Jun. 4, 1997, provisional application No. 60/028,329, filed on Oct. 11, 1996, provisional application No. 60/021,664, filed on Jul. 5, 1996.

(51) Int. Cl.
*C07K 14/52* (2006.01)
*C07K 14/475* (2006.01)

(52) U.S. Cl. .............................. 514/12; 514/2; 530/350

(58) Field of Classification Search ..................... None
See application file for complete search history.

(56) References Cited

U.S. PATENT DOCUMENTS

| | | | |
|---|---|---|---|
| 5,681,930 A | 10/1997 | Radka et al. | |
| 5,981,231 A | 11/1999 | Wei et al. | |

FOREIGN PATENT DOCUMENTS

| | | |
|---|---|---|
| WO | WO 96/05856 | 2/1996 |
| WO | WO 96/16979 | 6/1996 |
| WO | WO 96/22374 | 7/1996 |
| WO | WO 96/24668 | 8/1996 |

OTHER PUBLICATIONS

Ahuja et al., "Chemokine receptors and molecular mimicry," *Immunol Today*, 15(6):281-287 (1994).
Alkhatib et al., "CC CKR5: a RANTES, MIP-1α, MIP-1β receptor as a fusion cofactor for macrophage-tropic HIV-1," *Science*, 272(5270):1955-1958 (1996).
Baba et al., "Identification of CCR6, the specific receptor for a novel lymphocyte-directed CC chemokine LARC," *J Biol Chem*, 272(23):14893-14898 (1997).
Bacon and Schall, "Chemokines as mediators of allergic inflammation," *Int Arch Allergy Immunol*, 109(2):97-109 (1996).
Balter, "A second coreceptor for HIV in early stages of infection," *Science*, 272(5269):1740 (1996).
Bonner, *EMBL Database*, Entry HS459841, Accession No. U45984 (1996).
Bork, "Powers and pitfalls in sequence analysis: the 70% hurdle," *Genome Res*, 10(4):398-400 (2000).
Bork and Bairoch, "Go hunting in sequence databases but watch out for the traps," *Trends Genet*, 12(10):425-427 (1996).
Brenner, "Errors in genome annotation," *Trends Genet*, 15(4):132-133 (1999).
Clark-Lewis et al., "Structure-activity relationships of chemokines," *J Leukoc Biol*, 57(5):703-711 (1995).
Deng et al., "Identification of a major co-receptor for primary isolates of HIV-1," *Nature*, 381(6584):661-666 (1996).
Doerke et al., "Protein annotation: detective work for function prediction," *Trends Genet*, 14(6):248-250 (1998).
Dragic et al., "HIV-1 entry into CD4+ cells is mediated by the chemokine receptor CC-CKR-5," *Nature*, 381(6584):667-673 (1996).
Gronenborn and Clore, "Modeling the three-dimensional structure of the monocyte chemo-attractant and activating protein MCAF/MCP-1 on the basis of the solution structure of interleukin-8," *Protein Eng*, 4(3):263-269 (1991).
Hieshima et al., "Molecular cloning of a novel human CC chemokine liver and activation-regulated chemokine (LARC) expressed in liver. Chemotactic activity for lymphocytes and gene localization on chromosome 2," *J Biol Chem*, 272(9):5846-5853 (1997).
Hillier et al., *EMBL Database*, Entry HS519338, Accession No. WO5519 (1996).
Hillier et al., *EMBL Database*, Entry HS958307, Accession No. B73958 (1996).
Horuk et al., "The Duffy antigen receptor for chemokines: structural analysis and expression in the brain," *J Leukoc Biol*, 59(1):29-38 (1996).
Horuk, "Molecular properties of the chemokine receptor family," *Trends Pharmacol Sci*, 15(5):159-165 (1994).
Horuk, "The interleukin-8-receptor family: from chemokines to malaria," *Immunol Today*, 15(4):169-174 (1994).
Kelvin et al., "Chemokines and serpentines: the molecular biology of chemokine receptors," *J Leukoc Biol*, 54(6):604-612 (1993).
Lodi et al., "High-resolution structure of the β chemokine hMIP-1β by multidimensional NMR," *Science*, 263(5154):1762-1767 (1994).
Matsushima and Oppenheim, "Interleukin 8 and MCAF: novel inflammatory cytokines inducible by IL 1 and TNF," *Cytokine*, 1(1)2-13 (1989).
Miller and Krangel, "The human cytokine 1-309 is a monocyte chemoattractant," *Proc Natl Acad Sci USA*, 89(7):2950-2954 (1992).
Murdoch and Finn, "Chemokine receptors and their role in inflammation and infectious diseases," *Blood*, 95(10):3032-3043 (2000).

(Continued)

*Primary Examiner*—Elizabeth C. Kemmerer

(57) ABSTRACT

Novel chemokines from mammals, reagents related thereto including purified proteins, specific antibodies, and nucleic acids encoding said chemokines. Chemokine receptors are also provided. Methods of using said reagents and diagnostic kits are also provided.

7 Claims, 1 Drawing Sheet

OTHER PUBLICATIONS

Ngo et al., *The protein folding problem and tertiary structure prediction*, Merz et al. eds., Birkhasuer, Boston, pp. 491-495 (1994).

Nguyen et al., *EMBL Database*, Entry MMW6161, Accession No. W91616, (1996).

Oppenheim et al., "Properties of the novel proinflammatory supergene 'intercrine' cytokine family," *Annu Rev Immunol*, 9:617-648 (1991).

Proost et al., "Human monocyte chemotactic proteins-2 and -3: structural and functional comparison with MCP-1," *J Leukoc Biol*, 59(1):67-74 (1996).

Raport et al., "New members of the chemokine receptor gene family," *J Leukoc Biol*, 59(1):18-23 (1996).

Rossi et al., "Identification through bioinformatics of two new macrophage proinflammatory human chemokines: MIP-3α and MIP-3β," *J Immunol*, 158(3):1033-1036 (1997).

Rossi and Zlotnik, *EMBL Database*, Entry HSU77035, Accession No. U77035 (1997).

Samson et al., "Molecular cloning and functional expression of a new human CC-chemokine receptor gene," *Biochemistry*, 35(11):3362-3367 (1996).

Schall, "The chemokines," *The Cytokine Handbook*, 2$^{nd}$ ed., Academic Press Ltd., NY, pp. 419-460 (1994).

Schall, "Biology of the RANTES/SIS cytokine family," *Cytokine*, 3(3):165-183 (1991).

Schall and Bacon, "Chemokines, leukocyte trafficking, and inflammation," *Curr Opin Immunol*, 6(6):865-873 (1994).

Schall et al., "Receptor/ligand interactions in the C-C chemokine family," *The Chemokines*, Plenum Press, NY, pp. 29-37 (1993).

Skolnick and Fetrow, "From genes to protein structure and function: novel applications of computational approaches in the genomic era," *Trends Biotechnol*, 18(1):34-39 (2000).

Smith and Zhang, "The challenges of genome sequence annotation or 'the devil is in the details'," *Nat Biotechnol*, 15(12):1222-1223 (1997).

Stoeckle and Barker, "Two burgeoning families of platelet factor 4-related proteins: mediators of the inflammatory response," *New Biol*, 2(4):313-323 (1990).

Strieter and Kunkel, "Acute lung injury: the role of cytokines in the elicitation of neutrophils," *J Investig Med*, 42(4):640-651 (1994).

Strieter et al., "Role of C-X-C chemokines as regulators of angiogenesis in lung cancer," *J Leukoc Biol*, 57(5):752-762 (1995).

Vicari et al., "TECK: a novel CC chemokine associated with T cell development," *J Allergy Clin Immunol*, 99(1) part 2:S246, Abstract 1003 (1997).

Vicari et al., "TECK: a novel CC chemokine specifically expressed by thymic dendritic cells and potentially involved in T-cell development," *Immunity*, 7(2):291-301 (1997).

Rossi, D.L., Vicari, A.P., Franz-Bacon, K., McClanahan, T.K. and Zlotnik, A., *EMBL Database*, Entry HSU77180, Accession No. U77180 (1997).

Wells, "Additivity of mutational effects in proteins," *Biochemistry*, 29(37):8509-8517(1990).

Wenzel and Abboud, "Chemokines and renal disease," *Am J Kidney Dis*, 26(6):982-994 (1995).

Yoshida et al., "Molecular cloning of a novel human CC chemokine EBI1-ligand chemokine that is a specific functional ligand for EBI1, CCR7," *J Biol Chem*, 272(21):13803-13809 (1997).

Yoshie et al., "Novel lymphocyte-specific CC chemokines and their receptors," *J Leukoc Biol*, 62(5):634-644 (1997).

Zaballos et al., "Molecular cloning and RNA expression of two new human chemokine receptor-like genes," *Biochem Biophys Res Commun*, 227(3):846-853 (1996).

SEQUENCE LISTING

<160> NUMBER OF SEQ ID NOS: 26

<210> SEQ ID NO 1
<211> LENGTH: 1034
<212> TYPE: DNA
<213> ORGANISM: Murinae gen. sp.
<220> FEATURE:
<221> NAME/KEY: CDS
<222> LOCATION: (94)..(525)
<223> OTHER INFORMATION:

<400> SEQUENCE: 1

```
aggctacaag caggcaccag ctctcaggac cagaaaggca ttggtggccc ccttaaacct      60
tcaggtatct ggagaggaga tctaaccttc act atg aaa ctg tgg ctt ttt gcc     114
                                   Met Lys Leu Trp Leu Phe Ala
                                     1               5 tgc ctg gtt gcc tgt ttt gtt ggg gcc tgg atg ccg gtt gtc cat gcc     162
Cys Leu Val Ala Cys Phe Val Gly Ala Trp Met Pro Val Val His Ala
         10                  15                  20 caa ggt gcc ttt gaa gac tgc tgc ctg ggt tac cag cac agg atc aaa     210
Gln Gly Ala Phe Glu Asp Cys Cys Leu Gly Tyr Gln His Arg Ile Lys
     25                  30                  35 tgg aat gtt ctc cgg cat gct agg aat tat cac cag cag gaa gtg agt     258
Trp Asn Val Leu Arg His Ala Arg Asn Tyr His Gln Gln Glu Val Ser
 40                  45                  50                  55 gga agc tgc aac cta cgt gct gtg aga ttc tac ttc cgc cag aaa gta     306
Gly Ser Cys Asn Leu Arg Ala Val Arg Phe Tyr Phe Arg Gln Lys Val
                 60                  65                  70 gtg tgt ggg aat cca gag gac atg aat gtg aag agg gcg ata aga atc     354
Val Cys Gly Asn Pro Glu Asp Met Asn Val Lys Arg Ala Ile Arg Ile
             75                  80                  85 ttg aca gct agg aaa agg cta gtc cac tgg aag agc gcc tca gac tct     402
Leu Thr Ala Arg Lys Arg Leu Val His Trp Lys Ser Ala Ser Asp Ser
         90                  95                 100 cag act gaa agg aag aag tca aac cat atg aag tcc aag gtg gag aac     450
Gln Thr Glu Arg Lys Lys Ser Asn His Met Lys Ser Lys Val Glu Asn
    105                 110                 115 ccc aac agt aca agc gtg agg agt gcc acc cta ggt cat ccc agg atg     498
Pro Asn Ser Thr Ser Val Arg Ser Ala Thr Leu Gly His Pro Arg Met
120                 125                 130                 135 gtg atg atg ccc aga aag acc aac aat taagttaatt actcagagta           545
Val Met Met Pro Arg Lys Thr Asn Asn
                140 agcaccagct ggaggatggg cggagtctgc tgaagtgctg tcttctaggc atgccagtgc    605 caatgaactc actgaagcta cagtttcctg tacaagacca gacccaccaa cgtctcagca    665 tgtacgagga aggaactact gcgctaaagg ccctcccact caccaaggag ctattggcta    725 ttgatgattg ctgagggaag ggagtaattt tttttctctt tctgaagtgt gacttgagta    785 aattgcccat agttcagtat ataatcccca acctgtgctc aggcaagcaa ccctaattaa    845 atgcaatagc cacatacaaa agaagaggat atgaatagtt tggtaggagg ggcttgttag    905 gaagaagaca ttaacaggag agagggagc gagaggatag tgagtgtgtg agagtgcctg     965 cacgtgtgaa atggtcaaag aattaaaaaa taaaaactta aaaagctatt aaaagtaaa    1025 aaaaataaa                                                           1034
```

<210> SEQ ID NO 2
<211> LENGTH: 144

```
<212> TYPE: PRT
<213> ORGANISM: Murinae gen. sp.

<400> SEQUENCE: 2

Met Lys Leu Trp Leu Phe Ala Cys Leu Val Ala Cys Phe Val Gly Ala
  1               5                  10                  15

Trp Met Pro Val Val His Ala Gln Gly Ala Phe Glu Asp Cys Cys Leu
             20                  25                  30

Gly Tyr Gln His Arg Ile Lys Trp Asn Val Leu Arg His Ala Arg Asn
         35                  40                  45

Tyr His Gln Gln Glu Val Ser Gly Ser Cys Asn Leu Arg Ala Val Arg
     50                  55                  60

Phe Tyr Phe Arg Gln Lys Val Val Cys Gly Asn Pro Glu Asp Met Asn
 65                  70                  75                  80

Val Lys Arg Ala Ile Arg Ile Leu Thr Ala Arg Lys Arg Leu Val His
                 85                  90                  95

Trp Lys Ser Ala Ser Asp Ser Gln Thr Glu Arg Lys Lys Ser Asn His
            100                 105                 110

Met Lys Ser Lys Val Glu Asn Pro Asn Ser Thr Ser Val Arg Ser Ala
            115                 120                 125

Thr Leu Gly His Pro Arg Met Val Met Met Pro Arg Lys Thr Asn Asn
        130                 135                 140

<210> SEQ ID NO 3
<211> LENGTH: 1012
<212> TYPE: DNA
<213> ORGANISM: Homo sapiens
<220> FEATURE:
<221> NAME/KEY: CDS
<222> LOCATION: (117)..(566)
<223> OTHER INFORMATION:
<220> FEATURE:
<221> NAME/KEY: mat_peptide
<222> LOCATION: (186)..()
<223> OTHER INFORMATION:

<400> SEQUENCE: 3
```

| | |
|---|---|
| tcgacccacg cgtccgcttg gcctacagcc cggcgggcat cagctcccctt gacccagtgg | 60 |
| atatcggtgg ccccgttatt cgtccaggtg cccagggagg aggacccgcc tgcagc atg<br>                                                                                                                                                                                                         Met | 119 |

```
aac ctg tgg ctc ctg gcc tgc ctg gtg gcc ggc ttc ctg gga gcc tgg        167
Asn Leu Trp Leu Leu Ala Cys Leu Val Ala Gly Phe Leu Gly Ala Trp
    -20                 -15                 -10 gcc ccc gct gtc cac acc caa ggt gtc ttt gag gac tgc tgc ctg gcc        215
Ala Pro Ala Val His Thr Gln Gly Val Phe Glu Asp Cys Cys Leu Ala
 -5                  -1   1               5                  10 tac cac tac ccc att ggg tgg gct gtg ctc cgg cgc gcc tgg act tac        263
Tyr His Tyr Pro Ile Gly Trp Ala Val Leu Arg Arg Ala Trp Thr Tyr
                 15                  20                  25 cgg atc cag gag gtg agc ggg agc tgc aat ctg cct gct gcg ata ttc        311
Arg Ile Gln Glu Val Ser Gly Ser Cys Asn Leu Pro Ala Ala Ile Phe
             30                  35                  40 tac ctc ccc aag aga cac agg aag gtg tgt ggg aac ccc aaa agc agg        359
Tyr Leu Pro Lys Arg His Arg Lys Val Cys Gly Asn Pro Lys Ser Arg
         45                  50                  55 gag gtg cag aga gcc atg aag ctc ctg gat gct cga aat aag gtt ttt        407
Glu Val Gln Arg Ala Met Lys Leu Leu Asp Ala Arg Asn Lys Val Phe
     60                  65                  70 gca aag ctc cac cac aac atg cag acc ttc caa gca ggc cct cat gct        455
Ala Lys Leu His His Asn Met Gln Thr Phe Gln Ala Gly Pro His Ala
```

-continued

```
                75                  80                  85                  90
gta aag aag ttg agt tct gga aac tcc aag tta tca tca tcc aag ttt      503
Val Lys Lys Leu Ser Ser Gly Asn Ser Lys Leu Ser Ser Ser Lys Phe
                    95                 100                 105 agc aat ccc atc agc agc agc aag agg aat gtc tcc ctc ctg ata tca      551
Ser Asn Pro Ile Ser Ser Ser Lys Arg Asn Val Ser Leu Leu Ile Ser
            110                 115                 120 gct aat tca gga ctg tgagccggct catttctggg ctccatcggc acaggagggg      606
Ala Asn Ser Gly Leu
            125 ccggatctttc ctccgataaa accgtcgccc tacagaccca gctgtcccca cgcctctgtc    666
ttttgggtca agtcttaatc cctgcacctg agttggtcct ccctctgcac ccccaccacc    726
tcctgcccgt ctggcaactg aaagaagga gttggcctga ttttaacctt ttgccgctcc     786
ggggaacagc acaatcctgg gcagccagtg gctcttgtag agaaaactta ggatacctct    846
ctcactttct gtttcttgcc gtccaccccg ggccatgcca gtgtgtcctc tgggtccccct   906 ccaaaaatct ggtcattcaa ggatccccctc ccaaggctat gcttttctat aacttttaaa   966
taaaccttgg ggggtgaatg aataaaaaaa aaaaaaaaa aaaaaa                     1012
```

<210> SEQ ID NO 4
<211> LENGTH: 150
<212> TYPE: PRT
<213> ORGANISM: Homo sapiens

<400> SEQUENCE: 4

```
Met Asn Leu Trp Leu Leu Ala Cys Leu Val Ala Gly Phe Leu Gly Ala
            -20                 -15                 -10

Trp Ala Pro Ala Val His Thr Gln Gly Val Phe Glu Asp Cys Cys Leu
        -5                   -1  1                   5

Ala Tyr His Tyr Pro Ile Gly Trp Ala Val Leu Arg Arg Ala Trp Thr
10                  15                  20                  25

Tyr Arg Ile Gln Glu Val Ser Gly Ser Cys Asn Leu Pro Ala Ala Ile
                30                  35                  40

Phe Tyr Leu Pro Lys Arg His Arg Lys Val Cys Gly Asn Pro Lys Ser
            45                  50                  55

Arg Glu Val Gln Arg Ala Met Lys Leu Leu Asp Ala Arg Asn Lys Val
        60                  65                  70

Phe Ala Lys Leu His His Asn Met Gln Thr Phe Gln Ala Gly Pro His
    75                  80                  85

Ala Val Lys Lys Leu Ser Ser Gly Asn Ser Lys Leu Ser Ser Ser Lys
90                  95                 100                 105

Phe Ser Asn Pro Ile Ser Ser Ser Lys Arg Asn Val Ser Leu Leu Ile
                110                 115                 120

Ser Ala Asn Ser Gly Leu
            125
```

<210> SEQ ID NO 5
<211> LENGTH: 801
<212> TYPE: DNA
<213> ORGANISM: Homo sapiens
<220> FEATURE:
<221> NAME/KEY: CDS
<222> LOCATION: (1)..(288)
<223> OTHER INFORMATION:
<220> FEATURE:
<221> NAME/KEY: mat_peptide
<222> LOCATION: (79)..()
<223> OTHER INFORMATION:

<400> SEQUENCE: 5

```
atg tgc tgt acc aag agt ttg ctc ctg gct gct ttg atg tca gtg ctg      48
Met Cys Cys Thr Lys Ser Leu Leu Leu Ala Ala Leu Met Ser Val Leu
    -25             -20                 -15 cta ctc cac ctc tgc ggc gaa tca gaa gca gca agc aac ttt gac tgc      96
Leu Leu His Leu Cys Gly Glu Ser Glu Ala Ala Ser Asn Phe Asp Cys
-10              -5                  -1  1               5 tgt ctt gga tac aca gac cgt att ctt cat cct aaa ttt att gtg ggc     144
Cys Leu Gly Tyr Thr Asp Arg Ile Leu His Pro Lys Phe Ile Val Gly
            10                  15                  20 ttc aca cgg cag ctg gcc aat gaa ggc tgt gac atc aat gct atc atc     192
Phe Thr Arg Gln Leu Ala Asn Glu Gly Cys Asp Ile Asn Ala Ile Ile
        25                  30                  35 ttt cac aca aag aaa aag ttg tct gtg tgc gca aat cca aaa cag act     240
Phe His Thr Lys Lys Lys Leu Ser Val Cys Ala Asn Pro Lys Gln Thr
    40                  45                  50 tgg gtg aaa tat att gtg cgt ctc ctc agt aaa aaa gtc aag aac atg     288
Trp Val Lys Tyr Ile Val Arg Leu Leu Ser Lys Lys Val Lys Asn Met
55                  60                  65                  70 taaaaactgt ggcttttctg gaatggaatt ggacatagcc caagaacaga agaaccttg    348 ctggggttgg aggtttcact tgcacatcat ggagggttta gtgcttatct aatttgtgcc   408
tcactggact tgtccaatta atgaagttga ttcatattgc atcatagttt gctttgttta   468
agcatcacat taaagttaaa ctgtatttta tgttatttat agctgtaggt tttctgtgtt   528
tagctattta atactaattt tccataagct attttggttt agtgcaaagt ataaaattat   588
atttgggggg gaataagatt atatggactt ttttgcaagc aacaagctat ttttaaaaa    648 aaactattta acattctttt gtttatattg ttttgtctcc taaattgttg taattgcatt   708
ataaaataag aaaatatta ataagacaaa tattgaaaat aaagaaacaa aaagttaaaa    768
aaaaaaaaaa aaaaaaaaa aaaaaaaaaa aaa                                 801
```

<210> SEQ ID NO 6
<211> LENGTH: 96
<212> TYPE: PRT
<213> ORGANISM: Homo sapiens

<400> SEQUENCE: 6

```
Met Cys Cys Thr Lys Ser Leu Leu Leu Ala Ala Leu Met Ser Val Leu
    -25             -20                 -15

Leu Leu His Leu Cys Gly Glu Ser Glu Ala Ala Ser Asn Phe Asp Cys
-10              -5                  -1  1               5

Cys Leu Gly Tyr Thr Asp Arg Ile Leu His Pro Lys Phe Ile Val Gly
            10                  15                  20

Phe Thr Arg Gln Leu Ala Asn Glu Gly Cys Asp Ile Asn Ala Ile Ile
        25                  30                  35

Phe His Thr Lys Lys Lys Leu Ser Val Cys Ala Asn Pro Lys Gln Thr
    40                  45                  50

Trp Val Lys Tyr Ile Val Arg Leu Leu Ser Lys Lys Val Lys Asn Met
55                  60                  65                  70
```

<210> SEQ ID NO 7
<211> LENGTH: 699
<212> TYPE: DNA
<213> ORGANISM: Homo sapiens
<220> FEATURE:
<221> NAME/KEY: CDS
<222> LOCATION: (142)..(435)

-continued

<223> OTHER INFORMATION:

<400> SEQUENCE: 7

```
ggcacgagcg gcacgagcat cactcacacc ttgcatttca ccctgcatc ccagtcgccc      60 tgcagcctca cacagatcct gcacacaccc agacagctgg cgctcacaca ttcaccgttg    120
gcctgcctct gttcaccctc c atg gcc ctg cta ctg gcc ctc agc ctg ctg     171
                         Met Ala Leu Leu Leu Ala Leu Ser Leu Leu
                          1               5                  10 gtt ctc tgg act tcc cca gcc cca act ctg agt ggc acc aat gat gct     219
Val Leu Trp Thr Ser Pro Ala Pro Thr Leu Ser Gly Thr Asn Asp Ala
             15                  20                  25 gaa gac tgc tgc ctg tct gtg acc cag aaa ccc atc cct ggg tac atc     267
Glu Asp Cys Cys Leu Ser Val Thr Gln Lys Pro Ile Pro Gly Tyr Ile
             30                  35                  40 gtg agg aac ttc cac tac ctt ctc atc aag gat ggc tgc agg gtg cct     315
Val Arg Asn Phe His Tyr Leu Leu Ile Lys Asp Gly Cys Arg Val Pro
             45                  50                  55 gct gta gtg ttc acc aca ctg agg ggc cgc cag ctc tgt gca ccc cca     363
Ala Val Val Phe Thr Thr Leu Arg Gly Arg Gln Leu Cys Ala Pro Pro
 60                  65                  70 gac cag ccc tgg gta gaa cgc atc atc cag aga ctg cag agg acc tca     411
Asp Gln Pro Trp Val Glu Arg Ile Ile Gln Arg Leu Gln Arg Thr Ser
 75                  80                  85                  90 gcc aag atg aag cgc cgc agc agt taacctatga ccgtgcagag ggagcccgga    465
Ala Lys Met Lys Arg Arg Ser Ser
                 95 gtccgagtca agcattgtga attattacct aacctgggga accgaggacc agaaggaagg    525 accaggcttc cagctcctct gcaccagacc tgaccagcca ggacagggcc tggggtgtgt    585 gtgagtgtga gtgtgagcga gagggtgagt gtggtctaga gtaaagctgc tccacccca    645 gattgcaatg ctaccaataa agccgcctgg tgtttacaac taaaaaaaaa aaaa           699
```

<210> SEQ ID NO 8
<211> LENGTH: 98
<212> TYPE: PRT
<213> ORGANISM: Homo sapiens

<400> SEQUENCE: 8

```
Met Ala Leu Leu Leu Ala Leu Ser Leu Leu Val Leu Trp Thr Ser Pro
 1               5                  10                  15

Ala Pro Thr Leu Ser Gly Thr Asn Asp Ala Glu Asp Cys Cys Leu Ser
             20                  25                  30

Val Thr Gln Lys Pro Ile Pro Gly Tyr Ile Val Arg Asn Phe His Tyr
         35                  40                  45

Leu Leu Ile Lys Asp Gly Cys Arg Val Pro Ala Val Val Phe Thr Thr
     50                  55                  60

Leu Arg Gly Arg Gln Leu Cys Ala Pro Pro Asp Gln Pro Trp Val Glu
 65                  70                  75                  80

Arg Ile Ile Gln Arg Leu Gln Arg Thr Ser Ala Lys Met Lys Arg Arg
                 85                  90                  95

Ser Ser
```

<210> SEQ ID NO 9
<211> LENGTH: 1119
<212> TYPE: DNA
<213> ORGANISM: Homo sapiens
<220> FEATURE:
<221> NAME/KEY: CDS

<222> LOCATION: (1)..(1095)
<223> OTHER INFORMATION:

<400> SEQUENCE: 9

| | | | | | | | | | | | | | | | | |
|---|---|---|---|---|---|---|---|---|---|---|---|---|---|---|---|---|
| atg | ttt | tcg | act | cca | gtg | aag | att | att | ttg | tgt | cag | tca | ata | ctt | cat | 48 |
| Met | Phe | Ser | Thr | Pro | Val | Lys | Ile | Ile | Leu | Cys | Gln | Ser | Ile | Leu | His | |
| 1 | | | | 5 | | | | | 10 | | | | | 15 | | |
| att | act | cag | ttg | att | ctg | aga | tgt | tac | tgt | gct | cct | tgc | agg | agg | tca | 96 |
| Ile | Thr | Gln | Leu | Ile | Leu | Arg | Cys | Tyr | Cys | Ala | Pro | Cys | Arg | Arg | Ser | |
| | | | 20 | | | | | 25 | | | | | 30 | | | |
| ggc | agt | tct | cca | ggc | tat | ttg | tac | cga | att | gcc | tac | tcc | ttg | atc | tgt | 144 |
| Gly | Ser | Ser | Pro | Gly | Tyr | Leu | Tyr | Arg | Ile | Ala | Tyr | Ser | Leu | Ile | Cys | |
| | | 35 | | | | | 40 | | | | | 45 | | | | |
| gtt | ctt | ggc | ctc | ctg | ggg | aat | att | ctg | gtg | gtg | atc | acc | ttt | gct | ttt | 192 |
| Val | Leu | Gly | Leu | Leu | Gly | Asn | Ile | Leu | Val | Val | Ile | Thr | Phe | Ala | Phe | |
| 50 | | | | | 55 | | | | | 60 | | | | | | |
| tat | aag | aag | gcc | agg | tct | atg | aca | gac | gtc | tat | ctc | ttg | aac | atg | gcc | 240 |
| Tyr | Lys | Lys | Ala | Arg | Ser | Met | Thr | Asp | Val | Tyr | Leu | Leu | Asn | Met | Ala | |
| 65 | | | | | 70 | | | | | 75 | | | | | 80 | |
| att | gca | gac | atc | ctc | ttt | gtt | ctt | act | ctc | cca | ttc | tgg | gca | gtg | agt | 288 |
| Ile | Ala | Asp | Ile | Leu | Phe | Val | Leu | Thr | Leu | Pro | Phe | Trp | Ala | Val | Ser | |
| | | | | 85 | | | | | 90 | | | | | 95 | | |
| cat | gcc | act | ggt | gcg | tgg | gtt | ttc | agc | aat | gcc | acg | tgc | aag | ttg | cta | 336 |
| His | Ala | Thr | Gly | Ala | Trp | Val | Phe | Ser | Asn | Ala | Thr | Cys | Lys | Leu | Leu | |
| | | | 100 | | | | | 105 | | | | | 110 | | | |
| aaa | ggc | atc | tat | gcc | atc | aac | ttt | aac | tgc | ggg | atg | ctg | ctc | ctg | act | 384 |
| Lys | Gly | Ile | Tyr | Ala | Ile | Asn | Phe | Asn | Cys | Gly | Met | Leu | Leu | Leu | Thr | |
| | | 115 | | | | | 120 | | | | | 125 | | | | |
| tgc | att | agc | atg | gac | cgg | tac | atc | gcc | att | gta | cag | gcg | act | aag | tca | 432 |
| Cys | Ile | Ser | Met | Asp | Arg | Tyr | Ile | Ala | Ile | Val | Gln | Ala | Thr | Lys | Ser | |
| | 130 | | | | | 135 | | | | | 140 | | | | | |
| ttc | cgg | ctc | cga | tcc | aga | aca | cta | ccg | cgc | agc | aaa | atc | atc | tgc | ctt | 480 |
| Phe | Arg | Leu | Arg | Ser | Arg | Thr | Leu | Pro | Arg | Ser | Lys | Ile | Ile | Cys | Leu | |
| 145 | | | | | 150 | | | | | 155 | | | | | 160 | |
| gtt | gtg | tgg | ggg | ctg | tca | gtc | atc | atc | tcc | agc | tca | act | ttt | gtc | ttc | 528 |
| Val | Val | Trp | Gly | Leu | Ser | Val | Ile | Ile | Ser | Ser | Ser | Thr | Phe | Val | Phe | |
| | | | | 165 | | | | | 170 | | | | | 175 | | |
| aac | caa | aaa | tac | aac | acc | caa | ggc | agc | gat | gtc | tgt | gaa | ccc | aag | tac | 576 |
| Asn | Gln | Lys | Tyr | Asn | Thr | Gln | Gly | Ser | Asp | Val | Cys | Glu | Pro | Lys | Tyr | |
| | | | 180 | | | | | 185 | | | | | 190 | | | |
| caa | act | gtc | tcg | gag | ccc | atc | agg | tgg | aag | ctg | ctg | atg | ttg | ggg | ctt | 624 |
| Gln | Thr | Val | Ser | Glu | Pro | Ile | Arg | Trp | Lys | Leu | Leu | Met | Leu | Gly | Leu | |
| | | 195 | | | | | 200 | | | | | 205 | | | | |
| gag | cta | ctc | ttt | ggt | ttc | ttt | atc | cct | ttg | atg | ttc | atg | ata | ttt | tgt | 672 |
| Glu | Leu | Leu | Phe | Gly | Phe | Phe | Ile | Pro | Leu | Met | Phe | Met | Ile | Phe | Cys | |
| | 210 | | | | | 215 | | | | | 220 | | | | | |
| tac | acg | ttc | att | gtc | aaa | acc | ttg | gtg | caa | gct | cag | aat | tct | aaa | agg | 720 |
| Tyr | Thr | Phe | Ile | Val | Lys | Thr | Leu | Val | Gln | Ala | Gln | Asn | Ser | Lys | Arg | |
| 225 | | | | | 230 | | | | | 235 | | | | | 240 | |
| cac | aaa | gcc | atc | cgt | gta | atc | ata | gct | gtg | gtg | ctt | gtg | ttt | ctg | gct | 768 |
| His | Lys | Ala | Ile | Arg | Val | Ile | Ile | Ala | Val | Val | Leu | Val | Phe | Leu | Ala | |
| | | | | 245 | | | | | 250 | | | | | 255 | | |
| tgt | cag | att | cct | cat | aac | atg | gtc | ctg | ctt | gtg | acg | gct | gct | aat | ttg | 816 |
| Cys | Gln | Ile | Pro | His | Asn | Met | Val | Leu | Leu | Val | Thr | Ala | Ala | Asn | Leu | |
| | | | 260 | | | | | 265 | | | | | 270 | | | |
| ggt | aaa | atg | aac | cga | tcc | tgc | cag | agc | gaa | aag | cta | att | ggc | tat | acg | 864 |
| Gly | Lys | Met | Asn | Arg | Ser | Cys | Gln | Ser | Glu | Lys | Leu | Ile | Gly | Tyr | Thr | |
| | | 275 | | | | | 280 | | | | | 285 | | | | |
| aaa | act | gtc | aca | gaa | gtc | ctg | gct | ttc | ctg | cac | tgc | tgc | ctg | aac | cct | 912 |
| Lys | Thr | Val | Thr | Glu | Val | Leu | Ala | Phe | Leu | His | Cys | Cys | Leu | Asn | Pro | |

```
                290               295                300
gtg ctc tac gct ttt att ggg cag aag ttc aga aac tac ttt ctg aag    960
Val Leu Tyr Ala Phe Ile Gly Gln Lys Phe Arg Asn Tyr Phe Leu Lys
305                 310                 315                 320 atc ttg aag gac ctg tgg tgt gtg aga agg aag tac aag tcc tca ggc   1008
Ile Leu Lys Asp Leu Trp Cys Val Arg Arg Lys Tyr Lys Ser Ser Gly
                325                 330                 335 ttc tcc tgt gcc ggg agg tac tca gaa aac att tct cgg cag acc agt   1056
Phe Ser Cys Ala Gly Arg Tyr Ser Glu Asn Ile Ser Arg Gln Thr Ser
            340                 345                 350 gag acc gca gat aac gac aat gcg tcg tcc ttc act atg tgatagaaag    1105
Glu Thr Ala Asp Asn Asp Asn Ala Ser Ser Phe Thr Met
                355                 360             365 ctgagtctcc ctaa                                                   1119

<210> SEQ ID NO 10
<211> LENGTH: 365
<212> TYPE: PRT
<213> ORGANISM: Homo sapiens

<400> SEQUENCE: 10

Met Phe Ser Thr Pro Val Lys Ile Ile Leu Cys Gln Ser Ile Leu His
1               5                   10                  15

Ile Thr Gln Leu Ile Leu Arg Cys Tyr Cys Ala Pro Cys Arg Arg Ser
            20                  25                  30

Gly Ser Ser Pro Gly Tyr Leu Tyr Arg Ile Ala Tyr Ser Leu Ile Cys
        35                  40                  45

Val Leu Gly Leu Leu Gly Asn Ile Leu Val Val Ile Thr Phe Ala Phe
    50                  55                  60

Tyr Lys Lys Ala Arg Ser Met Thr Asp Val Tyr Leu Leu Asn Met Ala
65                  70                  75                  80

Ile Ala Asp Ile Leu Phe Val Leu Thr Leu Pro Phe Trp Ala Val Ser
                85                  90                  95

His Ala Thr Gly Ala Trp Val Phe Ser Asn Ala Thr Cys Lys Leu Leu
            100                 105                 110

Lys Gly Ile Tyr Ala Ile Asn Phe Asn Cys Gly Met Leu Leu Leu Thr
        115                 120                 125

Cys Ile Ser Met Asp Arg Tyr Ile Ala Ile Val Gln Ala Thr Lys Ser
    130                 135                 140

Phe Arg Leu Arg Ser Arg Thr Leu Pro Arg Ser Lys Ile Ile Cys Leu
145                 150                 155                 160

Val Val Trp Gly Leu Ser Val Ile Ser Ser Ser Thr Phe Val Phe
                165                 170                 175

Asn Gln Lys Tyr Asn Thr Gln Gly Ser Asp Val Cys Glu Pro Lys Tyr
            180                 185                 190

Gln Thr Val Ser Glu Pro Ile Arg Trp Lys Leu Leu Met Leu Gly Leu
        195                 200                 205

Glu Leu Leu Phe Gly Phe Phe Ile Pro Leu Met Phe Met Ile Phe Cys
    210                 215                 220

Tyr Thr Phe Ile Val Lys Thr Leu Val Gln Ala Gln Asn Ser Lys Arg
225                 230                 235                 240

His Lys Ala Ile Arg Val Ile Ile Ala Val Val Leu Val Phe Leu Ala
                245                 250                 255

Cys Gln Ile Pro His Asn Met Val Leu Leu Val Thr Ala Ala Asn Leu
            260                 265                 270
```

```
        Gly Lys Met Asn Arg Ser Cys Gln Ser Glu Lys Leu Ile Gly Tyr Thr
                    275                 280                 285

Lys Thr Val Thr Glu Val Leu Ala Phe Leu His Cys Cys Leu Asn Pro
            290                 295                 300

Val Leu Tyr Ala Phe Ile Gly Gln Lys Phe Arg Asn Tyr Phe Leu Lys
        305                 310                 315                 320

Ile Leu Lys Asp Leu Trp Cys Val Arg Arg Lys Tyr Lys Ser Ser Gly
                        325                 330                 335

Phe Ser Cys Ala Gly Arg Tyr Ser Glu Asn Ile Ser Arg Gln Thr Ser
                    340                 345                 350

Glu Thr Ala Asp Asn Asp Asn Ala Ser Ser Phe Thr Met
                355                 360                 365

<210> SEQ ID NO 11
<211> LENGTH: 1547
<212> TYPE: DNA
<213> ORGANISM: Homo sapiens
<220> FEATURE:
<221> NAME/KEY: CDS
<222> LOCATION: (49)..(1116)
<223> OTHER INFORMATION:

<400> SEQUENCE: 11
```

| | | |
|---|---|---|
| gaggaagctg cttcgggggg tgagcaaact ttttaaaatg cagaaatt atg atc tac | | 57 |
| Met Ile Tyr | | |
| 1 | | |

```
acc cgt ttc tta aaa ggc agt ctg aag atg gcc aat tac acg ctg gca      105
Thr Arg Phe Leu Lys Gly Ser Leu Lys Met Ala Asn Tyr Thr Leu Ala
    5                  10                  15 cca gag gat gaa tat gat gtc ctc ata gaa ggt gaa ctg gag agc gat      153
Pro Glu Asp Glu Tyr Asp Val Leu Ile Glu Gly Glu Leu Glu Ser Asp
20                  25                  30                  35 gag gca gag caa tgt gac aag tat gac gcc cag gca ctc tca gcc cag      201
Glu Ala Glu Gln Cys Asp Lys Tyr Asp Ala Gln Ala Leu Ser Ala Gln
                40                  45                  50 ctg gtg cca tca ctc tgc tct gct gtg ttt gtg atc ggt gtc ctg gac      249
Leu Val Pro Ser Leu Cys Ser Ala Val Phe Val Ile Gly Val Leu Asp
            55                  60                  65 aat ctc ctg gtt gtg ctt atc ctg gta aaa tat aaa gga ctc aaa cgc      297
Asn Leu Leu Val Val Leu Ile Leu Val Lys Tyr Lys Gly Leu Lys Arg
        70                  75                  80 gtg gaa aat atc tat ctt cta aac ttg gca gtt tct aac ttg tgt ttc      345
Val Glu Asn Ile Tyr Leu Leu Asn Leu Ala Val Ser Asn Leu Cys Phe
85                  90                  95 ttg ctt acc ctg ccc ttc tgg gct cat gct ggg ggc gat ccc atg tgt      393
Leu Leu Thr Leu Pro Phe Trp Ala His Ala Gly Gly Asp Pro Met Cys
100                 105                 110                 115 aaa att ctc att gga ctg tac ttc gtg ggc ctg tac agt gag aca ttt      441
Lys Ile Leu Ile Gly Leu Tyr Phe Val Gly Leu Tyr Ser Glu Thr Phe
                120                 125                 130 ttc aat tgc ctt ctg act gtg caa agg tac cta gtg ttt ttg cac aag      489
Phe Asn Cys Leu Leu Thr Val Gln Arg Tyr Leu Val Phe Leu His Lys
            135                 140                 145 ggc aac ttt ttc tca gcc agg agg agg gtg ccc tgt ggc atc att aca      537
Gly Asn Phe Phe Ser Ala Arg Arg Arg Val Pro Cys Gly Ile Ile Thr
        150                 155                 160 agt gtc ctg gca tgg gta aca gcc att ctg gcc act ttg cct gaa ttc      585
Ser Val Leu Ala Trp Val Thr Ala Ile Leu Ala Thr Leu Pro Glu Phe
165                 170                 175 gtg gtt tat aaa cct cag atg gaa gac cag aaa tac aag tgt gca ttt      633
```

```
Val Val Tyr Lys Pro Gln Met Glu Asp Gln Lys Tyr Lys Cys Ala Phe
180                 185                 190                 195 agc aga act ccc ttc ctg cca gct gat gag aca ttc tgg aag cat ttt        681
Ser Arg Thr Pro Phe Leu Pro Ala Asp Glu Thr Phe Trp Lys His Phe
                200                 205                 210 ctg act tta aaa atg aac att tcg gtt ctt gtc ctc ccc cta ttt att        729
Leu Thr Leu Lys Met Asn Ile Ser Val Leu Val Leu Pro Leu Phe Ile
                215                 220                 225 ttt aca ttt ctc tat gtg caa atg aga aaa aca cta agg ttc agg gag        777
Phe Thr Phe Leu Tyr Val Gln Met Arg Lys Thr Leu Arg Phe Arg Glu
            230                 235                 240 cag agg tat agc ctt ttc aag ctt gtt ttt gcc gta atg gta gtc ttc        825
Gln Arg Tyr Ser Leu Phe Lys Leu Val Phe Ala Val Met Val Val Phe
            245                 250                 255 ctt ctg atg tgg gcg ccc tac aat att gca ttt ttc ctg tcc act ttc        873
Leu Leu Met Trp Ala Pro Tyr Asn Ile Ala Phe Phe Leu Ser Thr Phe
260                 265                 270                 275 aaa gaa cac ttc tcc ctg agt gac tgc aag agc tac aat ctg gac            921
Lys Glu His Phe Ser Leu Ser Asp Cys Lys Ser Ser Tyr Asn Leu Asp
                280                 285                 290 aaa agt gtt cac atc act aaa ctc atc gcc acc acc cac tgc tgc atc        969
Lys Ser Val His Ile Thr Lys Leu Ile Ala Thr Thr His Cys Cys Ile
                295                 300                 305 aac cct ctc ctg tat gcg ttt ctt gat ggg aca ttt agc aaa tac ctc       1017
Asn Pro Leu Leu Tyr Ala Phe Leu Asp Gly Thr Phe Ser Lys Tyr Leu
                310                 315                 320 tgc cgc tgt ttc cat ctg cgt agt aac acc cca ctt caa ccc agg ggg       1065
Cys Arg Cys Phe His Leu Arg Ser Asn Thr Pro Leu Gln Pro Arg Gly
325                 330                 335 cag tct gca caa ggc aca tcg agg gaa gaa cct gac cat tcc acc gaa       1113
Gln Ser Ala Gln Gly Thr Ser Arg Glu Glu Pro Asp His Ser Thr Glu
340                 345                 350                 355 gtg taaactagca tccaccaaat gcaagaagaa taaacatgga ttttcatctt            1166
Val tctgcattat ttcatgtaaa ttttctacac atttgtatac aaaatcggat acaggaagaa     1226
aagggagagg tgagctaaca tttgctaagc actgaatttg tctcaggcac cgtgcaaggc     1286
tctttacaaa cgtgagctcc ttcgcctcct accacttgtc catagtgtgg ataggactag     1346
tctcatttct ctgagaagaa aactaaggcg cggaaatttg tctaagatca cataactagg     1406
aagtggcaga actgattctc cagccctggt agcatttgct cagagcctac gcttggtcca     1466
gaacatcaaa ctccaaaccc tgggacaaaa cgacatgaaa taaatgtatt ttaaaacata     1526
taaaaaaaaa aaaaaaaaa a                                                1547

<210> SEQ ID NO 12
<211> LENGTH: 356
<212> TYPE: PRT
<213> ORGANISM: Homo sapiens

<400> SEQUENCE: 12

Met Ile Tyr Thr Arg Phe Leu Lys Gly Ser Leu Lys Met Ala Asn Tyr
1               5                   10                  15

Thr Leu Ala Pro Glu Asp Glu Tyr Asp Val Leu Ile Glu Gly Glu Leu
                20                  25                  30

Glu Ser Asp Glu Ala Glu Gln Cys Asp Lys Tyr Asp Ala Gln Ala Leu
            35                  40                  45

Ser Ala Gln Leu Val Pro Ser Leu Cys Ser Ala Val Phe Val Ile Gly
50                  55                  60
```

```
Val Leu Asp Asn Leu Leu Val Leu Ile Leu Val Lys Tyr Lys Gly
 65                  70                  75                  80

Leu Lys Arg Val Glu Asn Ile Tyr Leu Leu Asn Leu Ala Val Ser Asn
                 85                  90                  95

Leu Cys Phe Leu Leu Thr Leu Pro Phe Trp Ala His Ala Gly Gly Asp
            100                 105                 110

Pro Met Cys Lys Ile Leu Ile Gly Leu Tyr Phe Val Gly Leu Tyr Ser
        115                 120                 125

Glu Thr Phe Phe Asn Cys Leu Leu Thr Val Gln Arg Tyr Leu Val Phe
    130                 135                 140

Leu His Lys Gly Asn Phe Phe Ser Ala Arg Arg Val Pro Cys Gly
145                 150                 155                 160

Ile Ile Thr Ser Val Leu Ala Trp Val Thr Ala Ile Leu Ala Thr Leu
                165                 170                 175

Pro Glu Phe Val Val Tyr Lys Pro Gln Met Glu Asp Gln Lys Tyr Lys
            180                 185                 190

Cys Ala Phe Ser Arg Thr Pro Phe Leu Pro Ala Asp Glu Thr Phe Trp
        195                 200                 205

Lys His Phe Leu Thr Leu Lys Met Asn Ile Ser Val Leu Val Leu Pro
    210                 215                 220

Leu Phe Ile Phe Thr Phe Leu Tyr Val Gln Met Arg Lys Thr Leu Arg
225                 230                 235                 240

Phe Arg Glu Gln Arg Tyr Ser Leu Phe Lys Leu Val Phe Ala Val Met
                245                 250                 255

Val Val Phe Leu Leu Met Trp Ala Pro Tyr Asn Ile Ala Phe Phe Leu
            260                 265                 270

Ser Thr Phe Lys Glu His Phe Ser Leu Ser Asp Cys Lys Ser Ser Tyr
        275                 280                 285

Asn Leu Asp Lys Ser Val His Ile Thr Lys Leu Ile Ala Thr Thr His
    290                 295                 300

Cys Cys Ile Asn Pro Leu Leu Tyr Ala Phe Leu Asp Gly Thr Phe Ser
305                 310                 315                 320

Lys Tyr Leu Cys Arg Cys Phe His Leu Arg Ser Asn Thr Pro Leu Gln
                325                 330                 335

Pro Arg Gly Gln Ser Ala Gln Gly Thr Ser Arg Glu Glu Pro Asp His
            340                 345                 350

Ser Thr Glu Val
        355

<210> SEQ ID NO 13
<211> LENGTH: 355
<212> TYPE: PRT
<213> ORGANISM: Homo sapiens

<400> SEQUENCE: 13

Met Glu Thr Pro Asn Thr Thr Glu Asp Tyr Asp Thr Thr Thr Glu Phe
  1               5                  10                  15

Asp Tyr Gly Asp Ala Thr Pro Cys Gln Lys Val Asn Glu Arg Ala Phe
             20                  25                  30

Gly Ala Gln Leu Leu Pro Pro Leu Tyr Ser Leu Val Phe Val Ile Gly
         35                  40                  45

Leu Val Gly Asn Ile Leu Val Val Leu Val Leu Val Gln Tyr Lys Arg
     50                  55                  60

Leu Lys Asn Met Thr Ser Ile Tyr Leu Leu Asn Leu Ala Ile Ser Asp
```

-continued

```
                65                  70                  75                  80
Leu Leu Phe Leu Phe Thr Leu Pro Phe Trp Ile Asp Tyr Lys Leu Lys
                        85                  90                  95

Asp Asp Trp Val Phe Gly Asp Ala Met Cys Lys Ile Leu Ser Gly Phe
                    100                 105                 110

Tyr Tyr Thr Gly Leu Tyr Ser Glu Ile Phe Phe Ile Leu Leu Thr
                115                 120                 125

Ile Asp Arg Tyr Leu Ala Ile Val His Ala Val Phe Ala Leu Arg Ala
            130                 135                 140

Arg Thr Val Thr Phe Gly Val Ile Thr Ser Ile Ile Trp Ala Leu
145                 150                 155                 160

Ala Ile Leu Ala Ser Met Pro Gly Leu Tyr Phe Ser Lys Thr Gln Trp
                    165                 170                 175

Glu Phe Thr His His Thr Cys Ser Leu His Phe Pro His Glu Ser Leu
                180                 185                 190

Arg Glu Trp Lys Leu Phe Gln Ala Leu Lys Leu Asn Leu Phe Gly Leu
                195                 200                 205

Val Leu Pro Leu Leu Val Met Ile Ile Cys Tyr Thr Gly Ile Ile Lys
            210                 215                 220

Ile Leu Leu Arg Arg Pro Asn Glu Lys Lys Ser Lys Ala Val Arg Leu
225                 230                 235                 240

Ile Phe Val Ile Met Ile Phe Phe Leu Phe Trp Thr Pro Tyr Asn
                    245                 250                 255

Leu Thr Ile Leu Ile Ser Val Phe Gln Asp Phe Leu Phe Thr His Glu
                260                 265                 270

Cys Glu Gln Ser Arg His Leu Asp Leu Ala Val Gln Val Thr Glu Val
                275                 280                 285

Ile Ala Tyr Thr His Cys Cys Val Asn Pro Val Ile Tyr Ala Phe Val
            290                 295                 300

Gly Glu Arg Phe Arg Lys Tyr Leu Arg Gln Leu Phe His Arg Arg Val
305                 310                 315                 320

Ala Val His Leu Val Lys Trp Leu Pro Phe Leu Ser Val Asp Arg Leu
                    325                 330                 335

Glu Arg Val Ser Ser Thr Ser Pro Ser Thr Gly Glu His Glu Leu Ser
                340                 345                 350

Ala Gly Phe
        355

<210> SEQ ID NO 14
<211> LENGTH: 374
<212> TYPE: PRT
<213> ORGANISM: Homo sapiens

<400> SEQUENCE: 14

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
                20                  25                  30

His Lys Phe Asp Val Lys Gln Ile Gly Ala Gln Leu Leu Pro Pro Leu
            35                  40                  45

Tyr Ser Leu Val Phe Ile Phe Gly Phe Val Gly Asn Met Leu Val Val
        50                  55                  60

Leu Ile Leu Ile Asn Cys Lys Lys Leu Lys Cys Leu Thr Asp Ile Tyr
65                  70                  75                  80
```

-continued

Leu Leu Asn Leu Ala Ile Ser Asp Leu Leu Phe Leu Ile Thr Leu Pro
                85                  90                  95

Leu Trp Ala His Ser Ala Ala Asn Glu Trp Val Phe Gly Asn Ala Met
            100                 105                 110

Cys Lys Leu Phe Thr Gly Leu Tyr His Ile Gly Tyr Phe Gly Gly Ile
        115                 120                 125

Phe Phe Ile Ile Leu Leu Thr Ile Asp Arg Tyr Leu Ala Ile Val His
130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
            180                 185                 190

Tyr Phe Pro Arg Gly Trp Asn Asn Phe His Thr Ile Met Arg Asn Ile
        195                 200                 205

Leu Gly Leu Val Leu Pro Leu Leu Ile Met Val Ile Cys Tyr Ser Gly
210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
            260                 265                 270

Gly Leu Ser Asn Cys Glu Ser Thr Ser Gln Leu Asp Gln Ala Thr Gln
        275                 280                 285

Val Thr Glu Thr Leu Gly Met Thr His Cys Cys Ile Asn Pro Ile Ile
290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
            340                 345                 350

Gly Arg Gly Lys Gly Lys Ser Ile Gly Arg Ala Pro Glu Ala Ser Leu
        355                 360                 365

Gln Asp Lys Glu Gly Ala
    370

<210> SEQ ID NO 15
<211> LENGTH: 355
<212> TYPE: PRT
<213> ORGANISM: Homo sapiens

<400> SEQUENCE: 15

Met Thr Thr Ser Leu Asp Thr Val Glu Thr Phe Gly Thr Thr Ser Tyr
1               5                   10                  15

Tyr Asp Asp Val Gly Leu Leu Cys Glu Lys Ala Asp Thr Arg Ala Leu
            20                  25                  30

Met Ala Gln Phe Val Pro Pro Leu Tyr Ser Leu Val Phe Thr Val Gly
        35                  40                  45

Leu Leu Gly Asn Val Val Val Met Ile Leu Ile Lys Tyr Arg Arg
    50                  55                  60

Leu Arg Ile Met Thr Asn Ile Tyr Leu Leu Asn Leu Ala Ile Ser Asp
65                  70                  75                  80

```
Leu Leu Phe Leu Val Thr Leu Pro Phe Trp Ile His Tyr Val Arg Gly
                85                  90                  95
His Asn Trp Val Phe Gly His Gly Met Cys Lys Leu Leu Ser Gly Phe
            100                 105                 110
Tyr His Thr Gly Leu Tyr Ser Glu Ile Phe Ile Ile Leu Leu Thr
        115                 120                 125
Ile Asp Arg Tyr Leu Ala Ile Val His Ala Val Phe Ala Leu Arg Ala
    130                 135                 140
Arg Thr Val Thr Phe Gly Val Ile Thr Ser Ile Val Thr Trp Gly Leu
145                 150                 155                 160
Ala Val Leu Ala Ala Leu Pro Glu Phe Ile Phe Tyr Glu Thr Glu Glu
                165                 170                 175
Leu Phe Glu Glu Thr Leu Cys Ser Ala Leu Tyr Pro Glu Asp Thr Val
            180                 185                 190
Tyr Ser Trp Arg His Phe His Thr Leu Arg Met Thr Ile Phe Cys Leu
        195                 200                 205
Val Leu Pro Leu Leu Val Met Ala Ile Cys Tyr Thr Gly Ile Ile Lys
    210                 215                 220
Thr Leu Leu Arg Cys Pro Ser Lys Lys Lys Tyr Lys Ala Ile Arg Leu
225                 230                 235                 240
Ile Phe Val Ile Met Ala Val Phe Phe Ile Phe Trp Thr Pro Tyr Asn
                245                 250                 255
Val Ala Ile Leu Leu Ser Ser Tyr Gln Ser Ile Leu Phe Gly Asn Asp
            260                 265                 270
Cys Glu Arg Ser Lys His Leu Asp Leu Val Met Leu Val Thr Glu Val
        275                 280                 285
Ile Ala Tyr Ser His Cys Cys Met Asn Pro Val Ile Tyr Ala Phe Val
    290                 295                 300
Gly Glu Arg Phe Arg Lys Tyr Leu Arg His Phe Phe His Arg His Leu
305                 310                 315                 320
Leu Met His Leu Gly Arg Tyr Ile Pro Phe Leu Pro Ser Glu Lys Leu
                325                 330                 335
Glu Arg Thr Ser Ser Val Ser Pro Ser Thr Ala Glu Pro Glu Leu Ser
            340                 345                 350
Ile Val Phe
        355

<210> SEQ ID NO 16
<211> LENGTH: 360
<212> TYPE: PRT
<213> ORGANISM: Homo sapiens

<400> SEQUENCE: 16

Met Asn Pro Thr Asp Ile Ala Asp Thr Thr Leu Asp Glu Ser Ile Tyr
1               5                   10                  15
Ser Asn Tyr Tyr Leu Tyr Glu Ser Ile Pro Lys Pro Cys Thr Lys Glu
                20                  25                  30
Gly Ile Lys Ala Phe Gly Glu Leu Phe Leu Pro Pro Leu Tyr Ser Leu
            35                  40                  45
Val Phe Val Phe Gly Leu Leu Gly Asn Ser Val Val Val Leu Val Leu
        50                  55                  60
Phe Lys Tyr Lys Arg Leu Arg Ser Met Thr Asp Val Tyr Leu Leu Asn
65                  70                  75                  80
Leu Ala Ile Ser Asp Leu Leu Phe Val Phe Ser Leu Pro Phe Trp Gly
```

```
                         85                  90                  95
Tyr Tyr Ala Ala Asp Gln Trp Val Phe Gly Leu Gly Leu Cys Lys Met
                100                 105                 110

Ile Ser Trp Met Tyr Leu Val Gly Phe Tyr Gly Ile Phe Phe Val
            115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
            195                 200                 205

Leu Gly Leu Val Ile Pro Leu Gly Ile Met Leu Phe Cys Tyr Ser Met
    210                 215                 220

Ile Ile Arg Thr Leu Gln His Cys Lys Asn Glu Lys Lys Asn Lys Ala
225                 230                 235                 240

Val Lys Met Ile Phe Ala Val Val Leu Phe Leu Gly Phe Trp Thr
                245                 250                 255

Pro Tyr Asn Ile Val Leu Phe Leu Glu Thr Leu Val Glu Leu Glu Val
                260                 265                 270

Leu Gln Asp Cys Thr Phe Glu Arg Tyr Leu Asp Tyr Ala Ile Gln Ala
                275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
                340                 345                 350

Asp His Asp Leu His Asp Ala Leu
        355                 360

<210> SEQ ID NO 17
<211> LENGTH: 23
<212> TYPE: DNA
<213> ORGANISM: Artificial Sequence
<220> FEATURE:
<223> OTHER INFORMATION: HPRT sense primer

<400> SEQUENCE: 17
gtaatgatca gtcaacgggg gac                                          23

<210> SEQ ID NO 18
<211> LENGTH: 24
<212> TYPE: DNA
<213> ORGANISM: Artificial Sequence
<220> FEATURE:
<223> OTHER INFORMATION: HPRT antisense primer

<400> SEQUENCE: 18
ccagcaagct tgcaacctta acca                                         24

<210> SEQ ID NO 19
```

```
<211> LENGTH: 9
<212> TYPE: PRT
<213> ORGANISM: Artificial Sequence
<220> FEATURE:
<223> OTHER INFORMATION: FLAG epitope tag sequence

<400> SEQUENCE: 19

Asp Tyr Lys Asp Asp Asp Asp Lys Leu
1               5

<210> SEQ ID NO 20
<211> LENGTH: 25
<212> TYPE: DNA
<213> ORGANISM: Artificial Sequence
<220> FEATURE:
<223> OTHER INFORMATION: TECK sense primer

<400> SEQUENCE: 20
ccttcaggta tctggagagg agatc                                          25

<210> SEQ ID NO 21
<211> LENGTH: 22
<212> TYPE: DNA
<213> ORGANISM: Artificial Sequence
<220> FEATURE:
<223> OTHER INFORMATION: TECK antisense primer

<400> SEQUENCE: 21
cacgcttgta ctgttggggt tc                                             22

<210> SEQ ID NO 22
<211> LENGTH: 27
<212> TYPE: DNA
<213> ORGANISM: Artificial Sequence
<220> FEATURE:
<223> OTHER INFORMATION: exon 1-specific CRAM primer

<400> SEQUENCE: 22
agacgcttca gagatcctct ggaggcc                                        27

<210> SEQ ID NO 23
<211> LENGTH: 26
<212> TYPE: DNA
<213> ORGANISM: Artificial Sequence
<220> FEATURE:
<223> OTHER INFORMATION: exon 2-specific CRAM primer

<400> SEQUENCE: 23
gaagctgctt cgggggtga gcaaac                                          26

<210> SEQ ID NO 24
<211> LENGTH: 29
<212> TYPE: DNA
<213> ORGANISM: Artificial Sequence
<220> FEATURE:
<223> OTHER INFORMATION: exon 3-specific CRAM primer

<400> SEQUENCE: 24
caaacacagc agagcagagt gatggcacc                                      29

<210> SEQ ID NO 25
<211> LENGTH: 23
<212> TYPE: DNA
<213> ORGANISM: Artificial Sequence
<220> FEATURE:
<223> OTHER INFORMATION: CRAM primer
```

-continued

```
<400> SEQUENCE: 25
gtgtcctggc atgggtaaca gcc                                              23

<210> SEQ ID NO 26
<211> LENGTH: 24
<212> TYPE: DNA
<213> ORGANISM: Artificial Sequence
<220> FEATURE:
<223> OTHER INFORMATION: CRAM primer

<400> SEQUENCE: 26
cggtggaatg gtcaggttct tccc                                             24
```

CHEMOKINE TECK POLYPEPTIDES

This application is a divisional application of U.S. Ser. No. 10/039,659, filed Jan. 3, 2002, now U.S. Pat. No. 6,723,520, which is a divisional application of U.S. Ser. No. 08/887,977 filed Jul. 3, 1997, now abandoned which claims the benefit of U.S. Ser. No. 60/021,664 filed Jul. 5, 1996; U.S. Ser. No. 60/028,329 filed Oct. 11, 1996; and U.S. Ser. No. 60/048,593 filed Jun. 4, 1997.

All references cited herein are incorporated in their entirety by reference.

FIELD OF THE INVENTION

The present invention relates to compositions related to proteins which function in controlling physiology, development, and/or differentiation of mammalian cells, e.g., cells of a mammalian immune system. In particular, it provides proteins and mimetics which regulate physiology, development, differentiation, and function of various cell types, including hematopoietic cells. It also provides receptor reagents for chemokine-like proteins.

BACKGROUND OF THE INVENTION

The circulating component of the mammalian circulatory system comprises various cell types, including red and white blood cells of the erythroid or the myeloid cell lineages. See, e.g., Rapaport (1987) *Introduction to Hematology* (2d ed.) Lippincott, Philadelphia, Pa.; Jandl (1987) *Blood: Textbook of Hematology*, Little, Brown and Co., Boston, Mass.; and Paul (ed.)(1993) *Fundamental Immunology* 3d ed, Raven Press, N.Y. Progression through various stages of differentiation are regulated by various signals provided to the cells, often mediated through a class of proteins known as the cytokines. Within this group of molecules as a further group known as the chemoattractant cytokines, or chemokines. See, e.g., Schall (1994) "The Chemokines" in Thomson (ed.) *The Cytokine Handbook* (2d ed.) Academic Press; and Schall and Bacon (1994) *Current Opinion in Immunology* 6:865-873.

Although the full spectrum of biological activities of the chemokines has not been extensively investigated, chemoattractant effects are recognized. The best known biological functions of these molecules relate to chemoattraction of leukocytes. However, new chemokines are being discovered, and their biological effects on the various cells responsible for immunological responses are topics of continued study.

Certain G-protein coupled receptors have also been characterized, presumably chemokine receptors. See, e.g., Samson, et al. (1996) *Biochemistry* 35:3362-3367; and Rapport, et al. (1996) *J. Leukocyte Biology* 59:18-23.

These observations indicate that other factors exist whose functions in hematopoiesis, immune development, and leukocyte trafficking were heretofore unrecognized. These factors provide for biological activities whose spectra of effects are distinct from known differentiation, activation, or other signaling factors. The absence of knowledge about the structural, biological, and physiological properties of the regulatory factors which regulate hematopoietic cell physiology in vivo prevents the modification of the effects of such factors. Thus, medical conditions where regulation of the development or physiology of relevant cells is required remains unmanageable.

SUMMARY OF THE INVENTION

The present invention is based, in part, upon the discovery of new genes encoding chemokines, and new genes encoding various receptors for chemokines. It embraces agonists and antagonists of the chemokines. In particular, sequences of various chemokines, e.g., designated Thymus Expressed ChemoKine (TECK); MIP-3α; MIP-3β; and 7 transmembrane receptors, designated "dendritic cell receptor for chemokine" (DC CR) and "monocyte/dendritic cell receptor for chemokine" (M/DC CR); and mutations (muteins) of the respective natural sequences, fusion proteins, chemical mimetics, antibodies, and other structural or functional analogs are provided. It is also directed to isolated genes encoding respective proteins of the invention. Various uses of these different protein or nucleic acid compositions are also provided.

The present invention provides a substantially pure or isolated polypeptide comprising a segment exhibiting sequence homology to a corresponding portion of a mature TECK, MIP-3α, MIP-3β, DC CR, or M/DC CR, wherein the homology is at least about 70% identity and the portion is at least about 25 amino acids. Preferably, the protein further comprises a second segment exhibiting at least about 90% identity over at least 9 amino acids; or at least about 80% identity over at least 17 amino acids. In other preferred embodiments, the polypeptide: is from a warm blooded animal selected from the group of birds and mammals, including a mouse or human; comprises a natural sequence from Tables 1 through 5; exhibits a post-translational modification pattern distinct from a natural form of the polypeptide; is made by expression of a recombinant nucleic acid; comprises synthetic sequence; is detectably labeled; is conjugated to a solid substrate; is conjugated to another chemical moiety; is a fusion protein; is in a denatured conformation, including detergent denaturation; further comprises an epitope tag; is an immunogenic polypeptide; has a defined homogeneous molecular weight; is useful as a carbon source; is an allelic variant of SEQ ID NO: 2, 4, 6, 8, 10, or 12; is a 3-fold or less substituted form of a natural sequence; is in a sterile composition; is in a buffered solution or suspension; is in a regulated release device; comprises a post-translational modification; is in a cell; or is in a kit which further comprises instructions for use or disposal of reagents therein.

In other aspects, the invention provides an isolated or recombinant nucleic acid encoding such protein, where the portion consists of sequence from the coding region of SEQ ID NO: 1, 3, 5, 7, 9, or 11. Other aspects include such nucleic acids which: exhibit at least about 80% identity to a natural cDNA encoding said segment; is in an expression vector; further comprises a promoter; further comprises an origin of replication; is from a natural source; is detectably labeled; comprises synthetic nucleotide sequence; is less than 6 kb; is from a mammal; comprises a natural full length mature coding sequence; is in a kit, which also comprises instructions for use or disposal of reagents therein; is a specific hybridization probe for a gene encoding the protein; is a PCR product; or is in a cell. The invention also provides a method of using a purified nucleic acid by expressing the nucleic acid to produce a protein.

Alternatively, the invention provides an isolated or recombinant nucleic acid which encodes at least eight consecutive residues of SEQ ID NO: 2, 4, 6, 8, 10, or 12. Preferably, that nucleic acid encodes at least: twelve consecutive residues from SEQ ID NO: 2, and further comprises a coding sequence of at least 17 nucleotides from SEQ ID NO: 1; twelve consecutive residues from SEQ ID NO: 4, and further comprises a coding sequence of at least 17 nucleotides from SEQ ID NO: 3; twelve consecutive residues from SEQ ID NO: 6, and further comprises a coding sequence of at least 17 nucleotides from SEQ ID NO: 5; twelve consecutive residues from SEQ ID NO: 8, and further comprises a coding sequence of at least 17 nucleotides from SEQ ID NO: 7; twelve consecutive residues from SEQ ID NO: 10, and further comprises a coding sequence of at least 17 nucleotides from SEQ ID NO: 9; or twelve consecutive residues from SEQ ID NO: 12, and further comprises a coding sequence of at least 17 nucleotides from SEQ ID NO: 11. In other preferred embodiments, the nucleic acid: exhibits at least about 80% identity to a natural cDNA encoding the segment; is in an expression vector; further comprises a promoter; further comprises an origin of replication; encodes a 3-fold or less substituted sequence from a natural sequence; is from a natural source; is detectably labeled; comprises synthetic nucleotide sequence; is less than 6 kb; is from a mammal; is attached to a solid substrate, including in a Southern or Northern blot; comprises a natural full length coding sequence; is in a cell; or is in a detection kit, which also comprises instructions for use or disposal of reagents therein. Further embodiments include a nucleic acid which hybridizes under stringent wash conditions of 55° C. and less than 150 mM salt to the nucleic acid; while preferred embodiments include those which exhibit at least about 85% identity over a stretch of at least about 30 nucleotides to a primate sequence of SEQ ID NO: 1, 3, 5, 7, 9, or 11; or where the identity is at least 90%; or the stretch is at least 75 nucleotides; or where the identity is at least 95%; or the stretch is at least 100 nucleotides.

In other embodiments, the invention provides a binding compound comprising an antigen binding fragment from an antibody which binds to a mature TECK, MIP-3α, MIP-3β, DC CR, or M/DC CR protein. In various embodiments, the binding compound is one wherein: the polypeptide is a mouse or human protein; the antibody is raised against a mature peptide sequence of Tables 1 through 5; the antibody is a monoclonal antibody; the binding compound is attached to a solid substrate; the binding compound is in a sterile composition; the binding compound binds to a denatured antigen, including a detergent denatured antigen; the binding compound is detectably labeled; the binding compound is an Fv, Fab, or Fab2 fragment; the binding compound is conjugated to a chemical moiety; the binding compound is in a detection kit which also comprises instructions for use or disposal of reagents therein.

The invention also provides a cell which makes the antibody.

The invention embraces methods of purifying a polypeptide using a binding compound to specifically separate said polypeptides from others; of generating an antigen-binding compound complex comprising the step of contacting a sample comprising the antigen to a sample comprising a binding compound; or of modulating physiology or development of a cell expressing a receptor for a chemokine selected from TECK, MIP-3α, or MIP-3β; the method comprising contacting the cell with a composition comprising an agonist or mutein of said chemokine or an antibody antagonist of the chemokine. In certain embodiments of the method, the cell is a macrophage, lymphocyte, or eosinophil; or the physiology is a cellular calcium flux, a chemoattractant response, cellular morphology modification responses, phosphoinositide lipid turnover, or an antiviral response. In other embodiments, the receptor is DC CR and the chemokine is MIP-3α, the physiology is pulmonary physiology, or the cell is an eosinophil.

DESCRIPTION OF THE DRAWINGS

FIG. 1A shows migration of mouse thymocytes to recombinant mTECK and effect of pertussis toxin. Chemotaxis assays were performed as described. Recombinant mouse lymphotactin was used as a positive control. Data are expressed as the mean of cell counts obtained from three separate experiments in duplicate ±SEM. In one experiment, cells were pre incubated 1 h with 10 ng/ml pertussis toxin (PTX) prior to the assay. FIG. 1B shows migration of other leukocyte subsets to recombinant mTECK. Mouse splenic dendritic cells and mouse activated macrophages were obtained. THP-1 human monocytic cells were used without or with a 16 h activation with IFN-γ. Results are obtained as the mean of the chemotactic index from three separate experiments per cell type in duplicate ±SD. The number of cells migrating to medium alone was greater than 40 cells per 5 high power fields in each experiment. Recombinant MIP-1α was used as a positive control.

DETAILED DESCRIPTION OF THE PREFERRED EMBODIMENTS

Figure 1A:
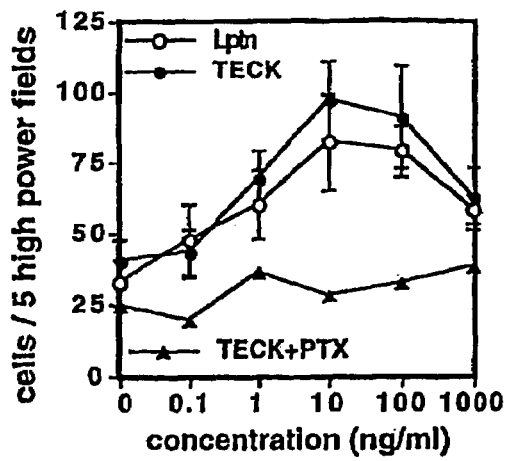
FIGS. 1A-1B show chemotactic properties of mTECK recombinant protein.

Outline
I. General
II. Purified Chemokines, Receptors
　A. physical properties
　B. biological properties
III. Physical Variants
　A. sequence variants, fragments
　B. post-translational variants
　　1. glycosylation
　　2. others
IV. Functional Variants
　A. analogs; fragments
　　1. agonists
　　2. antagonists
　B. mimetics
　　1. protein
　　2. chemicals
　C. species variants
V. Antibodies
　A. polyclonal
　B. monoclonal
　C. fragments, binding compositions
VI. Nucleic Acids
　A. natural isolates; methods
　B. synthetic genes
　C. methods to isolate
VII. Making Chemokines, Receptors; Mimetics
　A. recombinant methods
　B. synthetic methods
　C. natural purification
VIII. Uses
　A. diagnostic
　B. therapeutic
IX. Kits
　A. nucleic acid reagents
　B. protein reagents
　C. antibody reagents
X. Receptors
　I. General The present invention provides DNA sequences encoding various mammalian proteins which exhibit structural properties characteristic of a chemotactic cytokine, or chemokine. Other embodiments are directed to chemokine receptors. See, e.g., Lodi, et al. (1994) *Science* 263:1762-1767; Gronenborn and Clore (1991) *Protein Engineering* 4:263-269; Miller and Kranger (1992) *Proc. Nat'l Acad. Sci. USA* 89:2950-2954; Matsushima and Oppenheim (1989) *Cytokine* 1:2-13; Stoeckle and Baker (1990) *New Biol.* 2:313-323; Oppenheim, et al. (1991) *Ann. Rev. Immunol.* 9:617-648; Schall (1991) *Cytokine* 3:165-183; and The *Cytokine Handbook* Academic Press, NY. Mouse and human embodiments are described herein.

Chemokines play an important role in immune and inflammatory responses by inducing migration and adhesion of leukocytes. These small secreted molecules are a growing superfamily of 8-14 kDa proteins characterized by a conserved four cysteine motif. See, e.g., Schall (1991) *Cytokine* 3:165-183; and Thomson (ed.) *The Cytokine Handbook* Academic Press, NY. Chemokines are secreted by activated leukocytes and act as a chemoattractant for a variety of cells which are involved in inflammation. Besides chemoattractant properties, chemokines have been shown to induce other biological responses, e.g., modulation of second messenger levels such as $Ca^{++}$; inositol phosphate pool changes (see, e.g., Berridge (1993) *Nature* 361:315-325 or Billah and Anthes (1990) *Biochem. J.* 269:281-291); cellular morphology modification responses; phosphoinositide lipid turnover; possible antiviral responses; and others. Thus, the chemokines provided herein may, alone or in combination with other therapeutic reagents, have advantageous combination effects.

Moreover, there are reasons to suggest that chemokines may have effects on other cell types, e.g., attraction or activation of monocytes, dendritic cells, T cells, eosinophils, and/or perhaps on basophils and/or neutrophils. They may also have chemoattractive effects on various neural cells including, e.g., dorsal root ganglia neurons in the peripheral nervous system and/or central nervous system neurons.

Membrane proteins which contain seven transmembrane segments have been characterized as G-protein coupled receptors. Many of these receptors have been characterized as receptors for chemokines, based in part on structural features. Chemokine receptors are important in the signal transduction mechanisms mediated by the chemokines. They are useful markers for distinguishing cell populations, and have been implicated as specific receptors for retroviral infections.

The chemokine superfamily was classically divided into two groups exhibiting characteristic structural motifs, the Cys-X-Cys (C-X-C) and Cys-Cys (C-C) families. These were distinguished on the basis of a single amino acid insertion between the NH-proximal pair of cysteine residues and sequence similarity. Typically, the C-X-C chemokines, i.e., IL-8 and MGSA/Gro-α act on neutrophils but not on monocytes, whereas the C-C chemokines, i.e., MIP-1α and RANTES, are potent chemoattractants for monocytes and lymphocytes but not neutrophils. See, e.g., Miller, et al. (1992) *Crit. Rev. Immunol.* 12:17-46. A recently isolated chemokine, lymphotactin, does not belong to either group and may constitute a first member of a third chemokine family, the C family. Lymphotactin does not have a characteristic CC or CXC motif, and acts on lymphocytes but not neutrophils and monocytes. See, e.g., Kelner et al. (1994) *Science* 266:1395-1399. This chemokine defines a new C-C chemokine family. Even more recently, another chemokine exhibiting a CX3C motif has been identified, which establishes a fourth structural class.

The present invention provides additional chemokine reagents, e.g., nucleic acids, proteins and peptides, antibodies, etc., related to the newly discovered respective chemokines designated TECK; MIP-3α, and MIP3β.

In other embodiments, the invention provides two genes encoding novel 7-transmembrane (7-TM) receptors, presumably G-protein coupled receptors and likely chemokine receptors. These 7-TM receptors are hypothesized to be chemokine receptors and have been designated DC CR and M/DC CR. Their ligands have not yet specifically been completely identified. However, the receptors exhibit structural features typical of known chemokine receptors, e.g., 7 transmembrane spanning structures. They may exhibit properties of binding many different cytokines at varying specificities (shared or promiscuous binding specificity) or may exhibit high affinity for one (specific) or a subset (shared) of chemokines.

The described chemokines and receptors should be important for mediating various aspects of cellular, organ, tissue, or organismal physiology or development.

II. Purified Chemokines, Receptors

Mouse and human Thymus Expressed ChemoKine (TECK) nucleotide and amino acid sequences are shown in Table 1. Nucleotide and amino acid sequences of another novel chemokine, from human, designated MIP-3α are provided in Table 2. Nucleotide and derived amino acid sequences of a third novel chemokine, from human, designated MIP-3β are shown in Table 3. Generic descriptions of physical properties of polypeptides, nucleic acids, and antibodies where directed to one embodiment clearly are generally applicable to other chemokines or receptors described herein.

The nucleotide and amino acid sequences of a novel chemokine receptor found on dendritic cells (DC), from human, and designated DC CR, are provided in Table 4. The nucleotide and amino acid sequences of another novel chemokine receptor found on macrophages and dendritic cells, from human, and designated M/DC CR, are provided in Table 5.

These amino acid sequences, provided amino to carboxy, are important in providing sequence information on the chemokine ligand or receptor, allowing for distinguishing the protein from other proteins. Moreover, the sequences allow preparation of peptides to generate antibodies to recognize and distinguish such segments, and allow preparation of oligonucleotide probes, both of which are strategies for isolation, e.g., cloning, of genes encoding such sequences, or related sequences, e.g., natural polymorphic or other variants. Similarities of the chemokines have been observed with other cytokines. See, e.g., Bosenberg, et al. (1992) *Cell* 71:1157-1165; Huang, et. al. (1992) *Molecular Biology of the Cell* 3:349-362; and Pandiella, et al. (1992) *J. Biol. Chem.* 267:24028-24033. Likewise for the receptors.

TABLE 1

Nucleotide sequence (5' to 3') of TECK from mouse and the corresponding amino acid sequence (amino to carboxy). Signal sequence probably runs as shown between Ala and Gln, see SEQ ID NO: 1 and 2. Human sequences are SEQ ID NO: 3 and 4.

```
  1   AGGCTACAAGCAGGCACCAGCTCTCAGGACCAGAAAGGCATTGTGGCCCCCTTAAACCT      60

61   TCAGGTATCTGGAGAGGAGATCTAACCTTCACTATGAAACTGTGGCTTTTTGCCTGCCTG    120
  1                                       MetLysLeuTrpLeuPheAlaCysLeu    9

121   GTTGCCTGTTTTGTTGGGGCCTGGATGCCGGTTGTCCATGCCCAAGGTGCCTTTGAAGAC    180
 10   ValAlaCysPheValGlyAlaTrpMetProValValHisAlaGlnGlyAlaPheGluAsp    29

181   TGCTGCCTGGGTTACCAGCACAGGATCAAATGGAATGTTCTCCGGCATGCTAGGAATTAT    240
 30   CysCysLeuGlyTyrGlnHisArgIleLysTrpAsnValLeuArgHisAlaArgAsnTyr    49

241   CACCAGCAGGAAGTGAGTGGAAGCTGCAACCTACGTGCTGTGAGATTCTACTTCCGCCAG    300
 50   HisGlnGlnGluValSerGlySerCysAsnLeuArgAlaValArgPheTyrPheArgGln    69

301   AAAGTAGTGTGTGGGAATCCAGAGGACATGAATGTGAAGAGGGCGATAAGAATCTTGACA    360
 70   LysValValCysGlyAsnProGluAspMetAsnValLysArgAlaIleArgIleLeuThr    89

361   GCTAGGAAAAGGCTAGTCCACTGGAAGAGCGCCTCAGACTCTCAGACTGAAAGGAAGAAG    420
 90   AlaArgLysArgLeuValHisTrpLysSerAlaSerAspSerGlnThrGluArgLysLys   109

421   TCAAACCATATGAAGTCCAAGGTGGAGAACCCCAACAGTACAAGCGTGAGGAGTGCCACC    480
110   SerAsnHisMetLysSerLysValGluAsnProAsnSerThrSerValArgSerAlaThr   129

481   CTAGGTCATCCCAGGATGGTGATGATGCCCAGAAAGACCAACAATTAAGTTAATTACTCA    540
130   LeuGlyHisProArgMetValMetMetProArgLysThrAsnAsnEnd                144

541   GAGTAAGCACCAGCTGGAGGATGGGCGGAGTCTGCTGAAGTGCTGTCTTCTAGGCATGCC    600

601   AGTGCCAATGAACTCACTGAAGCTACAGTTTCCTGTACAAGACCAGACCCACCAACGTCT    660

661   CAGCATGTACGAGGAAGGAACTACTGCGCTAAAGGCCCTCCCACTCACCAAGGAGCTATT    720

721   GGCTATTGATGATTGCTGAGGGAAGGGAGTAATTTTTTTTCTCTTTCTGAAGTGTGACTT    780

781   GAGTAAATTGCCCATAGTTCAGTATATAATCCCCAACCTGTGCTCAGGCAAGCAACCCTA    840

841   ATTAAATGCAATAGCCACATACAAAAGAAGAGGATATGAATAGTTTGGTAGGAGGGCTT    900

901   GTTAGGAAGAAGACATTAACAGGAGAGAGAGGAGCGAGAGGATAGTGAGTGTGTGAGAGT    960

961   GCCTGCACGTGTGAAATGGTCAAAGAATTAAAAAATAAAAACTTAAAAAGCTATTAAAAA   1020

1021  GTAAAAAAAATAAA    1034
``` human Teck cDNA (see SEQ ID NO: 3); signal sequence cleavage is probably between about Thr and Gln. Hu TECK protein sequence (see SEQ ID NO: 4).

```
TCGACCCACG CGTCCGCTTG GCCTACAGCC CGGCGGGCAT CAGCTCCCTT GACCCAGTGG       60

ATATCGGTGG CCCCGTTATT CGTCCAGGTG CCCAGGGAGG AGGACCCGCC TGCAGC          116

ATG AAC CTG TGG CTC CTG GCC TGC CTG GTG GCC GGC TTC CTG GGA GCC         164
Met Asn Leu Trp Leu Leu Ala Cys Leu Val Ala Gly Phe Leu Gly Ala
-23         -20                 -15                 -10

TGG GCC CCC GCT GTC CAC ACC CAA GGT GTC TTT GAG GAC TGC TGC CTG         212
Trp Ala Pro Ala Val His Thr Gln Gly Val Phe Glu Asp Cys Cys Leu
        -5                   1                   5

GCC TAC CAC TAC CCC ATT GGG TGG GCT GTG CTC CGG CGC GCC TGG ACT         260
Ala Tyr His Tyr Pro Ile Gly Trp Ala Val Leu Arg Arg Ala Trp Thr
10              15                  20                  25

TAC CGG ATC CAG GAG GTG AGC GGG AGC TGC AAT CTG CCT GCT GCG ATA         308
Tyr Arg Ile Gln Glu Val Ser Gly Ser Cys Asn Leu Pro Ala Ala Ile
                30                  35                  40

TTC TAC CTC CCC AAG AGA CAC AGG AAG GTG TGT GGG AAC CCC AAA AGC         356
Phe Tyr Leu Pro Lys Arg His Arg Lys Val Cys Gly Asn Pro Lys Ser
        45                  50                  55
```

TABLE 1-continued

Nucleotide sequence (5' to 3') of TECK from mouse and the corresponding amino acid sequence (amino to carboxy). Signal sequence probably runs as shown between Ala and Gln, see SEQ ID NO: 1 and 2. Human sequences are SEQ ID NO: 3 and 4.

```
AGG GAG GTG CAG AGA GCC ATG AAG CTC CTG GAT GCT CGA AAT AAG GTT    404
Arg Glu Val Gln Arg Ala Met Lys Leu Leu Asp Ala Arg Asn Lys Val
        60                  65                  70

TTT GCA AAG CTC CAC CAC AAC ATG CAG ACC TTC CAA GCA GGC CCT CAT    452
Phe Ala Lys Leu His His Asn Met Gln Thr Phe Gln Ala Gly Pro His
    75                  80                  85

GCT GTA AAG AAG TTG AGT TCT GGA AAC TCC AAG TTA TCA TCA TCC AAG    500
Ala Val Lys Lys Leu Ser Ser Gly Asn Ser Lys Leu Ser Ser Ser Lys
90                  95                 100                 105

TTT AGC AAT CCC ATC AGC AGC AGC AAG AGG AAT GTC TCC CTC CTG ATA    548
Phe Ser Asn Pro Ile Ser Ser Ser Lys Arg Asn Val Ser Leu Leu Ile
                110                 115                 120

TCA GCT AAT TCA GGA CTG TGAGCCGGCT CATTTCTGGG CTCCATCGGC           596
Ser Ala Asn Ser Gly Leu
                125

ACAGGAGGGG CCGGATCTTT CTCCGATAAA ACCGTCGCCC TACAGACCCA GCTGTCCCCA  656

CGCCTCTGTC TTTTGGGTCA AGTCTTAATC CCTGCACCTG AGTTGGTCCT CCCTCTGCAC  716

CCCCACCACC TCCTGCCCGT CTGGCAACTG GAAAGAAGGA GTTGGCCTGA TTTTAACCTT  776

TTGCCGCTCC GGGGAACAGC ACAATCCTGG GCAGCCAGTG GCTCTTGTAG AGAAAACTTA  836

GGATACCTCT CTCACTTTCT GTTTCTTGCC GTCCACCCCG GGCCATGCCA GTGTGTCCTC  896

TGGGTCCCCT CCAAAAATCT GGTCATTCAA GGATCCCCTC CCAAGGCTAT GCTTTTCTAT  956

AACTTTTAAA TAAACCTTGG GGGGTGAATG GAATAAAAAA AAAAAAAAAA AAAAAA      1012
```

TABLE 2

Nucleotide sequence (5' to 3') of MIP-3α from human and the corresponding amino acid sequence (amino to carboxy), see SEQ ID NO: 5 and 6 and GenBank Accession U77035.

```
ATG TGC TGT ACC AAG AGT TTG CTC CTG GCT GCT TTG ATG TCA GTG CTG    48
Met Cys Cys Thr Lys Ser Leu Leu Leu Ala Ala Leu Met Ser Val Leu
-26 -25                 -20                 -15

CTA CTC CAC CTC TGC GGC GAA TCA GAA GCA GCA AGC AAC TTT GAC TGC    96
Leu Leu His Leu Cys Gly Glu Ser Glu Ala Ala Ser Asn Phe Asp Cys
-10                 -5                   1                   5

TGT CTT GGA TAC ACA GAC CGT ATT CTT CAT CCT AAA TTT ATT GTG GGC    144
Cys Leu Gly Tyr Thr Asp Arg Ile Leu His Pro Lys Phe Ile Val Gly
                10                  15                  20

TTC ACA CGG CAG CTG GCC AAT GAA GGC TGT GAC ATC AAT GCT ATC ATC    192
Phe Thr Arg Gln Leu Ala Asn Glu Gly Cys Asp Ile Asn Ala Ile Ile
    25                  30                  35

TTT CAC ACA AAG AAA AAG TTG TCT GTG TGC GCA AAT CCA AAA CAG ACT    240
Phe His Thr Lys Lys Lys Leu Ser Val Cys Ala Asn Pro Lys Gln Thr
        40                  45                  50

TGG GTG AAA TAT ATT GTG CGT CTC CTC AGT AAA AAA GTC AAG AAC ATG    288
Trp Val Lys Tyr Ile Val Arg Leu Leu Ser Lys Lys Val Lys Asn Met
55                  60                  65                  70

TAAAAACTGT GGCTTTTCTG GAATGGAATT GGACATAGCC CAAGAACAGA AGAACCTTG   348

CTGGGGTTGG AGGTTTCACT TGCACATCAT GGAGGGTTTA GTGCTTATCT AATTTGTGCC  408

TCACTGGACT TGTCCAATTA ATGAAGTTGA TTCATATTGC ATCATAGTTT GCTTTGTTTA  468
```

TABLE 2-continued

Nucleotide sequence (5' to 3') of MIP-3α from human and the corresponding amino acid sequence (amino to carboxy), see SEQ ID NO: 5 and 6 and GenBank Accession U77035.

```
AGCATCACAT TAAAGTTAAA CTGTATTTTA TGTTATTTAT AGCTGTAGGT TTTCTGTGTT   528

TAGCTATTTA ATACTAATTT TCCATAAGCT ATTTTGGTTT AGTGCAAAGT ATAAAATTAT   588

ATTTGGGGGG GAATAAGATT ATATGGACTT TTTTGCAAGC AACAAGCTAT TTTTTAAAAA   648

AAACTATTTA ACATTCTTTT GTTTATATTG TTTTGTCTCC TAAATTGTTG TAATTGCATT   708

ATAAAATAAG AAAAATATTA ATAAGACAAA TATTGAAAAT AAAGAAACAA AAAGTTAAAA   768

AAAAAAAAAA AAAAAAAAAA AAAAAAAAAA AAA                                801
```

TABLE 3

Nucleotide sequence (5' to 3') of MIP-3β from human and the corresponding amino acid sequence (amino to carboxy), see SEQ ID NO: 7 and 8, and GenBank Accession U77180. Signal sequence cleavage is about between Ser and Gly.

```
  1 GGCACGAGCGGCACGAGCATCACTCACACCTTGCATTTCACCCCTGCATCCCAGTCGCCC   60

61 TGCAGCCTCACACAGATCCTGCACACACCCAGACAGCTGGCGCTCACACATTCACCGTTG  120

121 GCCTGCCTCTGTTCACCCTCCATGGCCCTGCTACTGGCCCTCAGCCTGCTGGTTCTCTGG  180
  1                     MetAlaLeuLeuLeuAlaLeuSerLeuLeuValLeuTrp   13

181 ACTTCCCCAGCCCCAACTCTGAGTGGCACCAATGATGCTGAAGACTGCTGCCTGTCTGTG  240
 14 ThrSerProAlaProThrLeuSerGlyThrAsnAspAlaGluAspCysCysLeuSerVal   33

241 ACCCAGAAACCCATCCCTGGGTACATCGTGAGGAACTTCCACTACCTTCTCATCAAGGAT  300
 34 ThrGlnLysProIleProGlyTyrIleValArgAsnPheHisTyrLeuLeuIleLysAsp   53

301 GGCTGCAGGGTGCCTGCTGTAGTGTTCACCACACTGAGGGGCCGCCAGCTCTGTGCACCC  360
 54 GlyCysArgValProAlaValValPheThrThrLeuArgGlyArgGlnLeuCysAlaPro   73

361 CCAGACCAGCCCTGGGTAGAACGCATCATCCAGAGACTGCAGAGGACCTCAGCCAAGATG  420
 74 ProAspGlnProTrpValGluArgIleIleGlnArgLeuGlnArgThrSerAlaLysMet   93

421 AAGCGCCGCAGCAGTTAACCTATGACCGTGCAGAGGGAGCCCGGAGTCCGAGTCAAGCAT  480
 94 LysArgArgSerSerEnd                                              98

481 TGTGAATTATTACCTAACCTGGGGAACCGAGGACCAGAAGGAAGGACCAGGCTTCCAGCT  540

541 CCTCTGCACCAGACCTGACCAGCCAGGACAGGGCCTGGGGTGTGTGTGAGTGTGAGTGTG  600

601 AGCGAGAGGGTGAGTGTGGTCTAGAGTAAAGCTGCTCCACCCCCAGATTGCAATGCTACC  660

661 AATAAAGCCGCCTGGTGTTTACAACTAAAAAAAAAAAAA                        699
```

TABLE 4

Nucleotide sequence (5' to 3') of chemokine receptor, DC CR, from human and the corresponding amino acid sequence (amino to carboxy), see SEQ ID NO: 9 and 10. Nucleotide 579 may be A, C, G, or T, and the codon may code for His or Gln.

```
  1 ATGTTTTCGACTCCAGTGAAGATTATTTTGTGTCAGTCAATACTTCATATTACTCAGTTG   60
  1 MetPheSerThrProValLysIleIleLeuCysGlnSerIleLeuHisIleThrGlnLeu   20

61 ATTCTGAGATGTTACTGTGCTCCTTGCAGGAGGTCAGGCAGTTCTCCAGGCTATTTGTAC  120
 21 IleLeuArgCysTyrCysAlaProCysArgArgSerGlySerSerProGlyTyrLeuTyr   40

121 CGAATTGCCTACTCCTTGATCTGTGTTCTTGGCCTCCTGGGGAATATTCTGGTGGTGATC  180
 41 ArgIleAlaTyrSerLeuIleCysValLeuGlyLeuLeuGlyAsnIleLeuValValIle   60

181 ACCTTTGCTTTTTATAAGAAGGCCAGGTCTATGACAGACGTCTATCTCTTGAACATGGCC  240
 61 ThrPheAlaPheTyrLysLysAlaArgSerMetThrAspValTyrLeuLeuAsnMetAla   80
```

TABLE 4-continued

Nucleotide sequence (5' to 3') of chemokine receptor, DC CR, from human and the corresponding amino acid sequence (amino to carboxy), see SEQ ID NO: 9 and 10. Nucleotide 579 may be A, C, G, or T, and the codon may code for His or Gln.

```
241 ATTGCAGACATCCTCTTTGTTCTTACTCTCCCATTCTGGGCAGTGAGTCATGCCACTGGT  300
 81 IleAlaAspIleLeuPheValLeuThrLeuProPheTrpAlaValSerHisAlaThrGly  100

301 GCGTGGGTTTTCAGCAATGCCACGTGCAAGTTGCTAAAAGGCATCTATGCCATCAACTTT  360
101 AlaTrpValPheSerAsnAlaThrCysLysLeuLeuLysGlyIleTyrAlaIleAsnPhe  120

361 AACTGCGGGATGCTGCTCCTGACTTGCATTAGCATGGACCGGTACATCGCCATTGTACAG  420
121 AsnCysGlyMetLeuLeuLeuThrCysIleSerMetAspArgTyrIleAlaIleValGln  140

421 GCGACTAAGTCATTCCGGCTCCGATCCAGAACACTACCGCGCAGCAAAATCATCTGCCTT  480
141 AlaThrLysSerPheArgLeuArgSerArgThrLeuProArgSerLysIleIleCysLeu  160

481 GTTGTGTGGGGCTGTCAGTCATCATCTCCAGCTCAACTTTTGTCTTCAACCAAAAATAC   540
161 ValValTrpGlyLeuSerValIleIleSerSerThrPheValPheAsnGlnLysTyr     180

541 AACACCCAAGGCAGCGATGTCTGTGAACCCAAGTACCAAACTGTCTCGGAGCCCATCAGG  600
181 AsnThrGlnGlySerAspValCysGluProLysTyrGlnThrValSerGluProIleArg  200

601 TGGAAGCTGCTGATGTTGGGGCTTGAGCTACTCTTTGGTTTCTTTATCCCTTTGATGTTC  660
201 TrpLysLeuLeuMetLeuGlyLeuGluLeuLeuPheGlyPhePheIleProLeuMetPhe  220

661 ATGATATTTTGTTACACGTTCATTGTCAAAACCTTGGTGCAAGCTCAGAATTCTAAAAGG  720
221 MetIlePheCysTyrThrPheIleValLysThrLeuValGlnAlaGlnAsnSerLysArg  240

721 CACAAAGCCATCCGTGTAATCATAGCTGTGGTGCTTGTGTTTCTGGCTTGTCAGATTCCT  780
241 HisLysAlaIleArgValIleIleAlaValValLeuValPheLeuAlaCysGlnIlePro  260

781 CATAACATGGTCCTGCTTGTGACGGCTGCTAATTTGGGTAAAATGAACCGATCCTGCCAG  840
261 HisAsnMetValLeuLeuValThrAlaAlaAsnLeuGlyLysMetAsnArgSerCysGln  280

841 AGCGAAAAGCTAATTGGCTATACGAAAACTGTCACAGAAGTCCTGGCTTTCCTGCACTGC  900
281 SerGluLysLeuIleGlyTyrThrLysThrValThrGluValLeuAlaPheLeuHisCys  300

901 TGCCTGAACCCTGTGCTCTACGCTTTTATTGGGCAGAAGTTCAGAAACTACTTTCTGAAG  960
301 CysLeuAsnProValLeuTyrAlaPheIleGlyGlnLysPheArgAsnTyrPheLeuLys  320

961 ATCTTGAAGGACCTGTGGTGTGTGAGAAGGAAGTACAAGTCCTCAGGCTTCTCCTGTGCC  1020
321 IleLeuLysAspLeuTrpCysValArgArgLysTyrLysSerSerGlyPheSerCysAla  340

1021 GGGAGGTACTCAGAAAACATTTCTCGGCAGACCAGTGAGACCGCAGATAACGACAATGCG  1080
341 GlyArgTyrSerGluAsnIleSerArgGlnThrSerGluThrAlaAspAsnAspAsnAla  360

1081 TCGTCCTTCACTATGTGATAGAAAGCTGAGTCTCCCTAA                       1119
361 SerSerPheThrMetEnd                                            365
```

TABLE 5

Nucleotide sequence (5' to 3') of chemokine receptor, M/DC CR, from human and the corresponding amino acid sequence (amino to carboxy), see SEQ ID NO: 11 and 12.

```
  1 GAGGAAGCTGCTTCGGGGGGTGAGCAAACTTTTTAAAATGCAGAAATTATGATCTACACC   60
  4                                                 MetIleTyrThr

61 CGTTTCTTAAAAGGCAGTCTGAAGATGGCCAATTACACGCTGGCACCAGAGGATGAATAT  120
  5 ArgPheLeuLysGlySerLeuLysMetAlaAsnTyrThrLeuAlaProGluAspGluTyr   24

121 GATGTCCTCATAGAAGGTGAACTGGAGAGCGATGAGGCAGAGCAATGTGACAAGTATGAC  180
 25 AspValLeuIleGluGlyGluLeuGluSerAspGluAlaGluGlnCysAspLysTyrAsp   44

181 GCCCAGGCACTCTCAGCCCAGCTGGTGCCATCACTCTGCTCTGCTGTGTTTGTGATCGGT  240
 45 AlaGlnAlaLeuSerAlaGlnLeuValProSerLeuCysSerAlaValPheValIleGly   64

241 GTCCTGGACAATCTCCTGGTTGTGCTTATCCTGGTAAAATATAAAGGACTCAAACGCGTG  300
 65 ValLeuAspAsnLeuLeuValValLeuIleLeuValLysTyrLysGlyLeuLysArgVal   84

301 GAAAATATCTATCTTCTAAACTTGGCAGTTTCTAACTTGTGTTTCTTGCTTACCCTGCCC  360
 85 GluAsnIleTyrLeuLeuAsnLeuAlaValSerAsnLeuCysPheLeuLeuThrLeuPro  104
```

TABLE 5-continued

Nucleotide sequence (5' to 3') of chemokine receptor, M/DC CR, from human and the corresponding amino acid sequence (amino to carboxy), see SEQ ID NO: 11 and 12.

```
 361 TTCTGGGCTCATGCTGGGGGCGATCCCATGTGTAAAATTCTCATTGGACTGTACTTCGTG  420
 105 PheTrpAlaHisAlaGlyGlyAspProMetCysLysIleLeuIleGlyLeuTyrPheVal  124

421 GGCCTGTACAGTGAGACATTTTTCAATTGCCTTCTGACTGTGCAAAGGTACCTAGTGTTT  480
 125 GlyLeuTyrSerGluThrPhePheAsnCysLeuLeuThrValGlnArgTyrLeuValPhe  144

481 TTGCACAAGGGCAACTTTTTCTCAGCCAGGAGGAGGGTGCCCTGTGGCATCATTACAAGT  540
 145 LeuHisLysGlyAsnPhePheSerAlaArgArgArgValProCysGlyIleIleThrSer  164

541 GTCCTGGCATGGGTAACAGCCATTCTGGCCACTTTGCCTGAATTCGTGGTTTATAAACCT  600
 165 ValLeuAlaTrpValThrAlaIleLeuAlaThrLeuProGluPheValValTyrLysPro  184

601 CAGATGGAAGACCAGAAATACAAGTGTGCATTTAGCAGAACTCCCTTCCTGCCAGCTGAT  660
 185 GlnMetGluAspGlnLysTyrLysCysAlaPheSerArgThrProPheLeuProAlaAsp  204

661 GAGACATTCTGGAAGCATTTTCTGACTTTAAAAATGAACATTTCGGTTCTTGTCCTCCCC  720
 205 GluThrPheTrpLysHisPheLeuThrLeuLysMetAsnIleSerValLeuValLeuPro  224

721 CTATTTATTTTTACATTTCTCTATGTGCAAATGAGAAAAACACTAAGGTTCAGGGAGCAG  780
 225 LeuPheIlePheThrPheLeuTyrValGlnMetArgLysThrLeuArgPheArgGluGln  244

781 AGGTATAGCCTTTTCAAGCTTGTTTTTGCCGTAATGGTAGTCTTCCTTCTGATGTGGGCG  840
 245 ArgTyrSerLeuPheLysLeuValPheAlaValMetValValPheLeuLeuMetTrpAla  264

841 CCCTACAATATTGCATTTTTCCTGTCCACTTTCAAAGAACACTTCTCCCTGAGTGACTGC  900
 265 ProTyrAsnIleAlaPhePheLeuSerThrPheLysGluHisPheSerLeuSerAspCys  284

901 AAGAGCAGCTACAATCTGGACAAAAGTGTTCACATCACTAAACTCATCGCCACCACCCAC  960
 285 LysSerSerTyrAsnLeuAspLysSerValHisIleThrLysLeuIleAlaThrThrHis  304

961 TGCTGCATCAACCCTCTCCTGTATGCGTTTCTTGATGGGACATTTAGCAAATACCTCTGC
1020
 305 CysCysIleAsnProLeuLeuTyrAlaPheLeuAspGlyThrPheSerLysTyrLeuCys  324

1021 CGCTGTTTCCATCTGCGTAGTAACACCCCACTTCAACCCAGGGGGCAGTCTGCACAAGGC
1080
 325 ArgCysPheHisLeuArgSerAsnThrProLeuGlnProArgGlyGlnSerAlaGlnGly  344

1081 ACATCGAGGGAAGAACCTGACCATTCCACCGAAGTGTAAACTAGCATCCACCAAATGCAA
1140
 345 ThrSerArgGluGluProAspHisSerThrGluValEnd                       356

1141 GAAGAATAAACATGGATTTTCATCTTTCTGCATTATTTCATGTAAATTTTCTACACATTT
1200

1201 GTATACAAAATCGGATACAGGAAGAAAAGGGAGAGGTGAGCTAACATTTGCTAAGCACTG
1260

1261 AATTTGTCTCAGGCACCGTGCAAGGCTCTTTACAAACGTGAGCTCCTTCGCCTCCTACCA
1320

1321 CTTGTCCATAGTGTGGATAGGACTAGTCTCATTTCTCTGAGAAGAAAACTAAGGCGCGGA
1380

1381 AATTTGTCTAAGATCACATAACTAGGAAGTGGCAGAACTGATTCTCCAGCCCTGGTAGCA
1440

1441 TTTGCTCAGAGCCTACGCTTGGTCCAGAACATCAAACTCCAAACCCTGGGGACAAACGAC
1500

1501 ATGAAATAAATGTATTTTAAACATATAAAAAAAAAAAAAAAAAAA
1547
```

TABLE 6

Alignment of M/DC CR with CKR-1 through CKR-4. The other chemokine receptors are SEQ ID NO: 13-17. An asterisk indicates fully conserved residue among all five receptors; a period represents conservative substitutions among all five receptors.

```
M/DC CR    MIYTRFLKGSLKMANYTLAPEDEYDVLIEGELESDEAEQCDKYDAQALS
C-C CKR-1              METPNTTEDYDTTTEFDYGDATPCQKVNERAFG
C-C CKR-2        MLSTSRSRFIRNTNESGEEVTTFFDYDYGAPCHKFDVKQIG
C-C CKR-3             MTTSLDTVETFGTTSYYDDVGLLCEKADTRALM
C-C CKR-4           MNPTDIADTTLDESIYSNYYLYESIPKPCTKEGIKAFG
                                                 *  *    . .

M/DC CR    AQLVPSLCSAVFVIGVLDNLLVVLILVKYKGLKRVENIYLLNLAVSNLCF
C-C CKR-1  AQLLPPLYSLVFVIGLVGNILVVLVLVQYKRLKNMTSIYLLNLAISDLLF
C-C CKR-2  AQLLPPLYSLVFIFGFVGNMLVVLILINCKKLKCLTDIYLLNLAISDLLF
C-C CKR-3  AQFVPPLYSLVFTVGLLGNVVVVMILIKYRRLRIMTNIYLLNLAISDLLF
C-C CKR-4  ELFLPPLYSLVFVFGLLGNSVVVLVLFKYKRLRSMTDVYLLNLAISDLLF
            ..*.* * **  * ...* .**..*  . . *. .  .******.*.* *

M/DC CR    LLTLPFWAHAG-------GDPMCKILIGLYFVGLYSETFFNCLLTVQRYL
C-C CKR-1  LFTLPFWIDYKLKDDWVFGDAMCKILSGFYYTGLYSEIFFIILLTIDRYL
C-C CKR-2  LITLPLWAH-SAANEWVFGNAMCKLFTGLYHIGYFGGIFFIILLTIDRYL
C-C CKR-3  LVTLPFWIHYVRGHNWVFGHGMCKLLSGFYHTGLYSEIFFIILLTIDRYL
C-C CKR-4  VFSLPFWGYYA-ADQWVFGLGLCKMISWMYLVGFYSGIFFVMLMSIDRYL
           . .**.*              * .**..  *   * ..  ** *....***

M/DC CR    VFLHKGNFFSAR-RRVPCGIITSVLAWVTAILATLPEFVVYKPQMEDQKY
C-C CKR-1  AIVH--AVFALRARTVTFGVITSIIIWALAILASMPGLYFSKTQWEFTHH
C-C CKR-2  AIVH--AVFALKARTVTFGVVTSVITWLVAVFASVPGIIFTKCQKEDSVY
C-C CKR-3  AIVH--AVFALRARTVTFGVITSIVTWGLAVLAALPEFIFYETEELFEET
C-C CKR-4  AIVH--AVFSLRARTLTYGVITSLATWSVAVFASLPGFLFSTCYTERNHT
            ..*    *. . * .  *...**.   *  *...*..* .

M/DC CR    KCAFSRTPFLPADETF-WKHFLTLKMNISVLVLPLFIFTFLYVQMRKTL-
C-C CKR-1  TCS----LHFPHESLREWKLFQALKLNLFGLVLPLLVMIICYTGIIKILL
C-C CKR-2  VCG----PYFPR----GWNNFHTIMRNILGLVLPLLIMVICYSGILKTLL
C-C CKR-3  LCS----ALYPEDTVYSWRHFHTLRMTIFCLVLPLLVMAICYTGIIKTLL
C-C CKR-4  YCK----TKYSLNST-TWKVLSSLEINILGLVIPLGIMLFCYSMIIRTLQ
            *       .      *  . ...  .  **.**  . *  . . *

M/DC CR    --RFREQRYSLFKLVFAVMVVFLLMWAPYNIAFFLSTFKEHFSLSDCKSS
C-C CKR-1  RRPNEKK-SKAVRLIFVIMIIFFLFWTPYNLTILISVFQDFLFTHECEQS
C-C CKR-2  RCRNEKKRHRAVRVIFTIMIVYFLFWTPYNIVILLNTFQEFFGLSNCEST
C-C CKR-3  RCPSKKK-YKAIRLIFVIMAVFFIFWTPYNVAILLSSYQSILFGNDCERS
C-C CKR-4  HCKNEKK-NKAVKMIFAVVVLFLGFWTPYNIVLFLETLVELEVLQDCTFE
             .   ...*  ..  ...  *.***. ...             .*

M/DC CR    YNLDKSVHITKLIATTHCCINPLLYAFLDGTFSKYLCRCFH---------
C-C CKR-1  RHLDLAVQVTEVIAYTHCCVNPVIYAFVGERFRKYLRQLFH-RRVA----
C-C CKR-2  SQLDQATQVTETLGMTHCCINPIIYAFVGEKFRSLFHIALG-CRIAPLQK
C-C CKR-3  KHLDLVMLVTEVIAYSHCCMNPVIYAFVGERFRKYLRHFFH-RHLL----
C-C CKR-4  RYLDYAIQATETLAFVHCCLNPIIYFFLGEKFRKYILQLFKTCRGLFVLC
            **      *   ..  ***.**...* *..  *   .   .

M/DC CR    ---------------LRSNTPLQPRGQSAQGTSREEP--DHSTEV*
C-C CKR-1  -------VHLVKWLPFLSVDRLERVSSTSPSTGEHELSA----GF*
C-C CKR-2  PVCGGPGVRPGKNVKVTTQGLLDGRGKGKSIGRAPEASLQDKEGA*
C-C CKR-3  -------MHLGRYIPFLPSEKLERTSSVSPSTAEPELSI----VF*
C-C CKR-4  QYCG--------LLQIYSAD------TPSSSYTQSTMDHDLHDAL*
```

As used herein, the term "TECK" shall encompass, when used in a protein context, a protein having mature mouse or human amino acid sequences, as shown in Table 1. The invention also embraces a polypeptide comprising a significant fragment of such protein. It also refers to a polypeptide which is a species counterpart, e.g., which exhibits similar biological function, and is more homologous in natural encoding sequence than other genes from that species. Typically, such chemokine will also interact with its specific binding components, e.g., receptor. These binding components, e.g., antibodies, typically bind to the chemokine with high affinity, e.g., at least about 100 nM, usually better than about 30 nM, preferably better than about 10 nM, and more preferably at better than about 3 nM. Homologous proteins would be found in mammalian species other than mouse, e.g., rats, dogs, cats, and primates. Non-mammalian species should also possess structurally or functionally related genes and proteins.

The term "polypeptide" as used herein includes a significant fragment or segment, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., about 35, 40, 45, 50, 60, 75, 80, 100, 120, etc. Similar proteins will likely comprise a plurality of such segments. Such fragments may have ends which begin and/or end at virtually all positions, e.g., beginning at residues 1, 2, 3, etc., and ending at, e.g., 69, 68, 67, 66, etc., in all combinations. Particularly interesting peptides have ends corresponding to structural domain boundaries. See, e.g., PHD and DSC programs, Rost and Sander (1994) *Proteins* 19:55-72; and King and Sternberg (1996) *Protein Science* 5:2298-2310.

The term "binding composition" refers to molecules that bind with specificity to the respective chemokine or receptor, e.g., in a ligand-receptor type fashion or an antibody-antigen interaction. These compositions may be compounds, e.g., proteins, which specifically associate with the chemokine or receptor, including natural physiologically relevant protein-protein interactions, either covalent or non-covalent. The binding composition may be a polymer, or another chemical reagent. No implication as to whether the chemokine presents a concave or convex shape in its ligand-receptor interaction is represented, other than the interaction exhibit similar specificity, e.g., specific affinity. A functional analog may be a ligand with structural modifications, or may be a wholly unrelated molecule, e.g., which has a molecular shape which interacts with the appropriate ligand binding determinants. The ligands may serve as agonists or antagonists of the receptor, see, e.g., Goodman, et al. (eds.) (1990) *Goodman & Gilman's: The Pharmacological Bases of Therapeutics* (8th ed.), Pergamon Press.

Substantially pure means that the protein is free from other contaminating proteins, nucleic acids, and/or other biologicals typically derived from the original source organism. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, and in most preferred embodiments, at least 99% pure. Analyses will typically be by weight, but may be by molar amounts.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified, e.g., to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS, or a low enough concentration as to avoid significant disruption of structural or physiological properties of the protein.

Solubility is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W.H. Freeman; and Cantor and Schimmel (1980) *Biophysical Chemistry*, parts 1-3, W.H. Freeman & Co., San Francisco. As a crude determination, a sample containing a putatively soluble polypeptide is spun in a standard full sized ultracentrifuge at about 50 K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

III. Physical Variants

This invention also encompasses proteins or peptides having substantial amino acid sequence homology with the amino acid sequence of each respective chemokine or receptor. The variants include species or polymorphic variants.

Amino acid sequence homology, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25-100% homology (if gaps can be introduced), to 50-100% homology (if conservative substitutions are included) with the amino acid sequence of the appropriate chemokine or receptor. Homology measures will be at least about 35%, generally at least 40%, more generally at least 45%, often at least 50%, more often at least 55%, typically at least 60%, more typically at least 65%, usually at least 70%, more usually at least 75%, preferably at least 80%, and more preferably at least 80%, and in particularly preferred embodiments, at least 85% or more. See also Needleham, et al. (1970) *J. Mol. Biol.* 48:443-453; Sankoff, et al. (1983) Chapter One in *Time Warps, String Edits, and Macromolecules: The Theory and Practice of Sequence Comparison* Addison-Wesley, Reading, Mass.; and software packages from IntelliGenetics, Mountain View, Calif.; and the University of Wisconsin Genetics Computer Group, Madison, Wis.

Each of the isolated chemokine or receptor DNAs can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, or antigenic activity. These modified sequences can be used to produce mutant antigens or to enhance expression. Enhanced expression may involve gene amplification, increased transcription, increased translation, and other mechanisms. Such mutant chemokine or receptor derivatives include predetermined or site-specific mutations of the respective protein or its fragments. "Mutant chemokine" encompasses a polypeptide otherwise falling within the homology definition of the chemokine as set forth above, but having an amino acid sequence which differs from that of the chemokine as found in nature, whether by way of deletion, substitution, or insertion. These include substitution levels from none, one, two, three, etc. In particular, "site specific mutant chemokine" generally includes proteins having significant homology with a ligand having sequences of Table 1 through 3, and as sharing various biological activities, e.g., antigenic or immunogenic, with those sequences, and in preferred embodiments contain most of the disclosed sequences. Similar concepts apply to the different chemokine protein embodiments, particularly those found in various warm blooded animals, e.g., mammals and birds. As stated before, it is emphasized that descriptions are generally meant to encompass the various chemokine proteins, not limited to the mouse or human embodiments specifically discussed. Similar concepts apply to the receptor embodiments.

Although site specific mutation sites are often predetermined, mutants need not be site specific. Chemokine mutagenesis can be conducted by making amino acid insertions or deletions. Substitutions, deletions, insertions, or combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an immunoglobulin with a chemokine or receptor polypeptide is a continuous protein molecule having sequences fused in a typical peptide linkage, typically made as a single translation product and exhibiting properties derived from each source peptide. A similar chimeric concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992. Thus, new chimeric polypeptides exhibiting new combinations of specificities will result from the functional linkage of ligand-binding specificities and other functional domains.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

IV. Functional Variants

The blocking of physiological response to various embodiments of these chemokines may result from the inhibition of binding of the ligand to its receptor, likely through competitive inhibition. Thus, in vitro assays of the present invention will often use isolated protein, membranes from cells expressing a recombinant membrane associated chemokine, soluble fragments comprising receptor binding segments of these ligands, or fragments attached to solid phase substrates. These assays will also allow for the diagnostic determination of the effects of either binding segment mutations and modifications, or ligand mutations and modifications, e.g., ligand analogs.

This invention also contemplates the use of competitive drug screening assays, e.g., where neutralizing antibodies to antigen or receptor fragments compete with a test compound for binding to the protein. In this manner, the antibodies can be used to detect the presence of polypeptides which share one or more antigenic binding sites of the ligand and can also be used to occupy binding sites on the protein that might otherwise interact with a receptor.

Additionally, neutralizing antibodies against a specific chemokine embodiment and soluble fragments of the chemokine which contain a high affinity receptor binding site, can be used to inhibit chemokine activity in tissues, e.g., tissues experiencing abnormal physiology.

"Derivatives" of chemokine antigens include amino acid sequence mutants, glycosylation variants, and covalent or aggregate conjugates with other chemical moieties. Covalent derivatives can be prepared by linkage of functionalities to groups which are found in chemokine amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the respective chemokine or receptor or fragments thereof with other proteins or polypeptides. These derivatives can be synthesized in recombinant culture such as N- or C-terminal fusions or by the use of agents known in the art for their usefulness in cross-linking proteins through reactive side groups. Preferred chemokine derivatization sites with cross-linking agents are at free amino groups, carbohydrate moieties, and cysteine residues.

Fusion polypeptides between these chemokines and other homologous or heterologous proteins, e.g., other chemokines, are also provided. Many growth factors and cytokines are homodimeric entities, and a repeat construct may have various advantages, including lessened susceptibility to proteolytic cleavage. Moreover, many receptors require dimerization to transduce a signal, and various dimeric ligands or domain repeats can be desirable. Homologous polypeptides may be fusions between different surface markers, resulting in, e.g., a hybrid protein exhibiting receptor binding specificity. Likewise, heterologous fusions may be constructed which would exhibit a combination of properties or activities of the derivative proteins. Typical examples are fusions of a reporter polypeptide, e.g., luciferase, with a segment or domain of a ligand, e.g., a receptor-binding segment, so that the presence or location of the fused ligand may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, a FLAG fusion, and yeast alpha mating factor. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity tags as FLAG.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1-3, Cold Spring Harbor Laboratory. Techniques for synthesis of polypeptides are described, for example, in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Approach*, IRL Press, Oxford; and chemical ligation, e.g., Dawson, et al. (1994) *Science* 266:776-779, a method of linking long synthetic peptides by a peptide bond.

This invention also contemplates the use of derivatives of these chemokines or receptors other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a chemokine antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-chemokine antibodies or its receptor. These chemokines can also be labeled with a detectable group, for example radioiodinated by the chloramine T procedure, covalently bound to rare earth chelates, or conjugated to a fluorescent moiety for use in diagnostic assays. Purification of chemokine may be effected by immobilized antibodies or receptor.

Other modifications may be introduced with the goal of modifying the therapeutic pharmacokinetics or pharmacodynamics of a target chemokine. For example, certain means to minimize the size of the entity may improve its pharmacoaccessibility; other means to maximize size may affect pharmacodynamics.

A solubilized chemokine or appropriate fragment of this invention can be used as an immunogen for the production of antisera or antibodies specific for the ligand or fragments thereof. The purified chemokines can be used to screen monoclonal antibodies or chemokine-binding fragments prepared by immunization with various forms of impure preparations containing the protein. In particular, antibody equivalents include antigen binding fragments of natural antibodies, e.g., Fv, Fab, or $F(ab)_2$. Purified chemokines can also be used as a reagent to detect antibodies generated in response to the presence of elevated levels of the protein or cell fragments containing the protein, both of which may be diagnostic of an abnormal or specific physiological or disease condition. Additionally, chemokine protein fragments, or their concatenates, may also serve as immunogens to produce antibodies of the present invention, as described immediately below. For example, this invention contemplates antibodies raised against amino acid sequences shown in Tables 1 through 3, or proteins containing them. In particular, this invention contemplates antibodies having binding affinity to or being raised against specific fragments, e.g., those which are predicted to lie on the outside surfaces of protein tertiary structure. Similar concepts apply to antibodies specific for receptors of the invention.

The present invention contemplates the isolation of additional closely related species variants. Southern and Northern blot analysis should establish that similar genetic entities exist in other mammals, and establish the stringency of hybridization conditions to isolate such. It is likely that these chemokines and receptors are widespread in species variants, e.g., rodents, lagomorphs, carnivores, artiodactyla, perissodactyla, and primates.

The invention also provides means to isolate a group of related chemokines displaying both distinctness and similarities in structure, expression, and function. Elucidation of many of the physiological effects of the proteins will be greatly accelerated by the isolation and characterization of distinct species variants of the ligands. In particular, the present invention provides useful probes for identifying additional homologous genetic entities in different species.

The isolated genes will allow transformation of cells lacking expression of a corresponding chemokine, e.g., either species types or cells which lack corresponding ligands and exhibit negative background activity. Expression of transformed genes will allow isolation of antigenically pure cell lines, with defined or single specie variants. This approach will allow for more sensitive detection and discrimination of the physiological effects of chemokine receptor proteins. Subcellular fragments, e.g., cytoplasts or membrane fragments, can be isolated and used.

Dissection of critical structural elements which effect the various differentiation functions provided by ligands is possible using standard techniques of modern molecular biology, particularly in comparing members of the related class. See, e.g., the homolog-scanning mutagenesis technique described in Cunningham, et al. (1989) *Science* 243: 1339-1336; and approaches used in O'Dowd, et al. (1988) *J. Biol. Chem.* 263:15985-15992; and Lechleiter, et al. (1990) *EMBO J.* 9:4381-4390.

In addition, receptor binding segments can be substituted between species variants to determine what structural features are important in both receptor binding affinity and specificity, as well as signal transduction. An array of different chemokine variants will be used to screen for ligands exhibiting combined properties of interaction with different receptor species variants.

Intracellular functions would probably involve segments of the receptor which are normally accessible to the cytosol. However, ligand internalization may occur under certain circumstances, and interaction between intracellular components and "extracellular" segments may occur. The specific segments of interaction of a particular chemokine with other intracellular components may be identified by mutagenesis or direct biochemical means, e.g., cross-linking or affinity methods. Structural analysis by crystallographic or other physical methods will also be applicable. Further investigation of the mechanism of signal transduction will include study of associated components which may be isolatable by affinity methods or by genetic means, e.g., complementation analysis of mutants.

Further study of the expression and control of the various chemokines will be pursued. The controlling elements associated with the proteins may exhibit differential developmental, tissue specific, or other expression patterns. Upstream or downstream genetic regions, e.g., control elements, are of interest. Differential splicing of message may lead to membrane bound forms, soluble forms, and modified versions of ligand.

Structural studies of the proteins will lead to design of new ligands, particularly analogs exhibiting agonist or antagonist properties on the receptor. This can be combined with previously described screening methods to isolate ligands exhibiting desired spectra of activities.

Expression in other cell types will often result in glycosylation differences in a particular chemokine. Various species variants may exhibit distinct functions based upon structural differences other than amino acid sequence. Differential modifications may be responsible for differential function, and elucidation of the effects are now made possible.

Thus, the present invention provides important reagents related to a physiological chemokine-binding protein interaction. Although the foregoing description has focused primarily upon the mouse and human embodiments of the chemokines specifically described, those of skill in the art will immediately recognize that the invention provides other species counterparts, e.g., rat and other mammalian species or allelic or polymorphic variants.

V. Antibodies

Antibodies can be raised to these chemokines, including species or polymorphic variants, and fragments thereof, both in their naturally occurring forms and in their recombinant forms. Additionally, antibodies can be raised to chemokines in either their active forms or in their inactive forms. Anti-idiotypic antibodies are also contemplated.

Antibodies, including binding fragments and single chain versions, against predetermined fragments of the ligands can be raised by immunization of animals with concatemers or conjugates of the fragments with immunogenic proteins. Monoclonal antibodies are prepared from cells secreting the desired antibody. These antibodies can be screened for binding to normal or defective chemokines, or screened for agonistic or antagonistic activity, e.g., mediated through a receptor for a chemokine. These monoclonal antibodies will usually bind with at least a $K_D$ of about 1 mM, more usually at least about 300 μM, typically at least about 10 μM, more typically at least about 30 μM, preferably at least about 10 μM, and more preferably at least about 3 μM or better.

The antibodies, including antigen binding fragments, of this invention can have significant diagnostic or therapeutic value. They can be potent antagonists that bind to ligand and inhibit binding to receptor or inhibit the ability of a ligand to elicit a biological response. They also can be useful as non-neutralizing antibodies and can be coupled to toxins or radionuclides so that when the antibody binds to ligand, a cell expressing it, e.g., on its surface via receptor, is killed. Further, these antibodies can be conjugated to drugs or other therapeutic agents, either directly or indirectly by means of a linker, and may effect drug targeting. Antibodies to receptors may be more easily used to block ligand binding and signal transduction.

The antibodies of this invention can also be useful in diagnostic or reagent purification applications. As capture or non-neutralizing antibodies, they can be screened for ability to bind to the chemokines without inhibiting receptor binding. As neutralizing antibodies, they can be useful in competitive binding assays. They will also be useful in detecting or quantifying chemokine or, indirectly, receptors, e.g., in immunoassays. They may be used as purification reagents in immunoaffinity columns or as immunohistochemistry reagents.

Ligand fragments may be concatenated or joined to other materials, particularly polypeptides, as fused or covalently joined polypeptides to be used as immunogens. Short peptides will preferably be made as repeat structures to increase size. A ligand and its fragments may be fused or covalently linked to a variety of immunogens, such as keyhole limpet hemocyanin, bovine serum albumin, tetanus toxoid, etc. See *Microbiology*, Hoeber Medical Division, Harper and Row, 1969; Landsteiner (1962) *Specificity of Serological Reactions*, Dover Publications, New York, and Williams, et al. (1967) *Methods in Immunology and Immunochemistry*, Vol. 1, Academic Press, New York, for descriptions of methods of preparing polyclonal antisera. A typical method involves hyperimmunization of an animal with an antigen. The blood of the animal is then collected shortly after the repeated immunizations and the gamma globulin fraction is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495-497, which discusses one method of generating monoclonal antibodies. Summarized briefly, this method involves injecting an animal with an immunogen. The animal is then sacrificed and cells taken, e.g., from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance. Large amounts of antibody may be derived from ascites fluid from an animal.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," Science 246:1275-1281; and Ward, et al. (1989) Nature 341:544-546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567; and Queen et al. (1989) Proc. Nat'l. Acad. Sci. 86:10029-10033.

The antibodies of this invention can also be used for affinity chromatography in isolating the protein. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified chemokine protein will be released.

The antibodies may also be used to screen expression libraries for particular expression products. Usually the antibodies used in such a procedure will be labeled with a moiety allowing easy detection of presence of antigen by antibody binding.

Antibodies raised against these chemokine will also be useful to raise anti-idiotypic antibodies. These will be useful in detecting or diagnosing various immunological conditions related to expression of the respective antigens.

VI. Nucleic Acids

The described peptide sequences and the related reagents are useful in isolating a DNA clone encoding these chemokines, e.g., from a natural source. Typically, it will be useful in isolating a gene from another individual, and similar procedures will be applied to isolate genes from other species, e.g., warm blooded animals, such as birds and mammals. Cross hybridization will allow isolation of ligand from other species. A number of different approaches should be available to successfully isolate a suitable nucleic acid clone. Similar concepts apply to the receptor embodiments.

The purified protein or defined peptides are useful for generating antibodies by standard methods, as described above. Synthetic peptides or purified protein can be presented to an immune system to generate monoclonal or polyclonal antibodies. See, e.g., Coligan (1991) Current Protocols in Immunology Wiley/Greene; and Harlow and Lane (1989) Antibodies: A Laboratory Manual Cold Spring Harbor Press. Alternatively, a chemokine receptor can be used as a specific binding reagent, and advantage can be taken of its specificity of binding, much like an antibody would be used. However, chemokine receptors are typically 7 transmembrane proteins, which could be sensitive to appropriate interaction with lipid or membrane. The signal transduction typically is mediated through a G-protein.

For example, the specific binding composition could be used for screening of an expression library made from a cell line which expresses a particular chemokine. The screening can be standard staining of surface expressed ligand, or by panning. Screening of intracellular expression can also be performed by various staining or immunofluorescence procedures. The binding compositions could be used to affinity purify or sort out cells expressing the ligand.

The peptide segments can also be used to predict appropriate oligonucleotides to screen a library, e.g., to isolate species variants. The genetic code can be used to select appropriate oligonucleotides useful as probes for screening. See, e.g., Tables 1 through 5. In combination with polymerase chain reaction (PCR) techniques, synthetic oligonucleotides will be useful in selecting correct clones from a library. Complementary sequences will also be used as probes or primers. Based upon identification of the likely amino terminus, the third peptide should be particularly useful, e.g., coupled with anchored vector or poly-A complementary PCR techniques or with complementary DNA of other peptides.

This invention contemplates use of isolated DNA or fragments to encode a biologically active corresponding chemokine polypeptide. In addition, this invention covers isolated or recombinant DNA which encodes a biologically active protein or polypeptide which is capable of hybridizing under appropriate conditions with the DNA sequences described herein. Said biologically active protein or polypeptide can be an intact ligand, or fragment, and have an amino acid sequence as disclosed in Tables 1 through 3. Further, this invention covers the use of isolated or recombinant DNA, or fragments thereof, which encode proteins which are homologous to a chemokine or which was isolated using cDNA encoding a chemokine as a probe. The isolated DNA can have the respective regulatory sequences in the 5' and 3' flanks, e.g., promoters, enhancers, poly-A addition signals, and others. Alternatively, promoters or other regulatory signals may be incorporated to be operably linked to natural genes in a cell.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 20 nucleotides, more generally at least about 23 nucleotides, ordinarily at least about 26 nucleotides, more ordinarily at least about 29 nucleotides, often at least about 32 nucleotides, more often at least about 35 nucleotides, typically at least about 38 nucleotides, more typically at least about 41 nucleotides, usually at least about 44 nucleotides, more usually at least about 47 nucleotides, preferably at least about 50 nucleotides, more preferably at least about 53 nucleotides, and in particularly preferred embodiments will be at least about 56 or more nucleotides, e.g., 60, 65, 75, 85, 100, 120, 150, 200, 250, 300, 400, etc. Such fragments may have ends which begin and/or end at virtually all positions, e.g., beginning at nucleotides 1, 2, 3, etc., and ending at, e.g., 300, 299, 298, 287, etc., in all combinations. Particularly interesting polynucleotides have ends corresponding to structural domain boundaries.

A DNA which codes for a particular chemokine protein or peptide will be very useful to identify genes, mRNA, and cDNA species which code for related or homologous ligands, as well as DNAs which code for homologous proteins from different species. There are likely homologs in other species, including primates. Various chemokine proteins should be homologous and are encompassed herein. However, even proteins that have a more distant evolutionary relationship to the ligand can readily be isolated under appropriate conditions using these sequences if they are sufficiently homologous. Primate chemokines are of particular interest.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Alternatively, recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology Academic Press*, San Diego, pp. 1502-1504; Travis (1992) *Science* 256:1392-1394; Kuhn, et al. (1991) *Science* 254:707-710; Capecchi (1989) *Science* 244:1288; Robertson (1987)(ed.) *Teratocarcinomas and Embryonic Stem Cells: A Practical Approach* IRL Press, Oxford; and Rosenberg (1992) *J. Clinical Oncology* 10:180-199.

Homologous nucleic acid sequences, when compared, exhibit significant similarity, or identity. The standards for homology in nucleic acids are either measures for homology generally used in the art by sequence comparison or based upon hybridization conditions. The hybridization conditions are described in greater detail below.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 56%, more generally at least about 59%, ordinarily at least about 62%, more ordinarily at least about 65%, often at least about 68%, more often at least about 71%, typically at least about 74%, more typically at least about 77%, usually at least about 80%, more usually at least about 85%, preferably at least about 90%, more preferably at least about 95 to 98% or more, and in particular embodiments, as high at about 99% or more of the nucleotides. Alternatively, substantial homology exists when the segments will hybridize under selective hybridization conditions, to a strand, or its complement, typically using a sequence derived from Tables 1 through 5. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, Kanehisa (1984) *Nuc. Acids Res.* 12:203-213. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., more usually in excess of about 37° C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349-370.

Corresponding chemokines from other mammalian species can be cloned and isolated by cross-species hybridization of closely related species. Alternatively, sequences from a data base may be recognized as having similarity. Homology may be relatively low between distantly related species, and thus hybridization of relatively closely related species is advisable. Alternatively, preparation of an antibody preparation which exhibits less species specificity may be useful in expression cloning approaches. PCR approaches using segments of conserved sequences will also be used.

VII. Making Chemokines, Receptors; Mimetics

DNA which encodes each respective chemokine or fragments thereof can be obtained by chemical synthesis, screening cDNA libraries, or by screening genomic libraries prepared from a wide variety of cell lines or tissue samples.

This DNA can be expressed in a wide variety of host cells for the synthesis of a full-length ligand or fragments which can in turn, for example, be used to generate polyclonal or monoclonal antibodies; for binding studies; for construction and expression of modified molecules; and for structure/function studies. Each antigen or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, or portions thereof, may be expressed as fusions with other proteins.

Expression vectors are typically self-replicating DNA or RNA constructs containing the desired antigen gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encode embodiments of a chemokine, receptor, or a fragment thereof, typically encoding a biologically active polypeptide. The DNA can be under the control of a viral promoter and can encode a selection marker. This invention further contemplates use of such expression vectors which are capable of expressing eukaryotic cDNA coding for each chemokine in a prokaryotic or eukaryotic host, where the vector is compatible with the host and where the eukaryotic cDNA coding for the ligand is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the ligand or its fragments in various hosts using vectors that do not contain a replication origin that is recognized by the host cell. It is also possible to use vectors that cause integration of a chemokine gene or its fragments into the host DNA by recombination, or to integrate a promoter which controls expression of an endogenous gene.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (1988) (eds.) *Vectors: A Survey of Molecular Cloning Vectors and Their Uses*, Buttersworth, Boston, Mass.

Transformed cells include cells, preferably mammalian, that have been transformed or transfected with a chemokine gene containing vector constructed using recombinant DNA techniques. Transformed host cells usually express the ligand or its fragments, but for purposes of cloning, amplifying, and manipulating its DNA, do not need to express the protein. This invention further contemplates culturing transformed cells in a nutrient medium, thus permitting the protein to accumulate in the culture. The protein can be recovered, either from the culture or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia*, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express these chemokines or their fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses*, Buttersworth, Boston, Chapter 10, pp. 205-236.

Lower eukaryotes, e.g., yeasts and Dictyostelium, may be transformed with chemokine sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are the preferred host cells for expression of the functionally active chemokine protein. In principle, most any higher eukaryotic tissue culture cell line is workable, e.g., insect baculovirus expression systems, whether from an invertebrate or vertebrate source. However, mammalian cells are preferred, in that the processing, both cotranslationally and posttranslationally. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1; pCD, see Okayama, et al. (1985) *Mol. Cell Biol.* 5:1136-1142; pMC1neo Poly-A, see Thomas, et al. (1987) *Cell* 51:503-512; and a baculovirus vector such as pAC 373 or pAC 610.

It will often be desired to express a chemokine polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, a chemokine gene may be co-transformed with one or more genes encoding mammalian or other glycosylating enzymes. Using this approach, certain mammalian glycosylation patterns will be achievable or approximated in prokaryote or other cells.

A chemokine, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427-454; Tse, et al. (1985) *Science* 230:1003-1008; and Brunner, et al. (1991) *J. Cell Biol.* 114:1275-1283.

Now that these chemokines have been characterized, fragments or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszky (1984) *The Practice of Peptide Synthesis*, Springer-Verlag, New York; and Bodanszky (1984) *The Principles of Peptide Synthesis*, Springer-Verlag, New York. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

These chemokines, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction are typically protected to prevent coupling at an incorrect location.

If a solid phase synthesis is adopted, the C-terminal amino acid is typically bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonyl-hydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156.

The prepared ligand and fragments thereof can be isolated and purified from the reaction mixture by means of peptide separation, e.g., by extraction, precipitation, electrophoresis and various forms of chromatography, and the like. The various chemokines of this invention can be obtained in varying degrees of purity depending upon its desired use. Purification can be accomplished by use of the protein purification techniques disclosed herein or by the use of the antibodies herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the ligand, or lysates or supernatants of cells producing the desired chemokine as a result of DNA techniques, see below.

VIII. Uses

The present invention provides reagents which will find use in diagnostic applications as described elsewhere herein, e.g., in the general description for developmental abnormalities, or below in the description of kits for diagnosis.

This invention also provides reagents with significant therapeutic value. These chemokines (naturally occurring or recombinant), fragments thereof and antibodies thereto, along with compounds identified as having binding affinity to them, should be useful in the treatment of conditions associated with abnormal physiology or development, including inflammatory conditions, including asthma. In particular, modulation of trafficking of leukocytes is one likely biological activity, but a wider tissue distribution might suggest broader biological activity, including, e.g., antiviral effects. Abnormal proliferation, regeneration, degeneration, and atrophy may be modulated by appropriate therapeutic treatment using the compositions provided herein. For example, a disease or disorder associated with abnormal expression or abnormal signaling by a chemokine should be a likely target for an agonist or antagonist of the ligand.

Various abnormal physiological or developmental conditions are known in cell types shown to possess the chemokine mRNAs by Northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions which may be susceptible to prevention or treatment using compositions provided herein.

Chemokine antibodies, including recombinant forms, can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding. Moreover, modifications to the antibody molecules or antigen binding fragments thereof, may be adopted which affect the pharmacokinetics or pharmacodynamics of the therapeutic entity.

Drug screening using antibodies or receptor or fragments thereof can be performed to identify compounds having binding affinity to each chemokine or receptor, including isolation of associated components. Subsequent biological assays can then be utilized to determine if the compound has intrinsic stimulating activity and is therefore a blocker or antagonist in that it blocks the activity of the ligand. Likewise, a compound having intrinsic stimulating activity can activate the receptor and is thus an agonist in that it simulates the activity of a chemokine. This invention further contemplates the therapeutic use of antibodies to these chemokines as antagonists. This approach should be particularly useful with other chemokine species variants.

The quantities of reagents necessary for effective therapy will depend upon many different factors, including means of administration, target site, physiological state of the patient, and other medicants administered. Thus, treatment dosages should be titrated to optimize safety and efficacy in various populations, including racial subgroups, age, gender, etc. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers typically include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

A chemokine, fragments thereof, or antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is often preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Carriers may improve storage life, stability, etc. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics*, 8th Ed., Pergamon Press; and *Remington's Pharmaceutical Sciences*, 17th ed. (1990), Mack Publishing Co., Easton, Pa.; Avis, et al. (eds.) (1993) *Pharmaceutical Dosage Forms: Parenteral Medications* Dekker, New York; Lieberman, et al. (eds.) (1990) *Pharmaceutical Dosage Forms: Tablets* Dekker, New York; and Lieberman, et al. (eds.) (1990) *Pharmaceutical Dosage Forms: Disperse Systems* Dekker, New York. The therapy of this invention may be combined with or used in association with other therapeutic agents.

Both the naturally occurring and the recombinant forms of the chemokines of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767-773, which describes means for testing of binding affinity by a plurality of defined polymers synthesized on a solid substrate. The development of suitable assays can be greatly facilitated by the availability of large amounts of purified, soluble chemokine as provided by this invention.

For example, antagonists can normally be found once the ligand has been structurally defined. Testing of potential ligand analogs is now possible upon the development of highly automated assay methods using physiologically responsive cells. In particular, new agonists and antagonists will be discovered by using screening techniques described herein.

Viable cells could also be used to screen for the effects of drugs on respective chemokine mediated functions, e.g., second messenger levels, i.e., $Ca^{++}$; inositol phosphate pool changes (see, e.g., Berridge (1993) *Nature* 361:315-325 or Billah and Anthes (1990) *Biochem. J.* 269:281-291); cellular morphology modification responses; phosphoinositide lipid turnover; an antiviral response. and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus.

Rational drug design may also be based upon structural studies of the molecular shapes of the chemokines and other effectors or analogs. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

Purified chemokine can be coated directly onto plates for use in the aforementioned drug screening techniques. However, non-neutralizing antibodies to these ligands can be used as capture antibodies to immobilize the respective ligand on the solid phase.

Similar concepts also apply to the chemokine receptor embodiments of the invention.

IX. Kits

This invention also contemplates use of chemokine proteins, fragments thereof, peptides, and their fusion products in a variety of diagnostic kits and methods for detecting the presence of ligand, antibodies, or chemokine receptors. Typically the kit will have a compartment containing either a defined chemokine peptide or gene segment or a reagent which recognizes one or the other, e.g., antibodies.

A kit for determining the binding affinity of a test compound to a chemokine would typically comprise a test compound; a labeled compound, for example an antibody having known binding affinity for the ligand; a source of chemokine (naturally occurring or recombinant); and a means for separating bound from free labeled compound, such as a solid phase for immobilizing the ligand. Once compounds are screened, those having suitable binding affinity to the ligand can be evaluated in suitable biological assays, as are well known in the art, to determine whether they act as agonists or antagonists to the receptor. The availability of recombinant chemokine polypeptides also provide well defined standards for calibrating such assays or as positive control samples.

A preferred kit for determining the concentration of, for example, a chemokine in a sample would typically comprise a labeled compound, e.g., antibody, having known binding affinity for the ligand, a source of ligand (naturally occurring or recombinant) and a means for separating the bound from free labeled compound, for example, a solid phase for immobilizing the chemokine. Compartments containing reagents, and instructions for use or disposal, will normally be provided.

Antibodies, including antigen binding fragments, specific for the chemokine or ligand fragments are useful in diagnostic applications to detect the presence of elevated levels of chemokine and/or its fragments. Such diagnostic assays can employ lysates, live cells, fixed cells, immunofluorescence, cell cultures, body fluids, and further can involve the detection of antigens related to the ligand in serum, or the like. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a chemokine or to a particular fragment thereof. Similar assays have also been extensively discussed in the literature. See, e.g., Harlow and Lane (1988) *Antibodies: A Laboratory Manual*, CSH.

Anti-idiotypic antibodies may have similar uses to diagnose presence of antibodies against a chemokine, as such may be diagnostic of various abnormal states. For example, overproduction of a chemokine may result in production of various immunological reactions which may be diagnostic of abnormal physiological states, particularly in various inflammatory or asthma conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled chemokine is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

The aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, chemokine, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating bound from the free ligand, or alternatively bound from free test compound. The chemokine can be immobilized on various matrixes followed by washing. Suitable matrixes include plastic such as an ELISA plate, filters, and beads. Methods of immobilizing the chemokine to a matrix include, without limitation, direct adhesion to plastic, use of a capture antibody, chemical coupling, and biotin-avidin. The last step in this approach involves the precipitation of ligand/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457-1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a chemokine. These sequences can be used as probes for detecting levels of the ligand message in samples from patients suspected of having an abnormal condition, e.g., an inflammatory or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}P$. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

X. Receptor

Having isolated a ligand binding partner of a specific interaction, methods exist for isolating the counter-partner. See, Gearing, et al *EMBO J.* 8:3667-4676 or McMahan, et al. (1991) *EMBO J.* 10:2821-2832. For example, means to label a chemokine without interfering with the binding to its receptor can be determined. For example, an affinity label can be fused to either the amino- or carboxy-terminus of the ligand. An expression library can be screened for specific binding of chemokine, e.g., by cell sorting, or other screening to detect subpopulations which express such a binding component. See, e.g., Ho, et al. (1993) *Proc. Nat'l Acad. Sci.* 90:11267-11271. Alternatively, a panning method may be used. See, e.g., Seed and Aruffo (1987) *Proc. Nat'l. Acad. Sci.* 84:3365-3369.

Protein cross-linking techniques with label can be applied to a isolate binding partners of a chemokine. This would allow identification of protein which specifically interacts with a chemokine, e.g., in a ligand-receptor like manner.

In various embodiments, new receptors designated DC CR and M/DC CR were isolated. The sequences of the human constructs and product are provided in Tables 4 and 5. Similar means for making variants and fragments, at the nucleotide level or at the protein level, and making antibodies will be available as described above, directed primarily to the chemokine embodiments. Many similar or related uses to the ligands will be applied to the receptors, as specific binding reagents. In particular, methods will be applied to screening for specific ligands for each receptor. Many uses, including kits, will also be available through analogous techniques.

The broad scope of this invention is best understood with reference to the following examples, which are not intended to limit the invention to specific embodiments.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York; Innis, et al. (eds.)(1990) *PCR Protocols: A Guide to Methods and Applications* Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, N.Y.; and Crowe, et al. (1992) *QIAexpress: The High Level Expression & Protein Purification System* QUIAGEN, Inc., Chatsworth, Calif.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation and Characterization of Chemokine cDNAs

A. TECK

The TECK was isolated from a cDNA library made from thymus cells from a RAG-1 "knockout" mouse. See, Mombaerts, et al. (1992) *Cell* 68:869-877. Individual cDNA clones were sequenced using standard methods, e.g., the Taq DyeDeoxy Terminator Cycle Sequencing kit (Applied Biosystems, Foster City, Calif.), and the TECK sequence was identified and further characterized. Computer analyses with other C—C chemokine family members revealed significant homology at the amino acid levels with other chemokines. The nucleotide sequence for mouse is provided in Table 1, encoding a polypeptide of about 144 amino acids. The signal sequence should run from 1 (met) to about 23 (ala), and removal of the signal sequence should provide one natural mature sequence beginning at 24 (gln). Additional processing may occur in a physiological system.

The sequence is notable in having a longer carboxy-terminal tail than most other CC chemokines. TECK exhibits one glycosylation site, and several AAMP, PKC, and CK2 phosphorylation sites.

B. MIP-3α

The MIP-3α was isolated from a cDNA library made from human monocytes activated with LPS and IFN-γ Individual cDNA clones were sequenced using standard methods, and the MIP-3α sequence was identified and further characterized. The nucleotide sequence is provided in Table 2, encoding a polypeptide of at least about 89 amino acids. The signal sequence should run from about 1 (met) to 21 (cys), and removal of the signal sequence should provide one natural sequence beginning with gly. Additional processing may occur in a physiological system.

C. MIP-3β

The MIP-3β was isolated from a cDNA library made from human fetal lung cells. Individual cDNA clones are sequenced using standard methods, and the MIP-3α sequence was identified and further characterized. The nucleotide sequence is provided in Table 3, encoding a polypeptide of about 98 amino acids. The signal sequence should run from about 1 (met) to about 21 (ser), and removal of the signal sequence should provide one mature natural sequence beginning from gly. Additional processing may occur in a physiological system.

This chemokine has been paired with a receptor designated Ebi1. See Yoshida, et al. (1997) *J. Biol. Chem.* 13803-13809.

D. Dendritic Cell Receptor for Chemokine; DC CR

The DC CR was isolated from RNA made from dendritic cells isolated from CD34+ cord blood cells, isolated by standard procedure. It was also isolated from eosinophils using degenerate PCR primers of the TM2 and TM7 segments, which are often conserved among chemokine receptors. These eosinophils were isolated by taking PBLs, depletion of red blood cells by lysis, and negative selection of CD16 to remove neutrophils.

Sequencing of the PCR fragments indicated a potential novel receptor, and the fragment was used to isolate a full length clone by hybridization. Clone isolates were sequenced using standard methods, and the DC CR sequence was identified and further characterized. The nucleotide sequence is provided in Table 4, encoding a polypeptide of about 365 amino acids. The transmembrane segments, determined by homology to the IL-8 B receptor, are about: TM1 from 39 (leu) to 64 (phe); TM2 from 76 (leu) to 96 (ser); TM3 from 111 (leu) to 132 (met); TM4 from 151 (thr) to 176 (phe); TM5 from 207 (gly) to 229 (val); TM6 from 246 (val) to 270 (ala); and TM7 from 291 (val) to 319 (leu). The amino terminal segment is probably an extracellular segment, and the others would be between TM2 and TM3; and TM4 and TM5; and TM6 and TM7. The intracellular segments should then run between TM1 and TM2; TM3 and TM4, TM5 and TM6, and the carboxy terminus from the end of TM7. Additional processing may occur in a physiological system.

The implication of chemokine receptors in retroviral infection suggest that the receptor may be critical for infection. Antibodies which block infection may be routinely screened, and developed for therapeutic uses.

E. Monocyte/Dendritic Cell Receptor for Chemokine; M/DC CR

The M/DC CR was isolated from a cDNA library made from human monocyte cells cultured for 2.5 to t h in medium containing IFN-γ (10 ng/ml), LPS (1 µg/ml), anti-IL-4 monoclonal antibody (5 µg/ml), and anti-IL-10 monoclonal antibody (5 µg/ml). Individual cDNA clones were sequenced using standard methods, and the M/DC CR sequence was identified and further characterized. The nucleotide sequence is provided in Table 5, encoding a polypeptide of about 356 amino acids. The transmembrane segments, should be about as follows: TM1 from 52 (leu) to 76 (val); TM2 from 86 (asn) to 107 (ala); TM3 from 117 (ile) to 138 (val); TM4 from 157 (val) to 182 (tyr); TM5 from 211 (phe) to 233 (val); TM6 from 251 (leu) to 275 (phe); and TM7 from 296 (ile) to 315 (leu). As for the DC CR, the amino terminal segment is probably an extracellular segment, and the others would be between TM2 and TM3; and TM4 and TM5; and TM6 and TM7. The intracellular segments should then run between TM1 and TM2; TM3 and TM4, TM5 and TM6, and the carboxy terminus from the end of TM7.

III. Preparation of Antibodies

Many standard methods are available for preparation of antibodies. For example, synthetic peptides may be prepared to be used as antigen, administered to an appropriate animal, and either polyclonal or monoclonal antibodies prepared. Short peptides, e.g., less than about 10 amino acids may be repeated, while longer peptides may be used alone or conjugated to a carrier. For example, with the M/DC CR, animals were immunized with peptides corresponding to amino acid sequences from 18-44 (starting with LAP and ending with KYD; a fragment towards the amino terminus) and from 183-204 (starting with KPQ and ending with PAD; corresponding to an extracellular loop), see SEQ ID NO: 13. Highest specificity will result when the polypeptides are selected from portions which are most unique, e.g., not form conserved sequence regions. The animals may be used to collect antiserum, or may be used to generate monoclonal antibodies.

Antiserum was determined useful for ELISA, and will be evaluated for utility as immunoprecipitation or Western blot analysis. Monoclonal antibodies will also be evaluated for those same uses.

The antibodies provided will be useful as immunoaffinity reagents, as detection reagents, for immunohistochemistry, and as therapeutic reagents.

IV. Assays for Chemotactic Activity of Chemokines.

Chemokine proteins are produced, e.g., in COS cells transfected with a plasmid carrying the chemokine cDNA by electroporation. See, Hara, et al. (1992) *EMBO J.* 10:1875-1884. Physical analytical methods may be applied, e.g., CD analysis, to compare tertiary structure to other chemokines to evaluate whether the protein has likely folded into an active conformation. After transfection, a culture supernatant is collected and subjected to bioassays. A mock control, e.g., a plasmid carrying the luciferase cDNA, is used. See, de Wet, et al. (1987) *Mol. Cell. Biol.* 7:725-757. A positive control, e.g., recombinant murine MIP-1α from R&D Systems (Minneapolis, Minn.), is typically used. Likewise, antibodies may be used to block the biological activities, e.g., as a control.

Lymphocyte migration assays are performed as previously described, e.g., in Bacon, et al. (1988) *Br. J. Pharmacol.* 95:966-974. Murine Th2 T cell clones, CDC-25 (see Tony, et al. (1985) *J. Exp. Med.* 161:223-241) and HDK-1 (see Cherwinski, et al. (1987) *J. Exp. Med.* 166:1229-1244), made available from R. Coffman and A. O'Garra (DNAX, Palo Alto, Calif.), respectively, are used as controls.

Ca2+ flux upon chemokine stimulation is measured according to the published procedure described in Bacon, et al. (1995) *J. Immunol.* 154:3654-3666.

Maximal numbers of migrating cells in response to MIP-1α typically occur at a concentration of $10^{-8}$ M, in agreement with original reports for CD4+ populations of human T cells. See Schall (1993) *J. Exp. Med.* 177:1821-1826. A dose-response curve is determined, preferably giving a characteristic bell shaped dose-response curve.

After stimulation with C—C chemokines, lymphocytes generally show a measurable intracellular Ca2+ flux. MIP-1α is capable of inducing immediate transients of calcium mobilization. Typically, the levels of chemokine used in these assays will be comparable to those used for the chemotaxis assays (1/1000 dilution of conditioned supernatants).

Retroviral infection assays have also been described, and recent description of certain chemokine receptors in retroviral infection processes may indicate that similar roles may apply to the DC CR and/or M/DC CR. See, e.g., Balter (1996) *Science* 272:1740 (describing evidence for chemokine receptors as coreceptors for HIV); and Deng, et al. (1996) *Nature* 381:661-666.

V. Expression Analysis of Chemokine/Receptor Genes

RNA blot and hybridization are performed according to the standard method in Maniatis, et al. (1982) *Molecular Cloning: A Laboratory Manual* Cold Spring Harbor Laboratory Press, Cold Spring Harbor, N.Y. An appropriate fragment of a cDNA fragment is selected for use as a probe. To verify the amount of RNA loaded in each lane, the substrate membrane is reprobed with a control cDNA, e.g., glyceraldehyde 3-phosphate dehydrogenase (G3PDH) cDNA (Clontech, Palo Alto Calif.).

Analysis of mRNA from the appropriate cell source using the probe will determine the natural size of message. It will also indicate whether different sized messages exist. The messages will be subject to analysis after isolation, e.g., by PCR or hybridization techniques.

Northern blot analysis may be performed on many different mRNA sources. However, in certain cases, cDNA libraries may be used to evaluate sources which are difficult to prepare. A "reverse Northern" uses cDNA inserts removed from vector, but multiplicity of bands may reflect either different sized messages, or may be artifact due to incomplete reverse transcription in the preparation of the cDNA library. In such instances, verification may be appropriate by standard Northern analysis.

Similarly, Southern blots may be used to evaluate species distribution of a gene. The stringency of washes of the blot will also provide information as to the extent of homology of various species counterparts.

Tissue distribution, and cell distribution, may be evaluated by immunohistochemistry using antibodies. Alternatively, in situ nucleic acid hybridization may also be used in such analysis.

A. TECK

The TECK was isolated from a RAG-1 "knockout" mouse. This animal is characterized by a great predominance of pro-T or pre-T cells, lacking more mature T cells after the block point of T cell receptor rearrangement. This suggests a role in very early T cell development, likely expressed by pro-T or pre-T cells, thymic stromal cells, and possibly macrophages, epithelial, and dendritic cells. This comports with the observation that tissue distribution studies have not detected significant expression in other organs or tissues. See also, Table 7.

TABLE 7 mTECK mRNA expression in tissues and cells

| cDNA libraries cell type or tissue | neg | pos | northern blot cell type or tissue | neg |
|---|---|---|---|---|
| Th2 CD4+ T cells | X | | heart | X |
| Th1 CD4+ T cells | X | | brain | X |
| Lung | X | | spleen | X |
| L cells | X | | lung | X |
| RAG-1 KO lung | X | | liver | X |
| RAG-1 KO heart | X | | skeletal muscle | X |
| RAG-1 KO brain | | X (+) | kidney | X |
| RAG-1 KO spleen | X | | testis | X |
| RAG-1 KO kidney | X | | thymus | |
| RAG-1 KO testis | | X (+) | small intestine | |
| RAG-1 KO thymus | | X (+++) | CD4+8– thymocytes R/A | X |
| RAG-1 KO liver | | X (+) | CD4–8+ thymocytes R/A | X |
| CD4–8– thymocytes | X | | CD4–8– thymocytes R/A | X |
| A20-J B-cell lymphoma | X | | B220+ splenocytes R/A | X |
| BW CD4–8–3– hybridoma | X | | Thy-1+ splenocytes R/A | X |
| pro-T cells | | X (+) | 1G18LA macrophages R/A | X |
| pre-T cells | X | | primary thymic stroma R/A | X |
| 30-R bone marrow stroma | X | | 3D.1 thymic epithelial R/A | X |
| D10 T-cell hybridoma | X | | MTSC-C thymic epithelial | X |
| CTLL T-cell clone | X | | 30.R bone marrow stroma | X |
| peritoneal macrophages | X | | | |
| splenic dendritic cells | X | | | |

Analysis of mTECK mRNA was carried out as described.
+ to +++ indicates the relative intensity of the signal.
R/A: resting or activated.

Species analysis indicated positive signals by hybridization in human, rat, and hamster DNA. Tissue distribution analysis suggests that the gene is expressed in human small intestine, which also is a tissue which supports T cell differentiation.

The combination of the structure and distribution of this chemokine suggests a role in T cell development, which normally occurs in the thymus.

B. MIP-3α

The MIP-3α was identified from a cDNA library made from human monocytes activated with LPS and IFN-γ, in the presence of anti-IL-10. See, Rossi, et al. (1997) *J. Immunology* 158:1033-1036, which was published after priority dates of this filing. Message of the chemokine has also been detected in pancreatic islet cells, fetal lung, and hepatic HEPG2 cells, suggesting a physiological role in inflammation or medical conditions in such organs/tissues.

The gene is expressed in HL-60 (promyelocytic leukemia); S3 (HeLa cell); K562 (chronic myelogenous leukemia); MOLT-4 (lymphblastic leukemia); Raji (Burkitt's lymphoma); SW480 (colorectal adenocarcinoma); A549 (lung carcinoma); and G361 (melanoma) cell lines, as determined by probing on a tissue blot from CLONTECH. Tissue expression gave a positive signal in lymph node, appendix, peripheral blood lymphocytes, fetal liver, and fetal lung, suggesting a physiological role in inflammation or medical conditions in such organs/tissues; but no detectable signal in spleen, bone marrow, brain, and kidney.

The main transcript appears to be about 1.2 kb, with two additional transcript sizes in fetal lung RNA. Among the various tissues, transcript sizes of 1.8, 2.7, and 4.2 kb were detected.

Positive signals were also detected in the following cDNA libraries: dendritic cells activated with LPS, but not when activated with GM-CSF and IL-4; monocytes treated with LPS, IFN-γ, and anti-IL-10, but not when treated with LPS, IFN-γ, and IL-10; and activated PBMC.

These expression data implicate this chemokine in inflammatory responses upon cell activation. The lymph nodes, appendix, and PBL are sites where inflammatory processes take place. The MIP-3α may exert its effects on monocytes and cells involved in inflammatory events. Other structural features implicate this chemokine in eosinophil and lung physiology, e.g., asthma indications. Thus, an antagonist of the chemokine, e.g., an antibody, may be important for treatment of asthmatic conditions. Also, IL-10 appears to inhibit MIP-3α expression.

The human MIP-3α is a ligand for the DC CR. Thus, a positive control exists for the the Ca++ flux assay for that receptor. This allows for the further screening of agonist ligands for the DC CR. Moreover, the DC CR was isolated from eosinophil cDNA, and observations have been made that eosinophils migrate to MIP-3α in vitro. These suggest that the MIP-3α interaction with the DC CR is important in recruitment of eosinophils, as occurs with the eotaxin ligand and the CCR3. As such, antagonists of the MIP-3α interaction with the DC CR will likely be useful in inhibiting eosinophilia, particularly in the lung, or lung inflammation. These may accompany asthmatic or other pulmonary conditions.

Antagonists to MIP-3α may be made either with antibodies, or other binding compositions which inhibit receptor interaction. The antibodies may be to the ligand, MIP-3α itself, or to the binding portions of the receptor, DC CR. Muteins of the chemokine may block receptor interaction, and with a positive control, chemokine muteins may be screened for variations which compete with the wild type chemokine at various concentrations. See, e.g., Kenakin (1987) *Pharmacological Analysis of Drug-Receptor Interaction* Raven Press, N.Y.; Arunlakshana and Schild (1959) *Br. J. Pharmacol.* 14:48-58; Black (1989) *Science* 245:486-493; Zurawski, et al. (1986) *J. Immunol.* 137:3354-3360; Zurawski and Zurawski (1988) *EMBO J.* 7:1061-1069; Zurawski and Zurawski (1992) *EMBO J.* 11:3905-3910; Imler and Zurawski (1992) *J. Biol. Chem.* 267:13185-13190.

C. MIP-3β

The MIP-3β was identified in a cDNA library made from human monocytes activated with LPS and IFN-γ, in the presence of anti-IL-10. Its distribution in other cells and tissues has not been fully determined.

D. Dendritic Cell Receptor for Chemokine; DC CR

The DC CR was isolated from a cDNA library made from a dendritic cell cDNA library. It appears to be expressed in certain T cells, spleen cell subsets, NK cells, and other cell populations enriched in dendritic cells, including CD1a+, CD14+, and CD1Aa+ cells. It did not give a detectable signal in TF1, Jurkat, MRC5, JY, or U937 cells.

Being found on dendritic cells, its ligand, including the MIP-3α, may be important in attracting appropriate cells for the initiation of an immune response. MIP-3α has been shown to be a very potent chemoattractant for dendritic cells. Significant roles of the ligand and receptor in pulmonary physiology are suggested, both from the distribution of the receptor and ligand. The receptor may be also present in other cells important in such responses.

E. Monocyte/Dendritic Cell Receptor for Chemokine; M/DC CR

The M/DC CR was isolated from a cDNA library made from primary monocyte cells activated with LPS and IFN-γ but subtracted with known high abundance genes from those cells. The abundance of this gene is probably less than about 1% of message from those cells.

Tissue expression gave a positive signal in spleen, PBL, lung, placenta, and small intestine; but no detectable signal in brain, liver, kidney, and muscle. This distribution suggests a hematopoietic role.

There appears to be one main transcript, but the existence of additional or alternatively spliced messages has not been eliminated.

Positive signals were also detected in the following cDNA libraries: monocytes and dendritic cells; but signals were not detectable in CD8+ T cells, or in either resting or activated splenocytes, gamma-delta T cells, NK cells, or B cells. Immunohistochemistry will be performed to confirm absence in the T cell and B cell compartments and to check in tonsil, particularly in view of location in spleen and placenta. The relatively restricted distribution on monocytes and dendritic cells leads both to its designation, and suggests a functional role in those cell types, which are important in the initiation of immune responses through their ability to process and present antigen to T cells.

VI. Specific Characterization of TECK

A novel CC chemokine was identified in the thymus of mouse and human and was designated TECK as Thymus Expressed ChemoKine. TECK has weak homology with other CC chemokines and maps to mouse chromosome 8. Besides the thymus, mRNA encoding TECK was detected at substantial levels in the small intestine and at low levels in the liver. The source of TECK in the thymus was determined to be thymic dendritic cells, while in contrast bone marrow-derived dendritic cells do not express TECK. The murine TECK recombinant protein showed chemotactic activity for activated macrophages, dendritic cells and thymocytes. We conclude that TECK represents a novel thymic dendritic cell-specific CC chemokine which is possibly involved in T-cell development.

Chemokines belong to a family of small peptides (6-15 kDa) whose best described biological function is to control the migration of certain leukocyte populations to localized sites of inflammation. Baggiolini, et al. (1994) *Adv. in Immun.* 55:97-179; Schall and Bacon (1994) *Curr Opin Immun* 6:865-873; Hedrick and Zlotnik (1996) *Curr. Opin. Immunol.* 8:343-347. In the last few years many new members of the chemokine super family have seen the characterized. Initially, new chemokines were identified through their chemotactic effects on leukocytes (Baggiolini et al. (1994); Schall and Bacon (1994)) and were isolated mainly from blood leukocytes or cell lines. More recently, approaches based on the selective cloning of secreted molecules by signal sequence trap (Tashiro, et al. (1993) *Science* 261:600-603; Imai, et al. (1996) *J. Biol. Chem.* 271:21514-21521) or on the exploitation of public and private databases of expressed sequence tags (EST) through bioinformatics (Hieshima, et al. (1997) *J. Biol. Chem.* 272:5846-5853; Patel, et al. (1997) *J. Exp. Med.* 185:1163-1172; and Rossi, et al. (1997) *J. Immunol.* 158:1033-1036), have allowed the rapid identification of novel chemokines based on sequence and structural homologies. These approaches take advantage of the fact that most of the chemokines are secreted factors whose protein sequence contain four conserved cysteines (Schall (1994) "The Chemokines" pp. 419-460 in Thomson (eds.) *The Cytokine Handbook*, Academic Press, New York. The CXC or α chemokine family has the two first amino-terminal cysteines separated by a non-conserved amino acid. In the CC or β chemokine family, these two cysteines are consecutive. A third type of chemokine, the C or γ family, is represented by lymphotactin, which conserves two cysteines (1 and 3) instead of the original four (Kelner, et al. (1994) *Science* 266:1395-1399). Finally, a recently identified chemokine with three amino acids separating the first two cysteines defines a fourth $CX_3C$ family (Bazan, et al. (1997) *Nature* 385:640-644).

Interestingly, some of the new chemokines discovered show a relatively restricted pattern of expression (Imai et al. (1996); Hieshima et al. (1997)). It is tempting to suggest that these new approaches may lead to the discovery of tissue- or cell-specific chemokines. In addition, new biological evidence for important new roles of chemokines in hemopoiesis (Cook (1996) *J. Leukoc. Biol.* 59:61-66; and Nagasawa, et al. (1996) *Nature* 382:635-638) and the control of viral infections including HIV (Cocchi, et al. (1995) *Science* 270:1811-1815; and Cook, et al. (1995) *Science* 269:1583-1585). Thus, the molecular cloning of novel chemokines through DNA-based strategies may uncover novel proteins belonging to the chemokine super family but whose physiological role goes beyond the control of inflammation.

In an attempt to identify novel genes involved in T-cell development, we analyzed a cDNA library from the thymus of Recombinase Activation Gene-1 (RAG-1) deficient mice. We identified a novel CC chemokine designated TECK for Thymus Expressed ChemoKine, based on sequence homology with other known chemokines. We subsequently isolated the human homologue of TECK. The pattern of expression of TECK mRNA is highly restricted to the thymus and small intestine in both human and mouse. Moreover, in the mouse thymus, TECK protein is produced by dendritic cells while splenic dendritic cells do not express TECK mRNA. Recombinant TECK showed chemotactic activity on thymocytes, macrophages, THP-1 cells and dendritic cells, while it was inactive on peripheral lymphocytes and neutrophils. The restricted pattern of expression of TECK together with its biological properties suggest a role for this novel dendritic cell-specific chemokine in T-cell development.

A. Cloning and Structural Analysis of Mouse TECK

A directional cDNA library was made from RAG-1 deficient mouse thymus and analyzed by random sequencing. One of the clones contained an open reading frame with significant homology to previously described CC chemokines. The full-length cDNA contains 1037 bp including an open reading frame of 426 bp encoding a protein of 142 amino acids and will be identified in this report as mTECK (see Table 1). In the 3' untranslated region, there is one unique polyadenylation signal consistent with the single mRNA species observed in northern blots. The mTECK cDNA does not contain any ATTTA transcript destabilization motif (Shaw and Kamrn (1986) *Cell* 46:659-667). The comparison of the amino acid sequence of mTECK with previously described murine CC chemokines demonstrates the conservation of the four cysteines present in all these chemokines. However, mTECK shows few additional identities with these proteins.

B. Cloning and Molecular Characterization of Human TECK

To investigate the possible existence of a gene homologous to mTECK in other mammalian species, a Southern blot with genomic DNA from various species was hybridized with the mTECK cDNA probe. Under high stringency conditions, hybridizing bands were detected in mouse, rat, hamster and human genomic DNAs. Interestingly, a single band was detected in human, suggesting that a single gene encodes for TECK in this species. The multiple bands present in mouse, rat and hamster could be the result of a internal EcoRI site within the TECK gene. Alternatively, the TECK gene may have been duplicated in these species.

In order to clone the human homologue of mTECK, a blot of cDNAs from a panel of human cDNA libraries was hybridized with the mTECK cDNA probe. A signal was observed in a fetal small intestine cDNA library. Screening of this library with the mTECK probe allowed the isolation of several identical clones of 1012 bp with an open reading frame of 453 bp encoding a protein of 151 amino acids. This protein had a much higher degree of homology at the nucleic acid level (71% nucleic acid identity for the open reading frame and 49.3% amino acid identity) to mTECK than to other known CC chemokines and was thus designated as hTECK.

C. DNA Sequencing and Bioinformatics

The nucleotide sequence of CRAM was determined using an ABI 377 automated sequencer and standard techniques. DNA sequence analyses were performed using Sequencer 3.0 (Gene Codes Corporation, Ann Arbor, Mich.) and MacVector 6.0 (Oxford Molecular Group). Comparisons to GenBank databases were performed using the BLAST program on web-based servers. Sequence alignments and phylogenetic analyses utilized ClustalW 1.6 (Higgins, et al. (1996) *Methods in Enzymology* 266:383) and TreeViewPPC 1.2 (Page (1996) *Computer Applications in the Biosciences* 12:357).

D. Analysis of CRAM mRNA Expression

Multiple-tissue Northern blots were purchased from Clontech (Palo Alto, Calif.). Poly(A)+ RNA from human monocytes was used for RNA blot analysis. cDNA libraries from human cells (5 μg) in the pSPORT vector (Life Technologies) were digested with SalI and NotI to release cDNA inserts, electrophoresed on 1% agarose gels, and subjected to Southern blot transfer/hybridization. Hybridizations with $^{32}P$-labeled CRAM DNA fragments encoding the C-terminal 144 amino acids of the predicted ORF were done at 65° C. in ExpressHyb (Clontech, Palo Alto, Calif.) for 2 hr, followed by two stringent washes at 50° C. in 0.1×SSC, 0.1% SDS for 45 min. Hybridization was detected using a STORM 860 phosphorimager (Molecular Dynamics, Sunnyvale, Calif.). Reverse transcriptase PCR (RT-PCR) was performed with Superscript II reverse transcriptase (Life Technologies) and Taq DNA polymerase (Boehringer-Mannheim, Indianapolis, Ind.). PCR was for 35 cycles of 95° C./45 sec, 62° C./30 sec, 72° C./60 sec. Primers specific for exon 1 (5'-AGACGCTTCAGAGATCCTCTGGAG-GCC; SEQ ID NO: 22) or exon 2 (5'-GAAGCTGCT-TCGGGGGGTGAGCAAAC; SEQ ID NO: 23) were used in conjunction with an exon 3-specific primer (5'-CAAA-CACAGCAGAGCAGAGTGATGGCACC; SEQ ID NO: 24) for amplification.

E. Chromosomal Localization

PCR was performed on genomic DNA from the 83 cell lines of the Stanford Human Genome Center G3 radiation hybrid panel (Research Genetics, Huntsville, Ala.) using CRAM primers: (5'-GTGTCCTGGCATGGGTAACAGCC; SEQ ID NO: 25) and (5'-CGGTGGAATGGTCAGGTTCT-TCCC; SEQ ID NO: 26) as previously described for the GeneBridge 4 radiation hybrid panel (Samson, et al. (1996) *Genomics* 36:522). Data correlating the presence or absence of PCR product to each cell line were entered into the RHserver (Stanford Human Genome Center). Co-localized STSs were identified on the human physical map using the Entrez server (National Center for Biotechnology Information).

F. Chemotactic Activities of mTECK Protein

To evaluate the biologic properties of mTECK, a recombinant protein with a N-terminal FLAG peptide was obtained in a bacterial expression system. In some experiments, a recombinant mTECK protein with a C-terminal FLAG was used and similar results were obtained. Interestingly, mTECK induced the migration of mouse thymocytes (FIG. 1A). The optimal response was obtained with a dose of 10 ng/ml TECK. Cell migration was determined to be chemotaxis and not chemokinesis through the checkerboard analysis. Furthermore, it is established that chemokines bind to specific receptors that are coupled through heterotrimeric G proteins to intra-cellular signal-transducing pathways. Murphy (1994) *Annu. Rev. Immunol.* 12:593-633. To determine whether the chemotaxis of thymocytes involved a G protein-coupled receptor, cells were incubated prior to the assay with 10 ng/ml pertussis toxin which ADP-ribosylates $G_{\alpha i}$-proteins. Katz, et al. (1992) *Nature* 360:686-689. This pre-treatment completely abrogated the chemotactic response of thymocytes to mTECK (FIG. 1A).

Figure 1B:
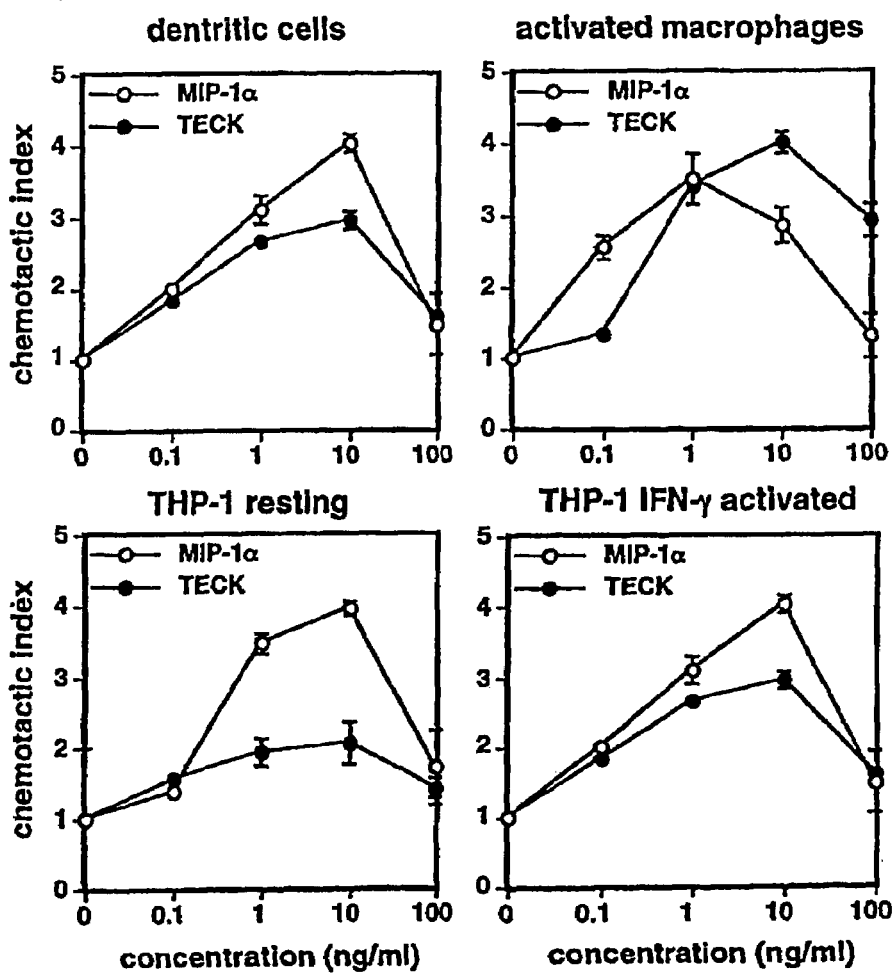

The recombinant mTECK protein also induced the migration of human monocytic THP-1 cells activated for 16 hours with IFN-γ (FIG. 1B), while it was not significantly active on resting THP-1 cells. This experiment showed that mTECK is active on human cells. In addition, mTECK induced activated mouse peritoneal macrophages to migrate as well as highly purified mouse splenic dendritic cells (FIG. 1B). In all these experiments, the optimal dose of mTECK was 10 ng/ml. In contrast, no chemotaxis was observed with bone marrow cells, purified neutrophils, splenic B cells, splenic T cells or IL-2 activated RAG-1 deficient mouse splenocytes lacking mature T and B lymphocytes (Mombaerts, et al. (1992) *Cell* 68:869-877) and therefore enriched in NK cells. These data are consistent with the absence of in vivo accumulation of neutrophils, monocytes or lymphocytes 2 and 5 h following an intra-peritoneal injection of 10 µg mTECK. Collectively, these data indicate that TECK is a chemotactic factor for thymocytes, macrophages and dendritic cells.

G. TECK, a Distant Member of the CC Chemokine Family

In this report, we describe the molecular isolation and characterization of TECK, a novel mouse and human CC chemokine. Analysis of its predicted amino acid sequence showed that TECK is distantly related to previously described CC chemokines. Conservation of particular amino acids among most CC chemokines may be related to their functional importance. Beall, et al. (1992) *J. Biol. Chem.* 267:3455-3459; and Lusti-Narasimhan, et al. (1995) *J. Biol. Chem.* 270:2716-2721. In particular, a tyrosine residue between the second and third cysteines has been shown to be critical for monocyte chemotaxis (in position 50) (Beall et al. (1992)). While TECK does not have a tyrosine at this particular position, it has one in position 52 that may have the same function, since TECK is chemotactic for activated monocytes. In addition to these differences in the primary structure, the gene encoding TECK maps on chromosome 8 in the mouse, unlike most other CC chemokines which are clustered on chromosome 11. This is not the first report of an unusual chromosomal location for a CC chemokine. We have cloned the human CC chemokine MIP-3β and showed that its gene was on chromosome 9 rather than 17 (Rossi, et al. (1997)), and the gene encoding the novel human CC chemokine MIP-3α/LARC (Rossi, et al. (1997)) has been mapped on chromosome 2 (Hieshima, et al. (1997)). It is likely that the CC chemokines on chromosome 11 in the mouse and 17 in human have been generated through gene duplication of a primordial chemokine. Our results suggest that TECK may have been generated at an earlier stage during evolution. In this regard, the TECK gene may have evolved to ensure functions similar to other CC chemokines with a distant primary structure but through similar receptor(s) as dictated by its secondary and tertiary structures. Alternatively, the receptor(s) and physiological role of TECK may be unique among chemokines.

H. TECK Expression and Function is Associated With T-Cell Development

We observed that TECK was strongly expressed in the thymus which is the primary lymphoid organ where T-cell development takes place. Recently, another CC chemokine highly expressed in the thymus, TARC, has been identified. Imai, et al. (1996). However, TARC is also expressed in lung and colon as well as activated PBMC (Imai, et al. (1996)) while TECK was absent from these tissues. Besides the thymus, numerous reports indicate that T cell development can occur in the small intestine (Poussier and Julius (1994) *Annu. Rev. Immunol.* 12:521-553) where TECK is also expressed. Interestingly, the liver has also been suggested to support T-cell development to some extent (Abo, et al. (1994) *Int. Rev. Immunol.* 11:61-102) and we observed a low TECK expression in a liver cDNA library. These data show that TECK expression correlates with organs that support T-cell development.

While many molecular and cellular aspects of T-cell differentiation are well documented, the precise role of chemokines in T-cell development is still unknown. Recently, it has been shown that the bone marrow stroma-derived CXC chemokine SDF-1 is important for B lymphopoiesis and myelopoiesis since SDF-1 −/− mice are impaired for these functions (Nagasawa, et al. (1996)). Similarly, it is likely that chemokines act at different steps of T-cell differentiation. Chemokines, together with the expression of appropriate adhesion molecules, may dictate the migration of uncommitted progenitors from the bone marrow to other anatomic locations. Indeed SDF-1 is chemoattractant for human CD34+ progenitor cells. Aiuti, et al. (1997) *J. Exp. Med.* 185:111-120. The observation that TECK is chemoattractant for thymocytes but not for mature peripheral T cells suggests that TECK could attract T-cell progenitors to the thymus. Such populations are very difficult to isolate in sufficient numbers to conduct in vitro chemotaxis experiments, but we are currently designing new strategies to address this important question. In addition, we have not found significant chemotactic activity of TECK on bone marrow cells. SDF-1 was shown to be much less potent on CD34+ progenitors from the peripheral blood than those from the bone marrow. Aiuti, et al. (1997). It is possible that the sensitivity of progenitor cells to TECK would increase as these cells leave the bone marrow to colonize lymphoid organs. Importantly, intra-thymic maturation is also characterized by a directional migration from the subcapsular region which contains the earliest progenitors to the cortex and finally to the medulla where thymocytes finish their maturation (Boyd, et al. (1993)). It is possible that the secretion of TECK by medullary dendritic cells may play a role in this directional migration. Yet another possibility is that TECK may play a role in the organization and development of the thymic stroma.

We also showed that TECK is chemotactic for activated macrophages and dendritic cells. These two cell types also play important roles in T-cell development. Through a complex screening process involving positive and negative selection events most of the antigenic specificities randomly generated in the thymus will be eliminated by programmed cell death (Janeway (1994) *Immunity* 1:3-6). The efficient scavenging of dead thymocytes is probably mediated, at least partially, by thymic macrophages and thus TECK could play an important role through its action on activated macrophages. Further along, T-cells with a high affinity for self-antigens and thus potentially harmful are eliminated through negative selection (Janeway (1994)). It is believed that thymic dendritic cells are primarily responsible for the negative selection of thymocytes, therefore playing a major role in the establishment of tolerance. Inaba, et al. (1991) *J. Exp. Med.* 173:549-559. An efficient mechanism of central tolerance should eliminate T cells potentially reactive against auto-antigens which are not expressed in the thymus, such as organ specific auto-antigens. Several known chemokines induce the migration of dendritic cells and could therefore contribute to their recruitment during peripheral immune responses. Sozzani, et al. (1995) *J. Immunol.* 155:3292-3295; and Xu, et al. (1996) *J. Leukoc. Biol.* 60:365-371. Similarly, dendritic cells presenting organ-specific or other antigens could be recruited to the thymus or the small intestine and induce negative selection of T cells specific for these antigens. It is possible that thymus- and small intestine-specific chemokines active on dendritic cells such as TECK could play an important role in the establishment of tolerance. Thus, TECK could potentially interact at several important steps of T-cell development. Future experiments will aim to define the precise role of TECK in T-cell development and other physiological processes through the use of genetically modified mice.

I. TECK is Specifically Expressed by Thymic Dendritic Cells

Dendritic cells represent an heterogeneous cell population derived from bone marrow progenitors. They are present in non-lymphoid organs as immature dendritic cells (such as Langerhans cells in the skin) where they display a high ability for antigen capture. Cella, et al. (1997) *Curr. Opin. Immunol.* 9:10-16. Subsequent to antigen challenge, they will migrate to secondary lymphoid organs and will acquire a high capacity to present processed antigens to naive T-cells to initiate a specific immune response (Cella, et al. (1997)). It has been shown that dendritic cells can derive from CD34+ progenitors cultured in the presence of GM-CSF and TNF-α (Caux, et al. (1992) *Nature* 360:258-261; and Caux, et al. (1996) *J. Exp. Med.* 184:695-706) or from monocytes in the presence of GM-CSF and IL-4 (Sallusto and Lanzavecchia (1994) *J. Exp. Med.* 179:1109-1118). Interestingly, there is also evidence for a lymphoid dendritic cell precursor in thymus and bone marrow which is able to derive both lymphocytes and dendritic cells in the absence of GM-CSF. Ardavin, et al. (1993) *Nature* 362:761-763; Galy, et al. (1995) *Immunity* 3:459-473; Marquez, et al. (1995) *J. Exp. Med.* 181:475-483; and Wu, et al. (1996). These lymphoid-derived dendritic cells may have different functional properties such as a negative regulation of T-cell responses since they express FasL in the mouse. Suss and Shortman (1996) *J. Exp. Med.* 183:1789-1796. We found that TECK was expressed at high levels in mouse thymic dendritic cells but was absent in cDNA libraries from mouse splenic dendritic cells or from human dendritic cells generated in vitro from CD34+ precursors or monocytes. Interestingly, mTECK mRNA was present at a low level in a population of early thymocyte progenitors still able to derive dendritic cells (Wu, et al. (1996). Thus, it would be tempting to suggest that TECK could be a specific marker of lymphoid-derived dendritic cells. However, we observed that TECK was absent from splenic dendritic cells that likely contain lymphoid-derived dendritic cells. The expression of TECK mRNA appeared in the spleen of mice injected with LPS would suggest that peripheral dendritic cells may express TECK upon activation, but we found that TECK was not expressed in cDNA libraries of bone-marrow derived dendritic cells activated with LPS, PMA and ionomycin or IL-1α and TNF-α. It is possible that the normal expression of TECK is specific for lymphoid-derived dendritic cells or, alternatively, that it is upregulated by very specific stimuli present in the thymic and intestinal micro-environment under physiological conditions. Consistent with the latter hypothesis is our observation of specific staining of thymic endothelial cells with anti-TECK antibody since we have not been able to find TECK expression in human HUVEC endothelial cells by northern blot analysis, without activation or following a 16 hour-activation with various combinations of IL-1, TNF-α, IL-4, IL-7 and oncostatin while some of these stimuli induce the expression of other CC chemokines in endothelial cells. Rollins and Pober (1991) *Am. J. Pathol.* 138:1315-1319; Marfaing-Koka, et al. (1995) *J. Immunol.* 154:1870-1878; Garcia-Zepeda, et al. (1996) *J. Immunol.* 157:5613-5626; and Garcia-Zepeda, et al. (1996) *Nat. Med.* 4:449-456. Taken together, our data strongly suggest that TECK is a novel chemokine specifically expressed by activated lymphoid-derived dendritic cells.

Through their function of antigen presentation, dendritic cells play major roles in the establishment of tolerance and in the initiation of an antigen-specific immune response. The use of purified dendritic cells has been recently proposed in different therapeutic protocols (Cella, et al. (1997)). The discovery of factors with a regulated expression in dendritic cells such as the novel CC chemokine TECK will certainly improve our knowledge of the biology of dendritic cells and lead to the design of relevant in vivo applications.

J. Mice and In Vivo Experimental Procedures

Four to eight week-old and time-pregnant BALB/c mice were purchased from Simonsen Laboratories (Gilroy, Calif.). RAG-1-deficient mice (Mombaerts, et al. (1992)) were purchased from The Jackson Laboratory (Bar Harbor, Me.). To analyze TECK expression after in vivo activation, various organs were recovered from pools of 2 mice 3 hours after intravenous LPS injection (50 μg LPS in 200 μl PBS or 200 μl PBS for controls).

K. Cell Purification, Culture and Stimulation.

THP-1 cells (TIB-202 from the American Type Culture Collection, Rockville, Md.) were cultured in complete medium which consisted in RPMI 1640 medium (JRH BioSciences, Lenexa, Kans.) supplemented with 10% FCS, 200 mM L-glutamin, $5 \times 10^{-5}$ M mercaptoethanol, MEM amino-acids and vitamins, sodium bicarbonate, penicillin, streptomycin (all from Sigma, ST. Louis, Mo.), and gentamycin (Boehringer, Indianapolis, Ind.). To obtain activated mouse macrophages, 10 ml of cold PBS were injected into the peritoneum and the collected cells allowed to adhere to plastic for 24 h in complete medium. The adherent fraction, mostly macrophages, was then collected. To obtain splenic dendritic cells, a splenocyte cell suspension was prepared in RPMI 1640 Dutch modified medium (Life Technologies, Paisley, Scotland) as described previously in, e.g., Macatonia, et al. (1987) *J. Exp. Med.* 166:1654-1667. Splenocytes were incubated at 37° C. for 16 h and the cell suspension was collected and laid over Metrizamide (Nycomed Pharma, Oslo, Norway). After centrifugation for 10 min. at 1700× g, the low interface was collected and stained with anti-Mac-1 (Pharmingen, San Diego, Calif.) and the anti-CD11c N-418 antibodies (Macatonia, et al. (1993) *J. Immunol.* 150:3755-3765). Splenic dendritic cells were sorted by flow cytometry on a FACStar plus cell sorter (Becton Dickinson, Mountain View, Calif.) to a purity greater than 98% upon reanalysis in all the experiments included in this report. To obtain thymic dendritic cells, thymuses were cut in small fragments and resuspended in 10 ml of RPMI-1640 +10% FCS containing 1 mg/ml collagenase and 0.02 mg/ml DNase I (both from SIGMA) and digested with continuous agitation at room temperature for 30 min. (Shortman, et al. (1995) *Adv. Exp. Med. Biol.* 378:21-29). One ml of 0.1M EDTA pH 7.2 was added for an additional 5 min. Cells were then washed in complete medium, resuspended in complete medium and overlaid onto Metrizamide. The thymic dendritic cell-enriched preparation was then stained with anti-IAd and N-418 antibodies and the dendritic cells sorted by flow cytometry L. Molecular Cloning of Mouse and Human TECK The cDNA encoding mouse TECK was obtained by random sequencing of a RAG-1 KO mouse thymic directional cDNA library. Briefly, mRNA was extracted using RNAzol™ B (Tel-Test, Friendswood, Tex.) and then oligotex-dT mRNA kit (Quiagen, Chatsworth, Calif.) following the manufacturer's instruction. A directional cDNA library was prepared using the Superscript™ Plasmid System (Gibco-BRL, Grand Island, N.Y.) and cloned into the pME18s plasmid vector. Sequencing was done using the TaQ DyeDeoxy Terminator Cycle Sequencing kit (Applied Biosystems, Foster City, Calif.). To determine whether TECK was present in other mammals including human, a Southern blot containing EcoRI digested genomic DNA from different species (Bios Laboratories, New Haven, Conn.) was hybridized with the full-length mouse TECK cDNA.

The cDNA encoding human TECK was found by screening of a small intestine cDNA library using the full-length mouse TECK cDNA as a probe following standard procedures.

M. Northern Blot Analysis of RNA and Southern Blot Analysis of cDNA Libraries

All RNA's were isolated from tissues or cells using RNAzol™ B (Tel-Test) and analyzed after electrophoresis in a 1% formaldehyde-agarose gel (10 μg/lane). RNA's were then blotted onto a Hybond-N+ nylon membrane (Amersham, Arlington Heights, Ill.). Some northern blots of mRNA were bought from Clontech (Palo Alto, Calif.). To analyze the expression of TECK in cDNA libraries (obtained from T. MacClanahan, DNAX), 10 μg of DNA were digested with the appropriate restriction enzymes to release their inserts and analyze by Southern blotting onto nylon membranes. Northern blots and blots of cDNA libraries were hybridized for 16 hours at 65° C. with a $^{32}$P-labeled probe consisting in the full-length cDNA encoding for mouse or human TECK and then washed and exposed, according to standard protocols.

N. Inter Specific Mouse Backcross Mapping

Inter specific backcross progeny were generated by mating (C57Bl/6J×M. spretus) F1 females and C57Bl/6J males as described, e.g., in Copeland and Jenkins (1991) *Trends Genet.* 7:113-118. A total of 205 $N_2$ mice were used to map the Teck locus. DNA isolation, restriction enzyme digestion, agarose gel electrophoresis, Southern blot transfer and hybridization with the full-length mTECK cDNA probe were performed as described, e.g., in Jenkins, et al. (1982). Fragments of 7.5, 6.9, and 2.5 kb were detected in HincII digested C57Bl/6J DNA and fragments of 8.8 and 5.4 kb were detected in HincII digested M. spretus DNA. The presence or absence of the 8.8 and 5.4 kb HincII M. spretus-specific fragments, which cosegregated, was followed in backcross mice. A description of the probes and RFLPs for two of the loci linked to Teck including Insr has been reported previously, e.g., in Ceci, et al. (1990) *Genomics* 6:72-79. Recombination distances were calculated as described (Green (1981) "Linkage, recombination and mapping" pp. 77-113 in *Genetics and Probability in Animal Breeding Experiments*, Oxford University Press, New York) using the computer program SPRETUS MADNESS.

O. Measurement of TECK mRNA Expression by RT-PCR

RNA's from sorted thymic dendritic cells or fetal thymuses were prepared with the RNeasy total RNA kit (Quiagen, Chatsworth, Calif.), following the manufacturer's instructions. First strand cDNAs were generated by reverse transcription with a random hexamer in a 10 μl reaction and 1 μl of this reaction was used as a template for PCR. TECK expression was compared to the expression of hypoxanthine-guanine phosphoribosyl transferase (HPRT). Primer sequences were as follows: TECK: 5' primer, 5'CCTTCAG-GTATCTGGAGAGGAGATC3' (SEQ ID NO: 20; nucleotides 58-72 of SEQ ID NO: 1) and 3' primer, 5'CACGCT-TGTACTGTTGGGGTTC3' (SEQ ID NO: 21; complement of nucleotides 447-468 of SEQ ID NO: 1), HPRT: 5' primer, 5'GTAATGATCAGTCAACGGGGGAC3' (SEQ ID NO: 17) and 3' primer, 5'CCAGCAAGCTTGCAACCT-TAACCA3' (SEQ ID NO: 18). Samples were submitted to 25 cycles of amplification, each composed of 94° C. for 1 min., 57° C. for 30 s and 72° C. for 2 min. PCR products were then separated by electrophoresis in 2% agarose gels and stained with ethidium bromide.

P. In Situ Hybridization

Biotin-14-CTP labeled sense and antisense riboprobes were generated using a non radioactive RNA labeling system (Gibco, Gaithersburg, Md.) and the plasmid PCRII (InVitrogen, Carlsbad, Calif.) containing a 400 base pair TECK cDNA fragment inserted by PCR and TA cloning (InVitrogen). Paraffin-embedded tissues were cut in 3-5 μm sections, mounted on slides, baked at 60° C. for one hour, deparaffinized in xylene (Fisher Scientific, Pittsburgh, Pa.) and immersed in 100% ethanol. Sections were then incubated for 10 min at 37° C. in proteinase K solution (40 mg/ml) (Gibco) in PBS and rinsed for 2 min in PBS at room temperature before being refixed in 10% formalin (Fisher Scientific, Pittsburgh, Pa.) in PBS for 1 min. Next, the sections were dehydrated through graded solutions of ethanol and air dried. Hybridization was carried out using the Gibco in situ hybridization and detection system kit. Vanadyl ribonucleoside complex (Gibco) was added to the hybridization solution (39 mM final). A 0.1 μg/ml concentration of each probe was used during an 18 h hybridization at 42° C. Post-hybridization washes used room temperature 0.2×SSC. Following detection and substrate visualization, the slides were counterstained with 1% nuclear red stain (Sigma, St. Louis, Mo.).

Q. Immunohistochemistry

A polyclonal antibody specific of a synthetic decapeptide identical to the C-terminus part of murine TECK (FIG. 1) was prepared in rabbits by Research Genetics (Huntsville, Ala.). Normal rabbit serum from a pool of 50 different animals (Research Genetics) was used as a negative control. To study TECK protein expression in the mouse thymus, 6 μm thick cryostat sections were thaw mounted on organosilicone subbed slides (American Histology Reagent Co., Stockton, Calif.) and fixed in 3% formalin (Fisher Scientific, Springfield, N.J.) in Hank's Balanced Salt Solution with 0.01M HEPES (HBSS-HEPES), pH 7.4, for 15 min at room temperature. The sections were sequentially blocked for endogenous biotin binding using the Vector blocking kit (Vector Laboratories, Burlingame, Calif.) and for endogenous peroxidase activity with a 1% hydrogen peroxide, 0.2M sodium azide solution, in HBSS-HEPES with 0.1% saponin (staining buffer). Non-specific antibody binding sites were then blocked with 10% normal goat serum (Sigma) in staining buffer. Sections prepared as above were first incubated for 18 h at 25° C. with 1/500 dilution of polyclonal antibody or control rabbit serum in staining buffer. In the second step, the sections were incubated for 1 h at room temperature with biotin labeled goat anti-rabbit IgG (2 µg/ml) (Vector Laboratories) in staining buffer and then for 30 min at room temperature with the Vectastain Elite ABC Kit (Vector Laboratories) in staining buffer. The sections were then rinsed in HBSS-HEPES without saponin. Immunoenzyme tissue staining was revealed with 3,3'-diaminobenzidine tetrahydrochloride (DAB) substrate (0.5 mg/ml) (Sigma) in 0.05 M Tris, pH 7.4, containing 0.0075% hydrogen peroxide. The substrate reaction was stopped by rinsing the sections in distilled water. The sections were then counterstained with Harris' hematoxylin (Shandon Lipshaw, Pittsburg, Pa.).

The expression of TECK mRNA in murine adult thymus was analyzed by in situ hybridization and revealed a discrete positive non-lymphoid population within the thymus medulla. The expression of TECK protein was analyzed by using a polyclonal anti-serum made in a rabbit immunised with a peptide that consisted in the last 12 amino-acid of the murine TECK protein sequence. This polyclonal antibody reacts with the murine TECK recombinant protein prepared at DNAX both in ELISA and western blot. The application of this anti-serum on mouse adult thymic sections confirmed the distribution pattern obtained by in situ hybridization: the cells producing TECK are medullary stromal cells. The precise cell type producing TECK within the mouse thymus was identified, using the same anti-serum on sorted thymic subsets, as being the thymic dendritic cells.

R. Production of Recombinant Mouse TECK in *Escherichia coli* and Other Chemokines Mouse recombinant TECK was produced in *E. coli* as a N-terminal FLAG (DYKDDDDKL; SEQ ID NO: 19) fusion protein. Briefly, the fusion construct containing FLAG followed by the mTECK sequence minus the leader peptide (see Table 1) was obtained by PCR amplification of the TECK cDNA in order to flank the coding sequence with HindIII and EcoRI sites and subsequent ligation in the pFLAG.1 vector which contains the FLAG sequence and an OmpA signal sequence. Electro-competent UT 4400 *E. coli* were transformed with the pFLAG.1-mTECK plasmid. The cells were grown in 2×LB plus 50 µg/ml Ampicillin, induced at an OD. of 2.3 with 400 µM IPTG and harvested. The cell pellet was resuspended in cold lysis buffer (20 mM Tris pH 8, 2 mM EDTA, 20% sucrose, 0.1 mg/ml lysozyme, 100 µl Benzonase), homogenized and allowed to sit for 30 min. Then the same amount of a 1:4 dilution of cold lysis buffer without lysozyme was added for 10 more min. The solution was spun and the supernatant was filtered through a 0.2 µm membrane and then diluted 1:1 in 50 mM Tris pH 7.5. The diluted osmotic extract was submitted to chromatography on a Q-sepharose column equilibrated with 50 mM Tris pH 7.5 and eluted with a linear salt gradient. The fractions containing the recombinant protein were pooled. The fractions were then loaded onto a S-sepharose column equilibrated with 20 mM acetate pH 4.0. The column was eluted with a linear salt gradient and then with a 1.5 M NaCl wash that contained the protein. Finally, the eluate was loaded onto a reverse phase column. The column was eluted with a linear gradient of 20% to 80% acetonitrile+0.1% TFA. The concentration of the mTECK protein was estimated by Comassie blue staining and densitometric scanning of a 10% Nu-PAGE gel with lysozyme as a standard. The purity was estimated at 100% by sequencing of the N-terminus of the recombinant protein. Recombinant murine MIP-1α (R&D Systems, Minneapolis, Minn.) and lymphotactin (Hedrick, et al. (1997) *J. Immunol.* 158:1533-1540) were used as controls.

S. Assay for Chemotaxis

The in vitro migration of cells isolated as described above in response to TECK or other factors was assessed in a modified Boyden micro chamber (Neuroprobe, Cabin John, Md.) as described previously (Kelner, et al. (1994)). Briefly, factor dilutions in DMEM medium (Gibco) were loaded in the lower compartment in duplicate and $10^5$ cells in a 50 µl volume of DMEM were loaded in the upper compartment. The two compartments were separated by a 5-µm or 8-µm pore size polycarbonate filter (Nucleopore, Pleasanton, Calif.). After incubation at 37° C. for 80 min (or 120 min for lymphocytes), the filters were fixed in methanol and stained with Fields A and B. Cell migrated on the other side of the membrane were counted per five high-power fields (100×) under microscope. The chemotactic index was calculated from the number of cells counted with the test sample divided by the number of cells counted with medium alone.

Northern blot analysis was performed of RNA from different organs hybridized with the mTECK cDNA probe with or without in vivo LPS stimulation. Hybridizing bands corresponded to the predicted ≈1040 bp size for mTECK mRNA. Significant induction occurred in spleen (with virtually no background), and in thymus and small intestine (both with higher background); no signal was detected in either condition for heart, lung, kidney, or liver.

mTECK mRNA expression was analysed in the mouse fetal thymus. RNA's from fetal thymic lobes were extracted at day 14, 15, 16 and 17 of gestation. Positive RT-PCR signals were detected in each of day 14, 125, 16, and 17 samples.

mTECK mRNA expression in thymic dendritic cells was evaluated. A population enriched in thymic dendritic cells was prepared from 15 pooled adult thymuses. >99% pure dendritic cells were then sorted by flow cytometry based on their MHC Class II+ N-418+ phenotype. mTECK mRNA was then analyzed by RT-PCR and a MHC class II+ N-418− population sorted in the same experiment was used as a negative control. The N418+ sample gave a positive signal, while the N418− sample did not.

Expression analysis was performed with hTECK mRNA in different Human Tissues and Cell Types. Southern blots of human cDNA libraries digested with the appropriate restriction enzymes were hybridized with the hTECK cDNA probe. A major band hybridizing corresponding to the predicted length of hTECK mRNA (≈1040 bp) was observed with sometimes some other bands that may represent incomplete cDNAs. Positive signals were detected in tonsil, fetal spleen, and fetal small intestine. No signal was detected in activated (with PMA and ionomycin for 12 h) NK cells, activated (anti-CD40 antibody and IL-4 for 6 and 12 h) splenocytes, γδ T cells, activated (with anti-CD3 and PMA for 6, 12, and 24 h) PBMC, fetal testis, C+ (elutriated monocytes cultured with IFN-γ and IL-10) monocytes, C− monocytes, 70% pure dendritic cells (CD1α+ dendritic cell population obtained by expansion of CD34+ bone marrow cells with GM-CSF and TNF-α and resting), and DC3 (similar dendritic cell population stimulated with PMA and ionomycin for 1 and 6 h), DC5 (dendritic cells obtained by culturing peripheral blood monocytes in the presence of IL-4 and GM-CSF), U937 (premonocytic cell line), and CD1α cell lines. Ras KO mouse cDNA again confirmed that the mouse and human genes crosshybridize.

Four independent lines of transgenic mice expressing TECK in the brain have been made. All animals had neurologic disorders. In addition, several of them suffered severe infections. The consequences of TECK could be a direct one on brain cells which nature remains to be identify. Alternatively, since TECK has been shown in vitro to have effects on macrophages and dendritic cells which are critical effectors of immune responses, the overproduction of TECK could lead to distant effects on these cells at sites of infection. These results suggest that the blockade of TECK production in vivo may help to resolve particular pathological processes, in particular infections. The localization suggests a physiological role in immunological responses involving the thymus, or in colon/small intestine or gastrointestinal inflammation, e.g., Crohn's disease or inflammatory bowel disease.

VII. Specific Characterization of the M/DC CR (CRAM)

Abbreviations: BAC, bacterial artificial chromosome; bp, base pair; CKR, chemokine receptor; EST, expressed sequence tag; GPR, G-protein-linked receptor; PBMC, peripheral blood mononuclear cells; STS, sequence tagged site.

We describe a novel human gene with high homology to CC- or β-chemokine receptors (CKRs). This putative CKR, CRAM, is most similar to human CCR1, with 46% amino acid identity and 65% similarity. CRAM is encoded by at least two alternatively spliced 1.5 and 1.8 kb mRNAs which specify at least two proteins differing by 12 amino acids at the N-terminus (CRAM-A and CRAM-B). CRAM mRNA was detected mainly in lymphoid tissues and expressed in activated monocytes, but not in B- or T-lymphocytes. CRAM mRNA expression was increased upon stimulation with IFNγ and LPS but was not detectably inhibited by interleukin-10. CRAM was localized to the β-CKR cluster at chromosome 3p21 and physically linked to the CCR2 and CCR5 genes. In view of its similarity and genomic linkage to β-CKRs and restricted expression pattern, CRAM may play an important role in immune function. The existence of CRAM with alternative N-termini suggests a mechanism for altering ligand specificity and possibly signalling capacity of a single CKR.

Chemokines play critical roles in the chemoattraction and activation of leukocytes (Premack and Schall (1996) *Nat Med* 2:1174; Murphy (1996) *Cytokine Growth Factor* Rev 7:47; and Furie and Randolph (1995) *Am J Pathol* 146:1287), and have been divided into four families, based on the spacing of the first two of (usually) four conserved cysteine residues. The α chemokines, with a C-X-C motif, include IL-8, MIP-2α, GROβ, and ENA-78. The β chemokines (C-C motif), include MIP-1α, MCP-1, TARC, and RANTES. Recently, two new chemokine families have been defined by lymphotactin (γ) and CX$_3$Ckine (δ). Lymphotactin has only a single cysteine residue at the corresponding location for the C-C or C-X-C motif. Kelner and Zlotnik. (1995) *J Leukoc Biol* 57:778; Kennedy, et al. (1995) *J Immunol* 155:203. CX$_3$Ckine contains two cysteines separated by three intervening amino acids, and is tethered to the cell membrane via a long carboxy-terminal tail of mucin-like repeats. Bazan, et al. (1997) *Nature* 385:640.

Receptors for chemokines (CKRs) are G-protein coupled receptors (GPRs) with seven transmembrane domains. Novel CKRs have been identified by expression cloning of receptors binding a particular chemokine ligand (Holmes, et al. (1991) *Science* 253:1280) or mediating HIV fusion (Feng, et al. (1996) *Science* 272:872), by PCR using degenerate primers specific for conserved regions (Meyer, et al. (1996) *J Biol Chem* 271:14445; Ponath, et al. (1996) *J Exp Med* 183:2437; Daugherty, et al. (1996) *J Exp Med* 183:2349; Kurihara and Bravo (1996) *J Biol Chem* 271:11603; Power, et al. (1995) *J Biol Chem* 270:19495; Napolitano, et al. (1996) *J Immunol* 157:2759; and Raport, et al. (1996) *J Leukoc Biol* 59:18), and by random sequencing efforts followed by sequence analysis. While nearly 30 CKR-like genes have been cloned from mammals and mammalian viruses, only 17 have been shown to bind identified chemokines. Thus, a substantial number of CKR-like molecules remain "orphan receptors." Most CKRs with experimentally identified ligands bind to more than one ligand. IL-8 receptor B (CXCR2) binds to the α chemokines IL-8, NAP-2, and MGSA (Suzuki, et al. (1994) *J Biol Chem* 269:18263), whereas human CCR5 binds the β chemokines RANTES, MIP-1α, and MIP-1β (Raport, et al. (1996) *J Biol Chem* 271:17161; and Alkhatib, et al. (1996) *Science* 272:1955).

We have used cDNA library subtraction to isolate genes which are induced by monocyte activation. We thereby isolated a cDNA clone from a subtracted library enriched for monocyte activation-specific cDNAs that shows considerable homology to CC- or β-CKRs and maps within the β-CKR cluster on human chromosome 3p21. Expression of this gene was detected in several lymphoid tissues and in activated monocytes (but not lymphocytes). We provisionally designate this gene CRAM, for chemokine receptor of activated monocytes. CRAM is expressed as at least two alternatively spliced mRNAs encoding CKRs with different N-terminal amino acid sequences, suggesting a possible novel mechanism for regulation of CKR ligand specificity.

A. Cell Cultures and cDNA Library Construction

Human PBMC were purified by density gradient centrifugation on Ficoll (Pharmacia Biotech Inc., Piscataway, N.J.) using standard procedures. Monocytes were enriched from PBMC by adherence to tissue culture flasks and cultured in DMEM+10% FCS. Monocytes were activated by culture with 100 ng/ml IFNγ (R & D Systems Inc., Minneapolis, Minn.) and 1 μg/ml LPS (Life Technologies, Grand Island, N.Y.) for 1-15 hr. Total RNA was prepared by guanidinium isothiocyanate lysis followed by poly(A)+RNA selection using the OLIGOTEX kit (QIAGEN Inc., Chatsworth, Calif.). cDNA libraries containing >2×10$^6$ independent clones were constructed using the SuperScript cDNA Kit (Life Technologies).

B. cDNA Library Subtractions

Subtracted cDNA libraries (activated monocytes minus resting PBMC) were constructed. See, e.g., Hara, et al. (1994) *Blood* 84:189; and Kennedy, et al. (1996) *J Interferon Cytokine Res* 16:611. The major cDNA species present in the subtracted library were then added (1 μg each) to the resting PBMC cDNA library (150 μg); this mixture was used as the driver cDNA for a second round of subtraction using 5 μg of the activated monocyte cDNA library to enrich for induction-specific cDNAs which were less abundantly expressed.

C. DNA Sequencing and Bioinformatics

The nucleotide sequence of CRAM was determined using an ABI 377 automated sequencer and standard techniques. DNA sequence analyses were performed using Sequencher 3.0 (Gene Codes Corporation, Ann Arbor, Mich.) and MacVector 6.0 (Oxford Molecular Group). Comparisons to GenBank databases were performed using the BLAST program on web-based servers. Sequence alignments and phylogenetic analyses utilized ClustalW 1.6 (Higgins, et al. (1996) *Methods in Enzymology* 266:383) and TreeViewPPC 1.2 (Page (1996) *Computer Applications in the Biosciences* 12:357).

D. Analysis of CRAM mRNA Expression

Multiple-tissue Northern blots were purchased from Clontech (Palo Alto, Calif.). Poly(A)+RNA from human monocytes was used for RNA blot analysis. cDNA libraries from human cells (5 μg) in the pSPORT vector (Life Technologies) were digested with SalI and NotI to release cDNA inserts, electrophoresed on 1% agarose gels, and subjected to Southern blot transfer/hybridization. Hybridizations with $^{32}$P-labeled CRAM DNA fragments encoding the C-terminal 144 amino acids of the predicted ORF were done at 65° C. in ExpressHyb (Clontech, Palo Alto, Calif.) for 2 hr, followed by two stringent washes at 50° C. in 0.1×SSC, 0.1% SDS for 45 min. Hybridization was detected using a STORM 860 phosphorimager (Molecular Dynamics, Sunnyvale, Calif.). Reverse transcriptase PCR (RT-PCR) was performed with Superscript II reverse transcriptase (Life Technologies) and Taq DNA polymerase (Boehringer-Mannheim, Indianapolis, Ind.). PCR was for 35 cycles of 95° C./45 sec, 62° C./30 sec, 72° C./60 sec. Primers specific for exon 1 (5'-AGACGCTTCAGAGATCCTCTGGAGGCC; SEQ ID NO: 22) or exon 2 (5'-GAAGCTGCTTCGGGGGGTGAGCAAAC; SEQ ID NO: 23) were used in conjunction with an exon 3-specific primer (5'-CAAACACAGCAGAGACAGAGTGATGGCACC; SEQ ID NO: 24) for amplification.

E. Chromosomal Localization

PCR was performed on genomic DNA from the 83 cell lines of the Stanford Human Genome Center G3 radiation hybrid panel (Research Genetics, Huntsville, Ala.) using CRAM primers: (5'-GTGTCCTGGCATGGGTAACAGCC; SEQ ID NO: 25) and (5'-CGGTGGAATGGTCAGGTTCT-TCCC; SEQ ID NO: 26) as previously described for the GeneBridge 4 radiation hybrid panel (Samson, et al. (1996) *Genomics* 36:522). Data correlating the presence or absence of PCR product to each cell line were entered into the RHserver (Stanford Human Genome Center). Co-localized STSs were identified on the human physical map using the Entrez server (National Center for Biotechnology Information).

F. cDNA Cloning of CRAM

We employed subtractive hybridization to identify genes induced in monocytes upon activation by IFNγ and LPS. An activated monocyte cDNA library was first subtracted against a resting PBMC cDNA library. Seven prominent induced cDNAs thus identified were mixed with the resting PBMC library, which was then used as "driver" in another subtraction to generate a new library containing less abundantly expressed, induction-specific cDNAs. More than 100 clones were isolated from this second-round subtracted library, representing 55 unique cDNAs, 25 of which did not correspond to known cDNAs from the non-redundant section of GenBank. One of these clones contained a 1.5 kb insert encoding a large open reading frame with strong homology to all five known human β-CKRs. We designated this cDNA CRAM (chemokine receptor of activated monocytes; or M/DC CR).

G. Sequence Analysis of CKRs

A phylogenetic analysis of CKRs and related gene sequences revealed two major clades or phylogenetic groups, with several receptors remaining unclustered outside these two groups. Interestingly, the two groups correlated with known ligand specificities: the α-CKR IL-8RA, IL-8RB, and fusin cluster in a single clade, while β-CKR CCR1 through CCR5 all cluster in a second clade. Of the seven receptors that do not fall into either group, one (DARC) is a promiscuous CKR that binds several α- and β-chemokines (Neote, et al. (1993) *J Biol Chem* 268:12247).

The 1536 bp CRAM cDNA encodes an ORF with a predicted size of about 356 amino acids. Phylogenetic analysis showed that CRAM was most closely related to β-CKRs, exhibiting strongest homology to CCR1 (46% identity and 65% similarity), and the least to CCR4, with only 33% identity and 48% similarity. Three other human orphan receptors V28, TER1, and GPR5 also group with β-CKRs, and like CRAM, may be receptors for known or yet to be identified β chemokines.

The two most highly conserved regions among CCR1 through CCR5 are in transnxembrane region 2 (YLLNLAIS-DLLE; "TM2") amino acids 80-91 of SE ID NO: 14) and immediately after transmembrane region 3 (IDRYLAIVI-IAVIY; "DRY-box") amino acids 136-147 of SEQ ID NO: 14). These two 12-amino acid segments are invariant among CCR1 through CCR4; CCR5 shares 22 of these 24 residues. These regions are sometimes conserved among other mammalian GPR and have been used for degenerate primer PCR to clone new CKRs. CRAM is divergent in these regions (9 out of 12 amino acids in TM2; 4 out of 12 in the DRY-box), which may explain why such approaches have failed to identify CRAM. The DRY-box is in one of the three intracellular loops, and is thought to play a role in binding to heterotrimeric G proteins (Damaj, et al. (1996) *FASEB J* 10:1426). Because of the divergence of CRAM from the other β-CKRs in these regions, it may interact with a different subset of G protein subunits, possibly transducing a signal different from that induced via other β-CKRs.

While human CKR genes have been localized to several different chromosomes, the β-CKR genes CCR1, CCR2, CCR3, and CCR5 all cluster in a 350 kb region at chromosome 3p21.3 (Samson, et al. (1996) *Genomics* 36:522). CCR4 and the orphan receptors TER1 and GPR5 are also located in this 3p21 region Napolitano, et al. (1996) *J Immunol* 157:2759; Samson, et al. (1996) *Genomics* 36:522; Heiber, et al. (1995) *DNA Cell Biol* 14:25). We determined the chromosomal location of CRAM. The Stanford G3 panel of radiation hybrids was used as templates for PCR reactions with CRAM-specific primers. Among the 83 different hybrids, 11 contained the CRAM gene as assessed by PCR. CRAM co-localized with STS D3S3888, which is located at chromosome 3p21.3. Confirmation of this result was obtained from the recently completed sequence of the 143 kb BAC clone 110p12 from the 3p21 region (GenBank accession U95626); this BAC contains the loci CCR2, CCR5, and CRAM.

A related but different CRAM cDNA was also isolated from an activated monocyte library by random sequencing. Comparing the two forms of CRAM to the genomic sequence revealed the existence of two short exons (corresponding to 95750-96064 bp and 96186-96256 bp on BAC 110p12), followed by a large third exon (96630-98093 bp) that contains almost the entire ORF for CRAM. These two CRAM cDNAs consist of either exon 2 and exon 3 (1536 bp), or exon 1 and exon 3 (1780 bp). Exon 2 contributes 12 amino acids in frame with exon 3 to form the entire 356 residue polypeptide (CRAM-A). As exon 1 has no methionine in frame with the ORF in exon 3, the translated protein from this splice variant would start with Met-13, resulting in an N-terminally truncated protein of 344 amino acids (CRAM-B).

H. Expression of CRAM mRNA

RNA blot analysis showed expression largely restricted to lymphoid tissues. Prominent expression of CRAM mRNA was observed in spleen, lymph node, thymus, bone marrow, and fetal liver. Very little expression was detected in brain, liver, muscle, kidney, pancreas, or PBL, with moderate signals in heart, placenta, lung, and appendix. This pattern of expression was similar to that of the CKR-like gene TER1 (Napolitano, et al. (1996) *J Immunol* 157:2759), but quite different from the related orphan receptor genes V28 and blr1 (Forster, et al. (1996) *Cell* 87:1037; and Raport, et al. (1995) *Gene* 163:295).

Data from various hematopoietic cell types showed no evidence for CRAM expression in resting or activated lymphocytes, or in splenocytes. CRAM mRNA was also not detected in resting monocytic cell lines, but was strongly expressed in primary monocytes and THP-1 cells upon activation with IFNγ and LPS. Both CRAM-A and CRAM-B mRNAs were induced, as detected by RT-PCR using exon 1- and exon 2-specific primers. In contrast to several other monocyte activation-induced genes, such as monokines (TNFα, IL-1, IL-6) and some cell-surface antigens (Ho and Moore. (1994) *Therapeutic Immunology* 1:173). CRAM mRNA expression was not detectably inhibited by IL-10. Thus, CRAM expression in monocytes may be regulated via a different mechanism compared to that of several other activation-induced genes.

While most CKR genes lack introns, the genes for human CCR2 and mouse CXCR4 (fusin) both contain at least two exons and both have two alternatively spliced forms. CCR2A and CCR2B differ in the C-terminus (Charo, et al. (1994) *Proc. Natl. Acad. Sci. U.S.A.* 91:2752), whereas CXCR4 has two forms that differ by two amino acids at the N-terminus (Heesen, et al. (1997) *J. Immunol.* 158:3561). The two forms of CCR2 have identical ligand specificities, but differ with respect to which $G_\alpha$ subunits they can couple (Kuang, et al. (1996) *J. Biol. Chem.* 271:3975); the two forms of CXCR4 can both serve as functional CKRs for SDF-1α (Heesen, et al. (1997) *J. Immunol.* 158:3561), although their ligand specificities and interactions with HIV have not been fully characterized. The N-terminal sequence of CKRs, along with portions of the extracellular loops, is known to play a key role in ligand binding and possibly receptor activation (Ahuja, et al. (1996) *J. Biol. Chem.* 271:225; Lu, et al. (1995) J. Biol. Chem. 270:26239; Horuk (1994) *Immunol. Today* 15:169; Wells, et al. (1996) *J Leukoc Biol* 59:53; and Hebert, et al. (1993) *J. Biol. Chem.* 268:18549). This region of CKR is also important for HIV fusion (Rucker, et al. (1996) *Cell* 87:437.), which is antagonized by chemokine ligands (Paxton, et al. (1996) *Nature Med.* 2:412; and Cocchi, et al. (1995) *Science* 270:1811). Thus it is possible that CRAM-A and CRAM-B may exhibit different but likely overlapping ligand specificities. Regulated expression of alternative forms of a single CKR, combined with possible modulation of specificity of ligand-receptor interaction by chemokine-proteoglycan interaction (Graham, et al. (1996) *The EMBO J.* 15:6506; and Witt and Lander (1994) *Curr. Biol.* 4:394), might control the spectrum of chemokines to which a particular cell could respond. In addition, these observations may provide one possible explanation of non-reciprocal desensitization phenomena observed with, for example, the chemokines RANTES, MIP-1α, and MCAF (Wang, et al. (1993) *J Exp Med* 177:699).

The similarity of CRAM to the other β-CKRs, its chromosomal localization in the β-CKR gene cluster, and induction of its expression in monocytes upon activation all argue that CRAM may play an important role in regulation of immune function.

VIII. Screening for Receptor/Ligand

Labeled reagent is useful for screening of an expression library made from a cell line which expresses a chemokine or receptor, as appropriate. Standard staining techniques are used to detect or sort intracellular or surface expressed ligand, or surface expressing transformed cells are screened by panning. Screening of intracellular expression is performed by various staining or immunofluorescence procedures. See also, e.g., McMahan, et al. (1991) *EMBO J.* 10:2821-2832.

For example, on day 0, precoat 2-chamber permanox slides with 1 ml per chamber of fibronectin, 10 ng/ml in PBS, for 30 min at room temperature. Rinse once with PBS. Then plate COS cells at $2-3\times10^5$ cells per chamber in 1.5 ml of growth media. Incubate overnight at 37° C.

On day 1 for each sample, prepare 0.5 ml of a solution of 66 μg/ml DEAE-dextran, 66 μM chloroquine, and 4 μg DNA in serum free DME. For each set, a positive control is prepared, e.g., of huIL-10-FLAG cDNA at 1 and 1/200 dilution, and a negative mock. Rinse cells with serum free DME. Add the DNA solution and incubate 5 hr at 37° C. Remove the medium and add 0.5 ml 10% DMSO in DME for 2.5 min. Remove and wash once with DME. Add 1.5 ml growth medium and incubate overnight.

On day 2, change the medium. On days 3 or 4, the cells are fixed and stained. Rinse the cells twice with Hank's Buffered Saline Solution (HBSS) and fix in 4% paraformaldehyde (PFA)/glucose for 5 min. Wash 3× with HBSS. The slides may be stored at −80° C. after all liquid is removed. For each chamber, 0.5 ml incubations are performed as follows. Add HBSS/saponin (0.1%) with 32 μl/ml of 1M $NaN_3$ for 20 min. Cells are then washed with HBSS/saponin 1×. Add antibody complex to cells and incubate for 30 min. Wash cells twice with HBSS/saponin. Add second antibody, e.g., Vector anti-mouse antibody, at 1/200 dilution, and incubate for 30 min. Prepare ELISA solution, e.g., Vector Elite ABC horseradish peroxidase solution, and preincubate for 30 min. Use, e.g., 1 drop of solution A (avidin) and 1 drop solution B (biotin) per 2.5 ml HBSS/saponin. Wash cells twice with HBSS/saponin. Add ABC HRP solution and incubate for 30 min. Wash cells twice with HBSS, second wash for 2 min, which closes cells. Then add Vector diaminobenzoic acid (DAB) for 5 to 10 min. Use 2 drops of buffer plus 4 drops DAB plus 2 drops of $H_2O_2$ per 5 ml of glass distilled water. Carefully remove chamber and rinse slide in water. Air dry for a few minutes, then add 1 drop of Crystal Mount and a cover slip. Bake for 5 min at 85-90° C.

Alternatively, the binding compositions are used to affinity purify or sort out cells expressing the ligand or receptor. See, e.g., Sambrook, et al. or Ausubel et al.

All references cited herein are incorporated herein by reference to the same extent as if each individual publication or patent application was specifically and individually indicated to be incorporated by reference.

Many modification an variations of this invention can be made without departing from its spirit and scope, as will be apparent to those skilled in the art. The specific embodiments described herein are offered by way of example only, and the invention is to be limited only by the terms of the appended claims, along with the full scope of the equivalents to which such claims are entitled.

What is claimed is:

1. A substantially pure or isolated polypeptide comprising amino acids Gln1 to Leu127 of SEQ ID NO: 4.

2. The polypeptide of claim 1 wherein the polypeptide is detectably labeled.

3. The polypeptide of claim 1 wherein the polypeptide is attached to a solid substrate.

4. The polypeptide of claim 1 wherein the polypeptide is a fusion protein.

5. The polypeptide of claim 4 wherein the protein to which said polypeptide is fused is a member selected from the group consisting of bacterial β-galactosidase, trpE, protein A, β-lactamase, alpha amylase, alcohol dehydrogenase, luciferase, FLAG polypeptide tag, and yeast alpha mating factor.

6. The polypeptide of claim 1 comprising the amino acid sequence set forth in SEQ ID NO; 4.

7. A composition comprising the polypeptide of any one of claims 1 to 6.

* * * * *